United States Patent [19]

Lee et al.

[11] Patent Number: 5,171,863

[45] Date of Patent: Dec. 15, 1992

[54] INTERMEDIATES FOR PREPARING 4-SUBSTITUTED 2-5(H)-FURANONES AS ANTI-INFLAMMATORY AGENTS

[75] Inventors: Gary C. M. Lee, Laguna Hills; Michael E. Garst, Newport Beach, both of Calif.

[73] Assignee: Allergan, Inc., Irvine, Calif.

[21] Appl. No.: 792,833

[22] Filed: Nov. 15, 1991

Related U.S. Application Data

[60] Division of Ser. No. 690,444, Apr. 24, 1991, Pat. No. 5,082,954, which is a continuation-in-part of Ser. No. 493,895, Mar. 15, 1990, Pat. No. 5,081,147, Ser. No. 510,368, Apr. 17, 1990, Pat. No. 5,037,811, Ser. No. 192,808, May 11, 1988, abandoned, Ser. No. 510,367, Apr. 17, 1990, Pat. No. 5,043,457, Ser. No. 427,268, Oct. 25, 1989, Pat. No. 5,059,611, Ser. No. 501,637, Oct. 25, 1989, and Ser. No. 426,243, Oct. 25, 1989, Pat. No. 5,089,485, which is a continuation-in-part of Ser. No. 273,294, Nov. 18, 1988, abandoned, said Ser. No. 192,808, is a continuation-in-part of Ser. No. 59,282, Jun. 8, 1987, abandoned, said Ser. No. 427,268, is a continuation-in-part of Ser. No. 273,300, Nov. 18, 1988, abandoned, said Ser. No. 501,637, is a continuation-in-part of Ser. No. 281,154, Dec. 7, 1988, abandoned.

[51] Int. Cl.[5] ............................. C07D 307/60
[52] U.S. Cl. ............................. 549/214; 514/229; 514/337; 514/379; 514/383; 549/222; 549/313; 549/318; 549/483; 549/486; 549/499
[58] Field of Search ............................. 549/214

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |
| 5,059,611 | 10/1991 | Lee | 514/336 |
| 5,081,147 | 1/1992 | Lee | 514/471 |
| 5,081,261 | 1/1992 | Lee | 549/222 |
| 5,082,954 | 1/1992 | Lee | 549/214 |
| 5,089,485 | 2/1992 | Lee | 514/99 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjuklian, et al., Chemical Abstracts, vol. 106, 156260c, p. 670 (1987).
Reynolds, et al., J. Am. Chem. Soc., 110, pp. 5172-5177 (1988).
Tocanne et al., Chemical Abstracts 69 76581k, p. 7146 (1968).
Deems, et al, Biochimica et Biophysica Acta, 917 pp. 258-268 (1987).
Scheuer et al., Journal of the American Chemical Society 100:1 p. 307 (Jan. 4, 1978).
Graziano, et al., Chemical Abstracts 107, (1987), 236559t.
Roll et al., Org. Chem. 1988, 53 3276-8.
Negishi et al., J. Org. Chem 45, pp. 5223-5225, (1980).
E. D. de Silva et al., "Tetrahedron Letters", 21:1611-1614 (1980).
Nakagawa et al., "Aldose reductase inhibitor from palaun sponges" Chem. Abstract 106: 96126b.
Tanaka, et al., The Chemical Society of Japan, Chemistry Letters, pp. 633-636 (1983).
Tanis, et al., Tetrahedron Letters, vol. 25, No. 40, pp. 4451-4454 (1984)-Furans in Synthesis 4. Silyl Furans as Butenolide Equivalents.
Graziano, et al, "Photosensitized Oxidation of Furans, Part 12, Solvent Effects in Thermal Rearrangement of the 2,5-Peroxides of 2,5-Unsubstituted Furans", J. Chem, Soc., Perkin Trans, 1, (8), 1833-9, Apr. 19, 1989.
David Nettleton, et al, Inflammation Research Association, Fifth International Conference Poster Session, Phospholipase $A_2$ Inhibition by Dihydrofuranones, Sep. 23-27, 1990.

*Primary Examiner*—C. Warren Ivy
*Assistant Examiner*—James H. Turnipseed
*Attorney, Agent, or Firm*—Gabor L. Szekers; Martin A. Voet; Robert J. Baran

[57] ABSTRACT

Anti-inflammatory 4-substituted 2-furanones are made from intermediates having the formulas:

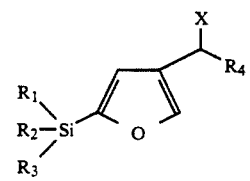

Formula 1 in which $R_1$, $R_2$ and $R_3$ independently are n-alkyl of 1 to 6 carbons, or branched chain alkyl of 1 to 6 carbons; X is H, OH, $NH_2$, I or Br; $R_4$ is H, alkyl of 1-20 carbons, phenyl[$C_1$-$C_{20}$alkyl], naphthyl[$C_1$-$C_{20}$alkyl], $CH_2OH$, $CH_2NH_2$, $CH_2CH_2OH$, $CH_2$—CHO, $CH_2$—COOH or $CH_2$—$COOR_5$, and $R_5$ is alkyl of 1 to 6 carbons, with the proviso that when X is hydrogen then $R_4$ is selected from the group consisting of $CH_2OH$, $CH_2NH_2$, $CH_2CH_2OH$, $CH_2$—CHO, or $CH_2$—$COOR_5$;

(Abstract continued on next page.)

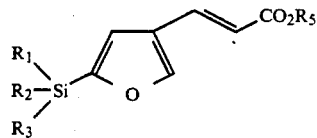

Formula 2 in which $R_1$, $R_2$ $R_3$ independently are n-alkyl of 1 to 6 carbons, or branched chain alkyl of 1 to 6 carbons, and $R_5$ is alkyl of 1 to 6 carbons;

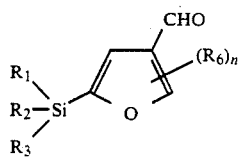

Formula 3A

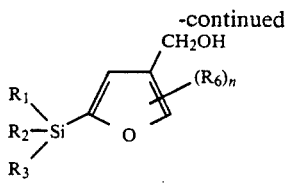

Formula 3B in which $R_1$, $R_2$ and $R_3$ independently are n-alkyl of 1 to 6 carbons, or branched chain alkyl of 1 to 6 carbons, and $R_6$ is phenyl, or alkyl of 1 to 6 carbons, and

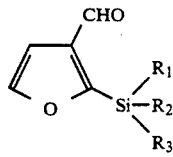

Formula 4A

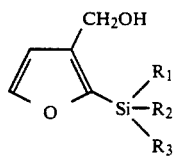

Formula 4B in which $R_1$, $R_2$ and $R_3$ independently are n-alkyl of 1 to 6 carbons, or branched chain alkyl of 1 to 6 carbons.

15 Claims, No Drawings

INTERMEDIATES FOR PREPARING 4-SUBSTITUTED 2-5(H)-FURANONES AS ANTI-INFLAMMATORY AGENTS

BACKGROUND OF THE INVENTION

1. Cross-Reference to Related Applications

This application is a divisional of application Ser. No. 690,444, filed on Apr. 24, 1991, now U.S. Pat. No. 5,082,954, and which is a continuation-in-part of the following applicaitons, all of which are assigned to the same assignee as the present application, and all of which have at least one inventor common with the present application: Ser. No. 07/493,895 filed on Mar. 15, 1990 now U.S. Pat. No. 5,081,147; Ser. No. 07/510,368 filed on Apr. 17, 1990 now U.S. Pat. No. 5,037,811 application Ser. No. 07/192,808 filed on May 11, 1988 now abandoned which is itself a continuation-in-part of application Ser. No. 059,282 filed on Jun. 8, 1987, now abandoned; Ser. No. 07/510,367 filed on Apr. 17, 1990 now U.S. Pat. No. 5,043,457; Ser. No. 07/427,268 filed on Oct. 25, 1989 now U.S. Pat. No. 5,059,611, which is itself a continuation-in-part of application Ser. No. 273,300 filed on Nov. 18, 1988, now abandoned; Ser. No. 07/501,637 filed on Oct. 25, 1989 now abandoned which is itself a continuation-in-part of application U.S. Ser. No. 281,154 filed on Dec. 7, 1988, now abandoned; Ser. No. 07/426,243 filed on Oct. 25, 1989 now U.S. Pat. No. 5,089,485 which is itself a continuation-in-part of application Ser. No. 273,294 filed on Nov. 18, 1988, now abandoned.

2. Field of the Invention

This invention is directed to novel 2-trialkylsilyl 4-substituted furan compounds which serve as intermediates for the synthesis of biologically active substituted 2-furanone compounds which are active as anti-inflammatory agents. The present invention is also directed to the chemical processes in which the novel 2-trialkylsilyl 4-substituted furan compounds intermediates are prepared, and to the chemical processes in which the anti-inflammatory substituted 2-furanone compounds are prepared from the novel intermediate compounds.

3. Brief Description of the Prior Art

Manoalide is a compound isolated from a marine sponge [E. D. de Silva et a.., *Tetrahedron Letters* 21:1611–1614 (1980)] which has anti-inflammatory, immunosuppressive and analgesic properties. Manoalide the structure of which is shown below, includes a 5-hydroxy-2(5H)-furanone moiety, attached in the 4-position of the furanone ring to the rest of the molecule. Certain analogs of manolide, such as seco-manoalide and dehydro-seco-manoalide also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

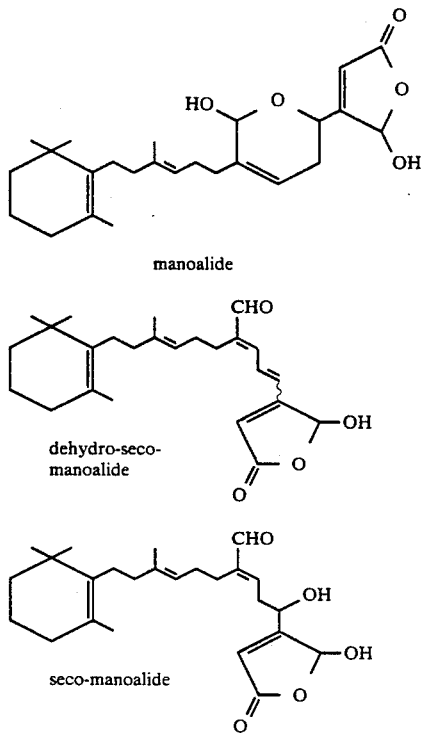

Synthetic analogs of manoalide, particularly analogs having various substituents on the furanone moiety of manoalide, are described in several applications for U.S. Letters Patent by the same inventor as in the present application, the following of which have been allowed and are expected to issue as U.S. Patent:

U.S. Ser. No. 281,126 filed on Dec. 7, 1988, now abandoned.

Published European Patent Application No. 0 295 056 discloses 4-substituted 5-hydroxy-2(5H)-furanones having anti-inflammatory, immunosuppressive and anti-proliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

In addition to the foregoing references which are primarily directed to biologically active 2(5H)-furanone derivatives, the following patents and publications pertain to the chemistry of furan compounds, as background to the present invention:

U.S Pat. No. 4,935,530; Feringa, B. L. Recl. Trav. Chim. Pays-Bas. (1987), 106, 469; Wasserman, H. R.; Ives, J. L. Tetrahedron (1981), 37, 1825; Matsumoto, M. in "Singlet oxygen" vol. II, edited by Frimer A. A., CRC Press Inc., Boca Raton, Fla., 1985; Kuwajima, I.; Urabe, H. Tetrahedron Lett. (1981), 22, 5191; Katsumura, S.; Hori, K.; Fujimara, S.; Isoe, S. Tetrahedron Lett. (1985), 26, 4625; Garst, M. E.; Tallman, E. A.; Bonfiglio, J. N.; Harcourt, D.; Ljungwe, E. B.; Tran, A. Tetrahedron Lett. (1986), 27, 4533.

SUMMARY OF THE INVENTION

The present invention covers compounds of the formula

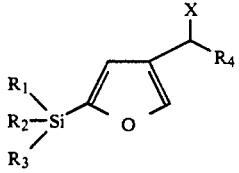

Formula 1 in which $R_1$, $R_2$ and $R_3$ independently are D-alkyl of 1 to 6 carbons, or branched chain alkyl of 1 to 6 carbons; X is H, OH, $NH_2$, I or Br; $R_4$ is H, alkyl of 1–20 carbons, phenyl[$C_1$-$C_{20}$alkyl], naphthyl[$C_1$-$C_{20}$alkyl], $CH_2OH$, $CH_2NH_2$, $CH_2CH_2OH$, $CH_2$—CHO, $CH_2$—COOH or $CH_2$—$COOR_5$, and $R_5$ is alkyl of 1 to 6 carbons, with the proviso that when X is hydrogen then $R_4$ is selected from the group consisting of $CH_2OH$, $CH_2NH_2$, $CH_2CH_2OH$, $CH_2$—CHO, or $CH_2$—$COOR_5$.

The present invention also covers compounds of the formula

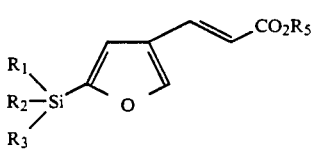

Formula 2 in which $R_1$, $R_2$ and $R_3$ independently are n-alkyl of 1 to 6 carbons, or branched chain alkyl of 1 to 6 carbons, and $R_5$ is alkyl of 1 to 6 carbons.

Further, the present invention covers compounds of the formula

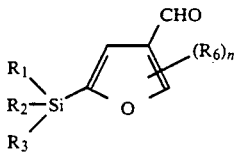

Formula 3A

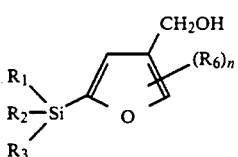

Formula 3B in which $R_1$, $R_2$ and $R_3$ independently are n-alkyl of 1 to 6 carbons, or branched chain alkyl of 1 to 6 carbons, and $R_6$ is phenyl, or alkyl of 1 to 6 carbons.

Still further the present invention covers compounds of the formula

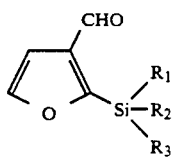

Formula 4A

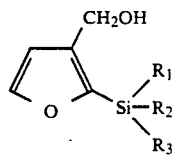

Formula 4B in which $R_1$, $R_2$ and $R_3$ independently are n-alkyl of 1 to 6 carbons, or branched chain alkyl of 1 to 6 carbons.

In another aspect the present invention relates to the processes in which the above-defined compounds are made. In still another aspect the present invention relates to the chemical processes in which the novel compounds of the invention, as generally represented by Formulas 1–4, are converted into the anti-inflammatory furanone compounds. These steps are described in detail in the ensuing description, and generally speaking include one or more steps where the substituent in 4-position of the furan nucleus (as shown in Formulas 1–4) is reacted with suitable reagents, and a step wherein an intermediate 2-trialkylsilyl-4-substituted furan is subjected to oxydation by singlet oxygen, to provide, generally speaking, a hydroxylated furanone. With reference to the compounds of the invention shown in Formula 1, singlet oxydation of intermediates derived from that formula provide, in accordance with the present invention, anti-inflammatory 4-substituted 5-hydroxy-2(5H)-furanones.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, the term "long chain alkyl" also means the former broad definition of "alkyl" groups but with the restriction that the group has no less than 4 carbon atoms, and no more than approximately 25 carbon atoms.

Unless specifically noted otherwise, preferred amides are the mono- and di-substituted amides derived from the saturated aliphatic radicals of ten or fewer carbon atoms, or the cyclic or saturated aliphatic-cyclic radicals of 5 to 10 carbon atoms.

Some of the compounds of the invention, and some of the anti-inflammatory furanone compounds which are made from the compounds of the invention, may contain a chiral center. Other compounds of the invention, and some of the anti-inflammatory furanone compounds which are made from the compounds of the invention, may contain more than one chiral center. Accordingly, these compounds may be prepared as mixtures of enantiomeric compounds (where the enatiomers may or may not be present in equal amounts) or as optically pure enantiomers. When there is more than one chiral center, the compounds may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the above-noted forms, including optically pure enantiomers and mixtures thereof, as well as all diastereomers, are within scope of the present invention.

Some of the compounds of the invention, and some of the anti-inflammatory furanone compounds which are made from the compounds of the invention, may have cis and trans stereoisomers The scope of the invention includes both pure stereoisomers as well as mixtures thereof.

A pharmaceutically acceptable salt may be prepared from any of the anti-inflammatory furanone compounds made in accordance with this invention from the intermediate compounds of this invention, provided the anti-inflammatory furanone has a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention with reference to Formula 1 and with respect to the $R_1$, $R_2$, and $R_3$ groups, are those where $R_1$, $R_2$, and $R_3$ independently are normal alkyl of 1 to 6 carbons, or branched chain alkyl of 1 to 6 carbons. More preferred are compounds of Formula 1 where $R_1$, $R_2$, and $R_3$ are all methyl, or all ethyl, and also compounds where $R_1$ and $R_2$ are methyl and $R_3$ is tertiary butyl.

With respect to $R_4$ in Formula 1, the preferred compounds in accordance with the invention are those where $R_4$ is H, or a long chain alkyl group of 4 to 25 carbons, more preferably a long chain alkyl group having 9 to 20 carbons. Alternatively and preferably $R_4$ is $CH_2OH$, $CH_2NH_2$, $CH_2CH_2OH$, $CH_2-CHO$, $CH_2-COOH$ or $CH_2-COOCH_3$ or $CH_2-COOCH_2CH_3$.

With respect to the substituent X in Formula 1, the preferred compounds are those where X is H, OH or $NH_2$, with the condition that when X is H then $R_4$ is not H nor alkyl.

The most preferred compounds of the invention corresponding to Formula 1, are listed below:

$R_1=R_2=R_3=CH_3CH_2-$, $X=OH$ and $R_4=H$; Compound 1

$R_1=R_2=R_3=CH_3CH_2-$, $X=NH_2$ and $R_4=H$; Compound 2

$R_1=R_2=R_3=CH_3CH_2-$, $X=OH$ and $R_4=CH_3(CH_2)_{11}-$; Compound 3

$R_1=R_2=R_3=CH_3CH_2-$, $X=NH_2$ and $R_4=CH_3(CH_2)_{11}-$; Compound 4

$R_1=R_2=R_3=CH_3CH_2-$, $X=H$ and $R_4=CH_2CHO$; Compound 5

$R_1=R_2=R_3=CH_3CH_2-$, $X=OH$ and $R_4=CH_2OH$; Compound 6

$R_1=R_2=R_3=CH_3CH_2-$, $X=OH$ and $R_4=CH_2NH_2$; Compound 7

$R_1=R_2=R_3=CH_3CH_2-$, $X=NH_2$ and $R_4=CH_2NH_2$; Compound 8

$R_1=R_2=R_3=CH_3CH_2-$, $X=I$ and $R_4=H$. Compound 9

The preferred compounds of the present invention shown by Formula 2, are those where the $R_1$, $R_2$, and $R_3$ groups are normal alkyl of 1 to 6 carbons, or branched chain alkyl of 1 to 6 carbons. More preferred are compounds of Formula 2 where $R_1$, $R_2$, and $R_3$ are all methyl, or all ethyl, and also compounds where $R_1$ and $R_2$ are methyl and $R_3$ is tertiary butyl.

With respect to $R_5$ in Formula 2 in the preferred compounds of the invention $R_5$ is normal alkyl, most preferably methyl or ethyl. Methyl 3-(2-triethylsilyl-4-furyl)propen-2-oate (Compound 10) and octyl 3-(2-triethylsilyl-4-furyl)propen-2-oate (Compound 11) and the corresponding trimethylsilyl derivatives, are examples of the most preferred compounds in this regard.

Among the compounds of the invention shown by Formula 3A and 3B those are preferred where $R_1$, $R_2$, and $R_3$ groups are normal alkyl of 1 to 6 carbons, or branched chain alkyl of 1 to 6 carbons. More preferred are compounds of Formula 3 where $R_1$, $R_2$, and $R_3$ are all methyl, or all ethyl, and also compounds where $R_1$ and $R_2$ are methyl and $R_3$ is tertiary butyl Compounds of this formula are further preferred where $R_6$ is methyl and n is 1 or 2. The most preferred compounds in this regard are 2-triethylsilyl-3-methyl-4-furaldehyde (Compound 12) and 2-trimethylsilyl-5-methyl-4-furaldehyde (Compound 13), 2-triethylsilyl-3,5-dimethyl-4-furaldehyde (Compound 14) and the corresponding (and respective) trimethyl silyl or triethyl silyl derivatives.

With respect to the compounds of the invention shown in Formula 4A and Formula 4B, those are preferred where the $R_1$, $R_2$, and $R_3$ groups are normal alkyl of 1 to 6 carbons, or branched chain alkyl of 1 to 6 carbons. More preferred are compounds of Formula 4A and 4B where $R_1$, $R_2$, and $R_3$ are all methyl, or all ethyl, and also compounds where $R_1$ and $R_2$ are methyl and $R_3$ is tertiary butyl. The most preferred compound of Formula 4A is 2-triethylsilyl-3-furaldehyde (Compound 15).

The compounds of the invention are useful as intermediates in the synthesis of compounds which themselves are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds (or salts thereof) made from the intermediates of this invention include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds prepared from the intermediates of this invention is demonstrated by inhibition of the enzyme phospholipase $A_2$ in vitro and by reduction of inflammation in the mouse ear anti-inflammatory assay in vivo.

Activity of compounds prepared from the compounds of this invention may also be demonstrated by inhibition of phosphoinositide-specific phospholipase C. This activity has been reported for manoalide and may indicate anti-inflammatory utility. Bennett et al, *Molecular Pharmacology* 32:587-593 (1987).

Activity of the compounds prepared from the compounds of the invention may also be demonstrated by inhibition of ornithine decarboxylase, a rate limiting enzyme in cellular growth, which indicates use in treating psoriasis and neoplasis.

The compounds prepared from the intermediates of this invention also modify calcium homeostasis. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), disease, of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The biologically active compounds prepared from the compounds of this invention have activity which is similar to that of manoalide, that is the compounds appear to be devoid of the endocrine properties of the glucocorticoids while having anti-inflammatory and immunosuppressive properties.

The biologically active compounds made from the intermediate compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

The pharmaceutical compositions in which the biologically active compounds, made from the intermediate compounds of this invention, are administered, comprise the active compounds as well as pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
|---|---|
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
|---|---|
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
|---|---|
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The active compounds prepared from the intermediate compounds of this invention, may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds can be demonstrated, are described below.

Calcium Channel (mobilization) Inhibition Assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5–10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MgSO_4$, 1 mg/ml glucose and 1 mg/ml pyruvate and 1.4 mM calcium (medium A). Approximately $5 \times 10^6$ cells were suspended in medium A and incubated with 4 uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. $[Ca^{2+}i]$ was calculated using the following formula:

$$[Ca^{2+}]_i = 220 \times \frac{F - F_{min}}{F_{max} - F}$$

All fluorescence values were measured relative to a EGTA-quenched signal determined as follows: F was the relative fluorescence measurement of the sample. $F_{max}$ was determined by lysing the cells with digitonin (100 ug/ml) in DMSO. After $F_{max}$ was determined the pH was adjusted to 8, with NaOH and $Ca^{2+}$ chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900–904].

Inhibition of Phospholipase $A_2$

The effect of compounds made from the intermediate compounds of this invention on bee venom phospholipase $A_2$ is determined by the following procedure:

a. Bee venom phospholipase $A_2$ in 10 uM HEPES (pH 7.4) with 1 mM $CaCl_2$ is incubated with vehicle or test agent for 1.0 hour at 41°.
b. 1.36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.
c. Start the reaction by the addition of enzyme (0.495 units/ml).
d. Incubation for 15 sec. at 41°.
e. Reaction is terminated by addition of 2.5 ml of isopropanol: n-heptane: 0.5M $H_2SO_4$ (40:10:1; v:v:v:).
f. 2.0 ml n-heptane and 1.0 ml $H_2O$ added; mixture centrifuged.
g. 2.0 ml n-heptane removed and treated with 200–300 mg of silica gel HR60.
h. Samples centrifuged; 1 ml of n-heptane SN removed and added to 10 ml scintillation fluid.
i. Samples counted on a scintillation counter.

Inhibition of Phosphoinositide-specific Phospholipase C

The effect of compounds made from the intermediate compounds of this invention on phosphoinositide-specific phospholipase C may be determined by procedures described by Bennett et al, *Molecular Pharmacology* 32:587–593 (1987).

Specific Embodiments

Specific examples and procedures for preparing the compounds of the invention, as well as specific examples and procedures for preparing from the compounds of the invention the biologically active anti-inflammatory compounds, are provided below.

Generally speaking, and by way of general example and not limitation, the intermediate compounds embraced by Formula 1 which have one or more OH, $NH_2$ or SH groups are subjected to one or more steps of alkylation, acylation, sulphonylation or phosphorylation or like reaction. Compounds embraced by Formula 1 which have a functional group subject to a Grignard lithium halide or like reaction (such as an aldehyde or ester group) or subject to a Wittig (or like reaction), are reacted with a suitable reagent, followed, if desired, by acylation, sulphonylation and the like of alcohol (OH) or amino ($NH_2$) functions in the side chain. The resulting 2-trialkylsilyfuran intermediates, (which have in the 4 position of the furan nucleus the side chain which is desired for biological activity) are subjected to oxidation by singlet oxygen to provide the biologically active 4-substituted 5-hydroxy-2-(5H)-furanones. The conditions of the reactions with singlet oxygen are described in detail in connection with several specific examples. In general terms, these oxidation reactions are preferably conducted in a mixture of water and acetone or in a mixture of water and tetrahydrofuran, and in some instances in substantially neat tetrahydrofuran, in the presence of a catalyst, preferably Rose Bengal dye (preferably polymer bounded), which is added to the reaction mixture. The reaction mixture and vessel is flushed with oxygen and the reaction is conducted at low temperature, at approximately −78° C., or for the herein described reactions preferably at approximately 0° C., under a constant positive pressure of oxygen for a number of hours, typically 1 to 7 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

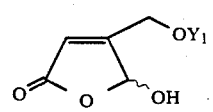

Formula 5

By way of further general examples, 2-triethylsilyl-4-hydroxymethylfuran (Compound 1; in Formula 1 $R_1=R_2=R_3=CH_3CH_2—$, $X=OH$ and $R_4=H$) or the corresponding trimethylsilyl compound, are utilized to make compounds of Formula 5, where $Y_1$ is alkyl having at least 6 carbon atoms, arylalkyl, aryl, substituted aryl, substituted arylalkyl, alkenyl containing one or more olephinic bonds and at least 6 carbon atoms, $CO—R_3$, $CO—OR_3$, $CONHR_3$, $SO_2R_3$, $SO_2NHR_3$ where $R_3$ is aryl, (such as phenyl or naphthyl) substituted aryl, (such as halogen or alkyl substituted phenyl or naphthyl) substituted arylalkyl, (such as phenyl or naphthyl $(C_1-C_6$ alkyl)) alkyl of 1 to 20 carbons, alkenyl containing one or more olephinic bonds; further $Y$ is $(CH_2)_n—O—R_4$, or $(CH_2)_n—O—(CH_2)_m—O—R_4$, where n, and m, are integers and are independently 1 to 25 and $R_4$ is phenyl, substituted phenyl or alkyl of one to 20 carbons; still further $Y$ is $PO(OH)_2$, $PO(OH)OR_5$, $PO(OH)R_5$ $PO(OR_5)_2$, where $R_5$ is independently phenyl, substituted phenyl, alkyl of 1 to 20 carbons or $R_5$ is $(CH_2)_n—N(R_5^*)_3$ where $R_5^*$ is alkyl of 1 to 20 carbons.

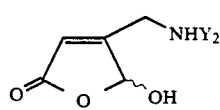

Formula 6

2-Triethylsilyl-4-aminomethylfuran (Compound 2, in Formula 1 $R_1=R_2=R_3=CH_3CH_2—$, $X=NH_2$ and $R_4=H$) or the corresponding trimethylsilyl compound are utilized to make compounds of Formula 6, where $Y_2$ is defined the same as $Y_1$ in connection with Formula 5.

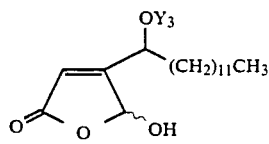

Formula 7

2-Triethylsilyl-4-(1-hydroxy-tridecyl)-furan (Compound 3; in Formula 1 $R_1=R_2=R_3=CH_3CH_2—$, $X=OH$ and $R_4=CH_3(CH_2)_{11}—$) or the corresponding trimethylsilyl compound are utilized to make compounds of Formula 7 where $Y_3$ is H, $C_1-C_{20}$ alkanoyl, trihaloacetyl, cyclohexanoyl, benzoyl, phenyl($C_{1-4}$ alkanoyl), phenyl($C_2-C_{14}$ alkenoyl), naphthoyl, or carbamoyl optionally N-substituted by one or two $C_{1-4}$ alkyl groups or by one alpha($C_1-C_4$ alkyl)benzyl group.

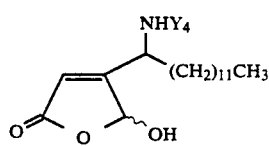

Formula 8

2-Triethylsilyl-4-(1-amino-tridecyl)-furan (Compound 4; in Formula 1 $R_1=R_2=R_3=CH_3CH_2—$, $X=NH_2$ and $R_4=CH_3(CH_2)_{11}—$) or the corresponding trimethylsilyl compound are utilized to make compounds of Formula 8 where $Y_4$ is H, $COR_3$, $SO_2R_8$, $PO(OR_7)R_8$, $PS(OR_7)R_8$; $R_3$ is $C_1-C_4$ alkyl, $C_1-C_4$ alkoxy, trifluoromethyl, $R_6-(C_1-C_4$ alkyl), $NHR_8$ or $N—R_9R_{10}$; $R_6$ is carboxy, $C_1-C_4$ alkoxycarbonyl, halo or $CONR_{11}R_{11}$; $R_7$ is hydrogen or $C_1-C_4$ alkyl or phenyl; $R_8$ is $C_1-C_4$ alkyl, alkoxy having 1-4 carbons, hydroxy, hydrogen or $C_1-C_6$ alkanoyl; $R_9$ is H or $C_1-C_4$ alkyl; $R_{10}$ is H, $C_1-C_4$ alkyl or $SO_2NR_2R_2$; and $R_{11}$ is H or $C_1-C_4$ alkyl.

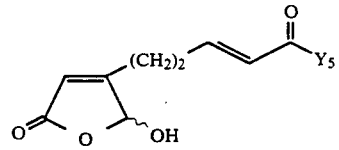

Formula 9

3-(2-Triethylsilyl-4-furyl)propan-1-al (Compound 5; in Formula 1 $R_1=R_2=R_3=CH_3CH_2—$, $X=H$ and $R_4=CH_2CHO$) or the corresponding trimethylsilyl compound are utilized to make compounds of Formula 9, where $Y_5$ is $C_7-C_{14}$ alkyl, $C_7-C_{14}$ alkoxide, $N(C_1-C_4$alkyl$)_3—(CH_2)_{2-8}Z$ or CCM; Z is H or $CO_2H$ and M is $C_7-C_{14}$ alkyl; phenyl($C_1-C_4$ alkyl) optionally substituted on the phenyl ring by 1-3 halo substituent; M is further pyridyl($C_1-C_4$ alkyl), or naphthyl($C_1-C_6$ alkyl).

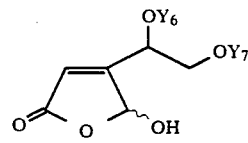

Formula 10

2-Triethylsilyl-4-(1,2-dihydroxy-ethyl)furan (Compound 6; in Formula 1 $R_1=R_2=R_3=CH_3CH_2—$, $X=OH$ and $R_4=CH_2OH$) or the corresponding trimethylsilyl compound are utilized to make compounds of Formula 10 where $Y_6$ is H, $C_1-C_{14}$-alkanoyl, $CONHR_3$, or $CO_2R_4$; $R_3$ is phenyl or $C_1-C_4$ alkyl; $R_4$ is $C_1-C_6$ alkyl; and $Y_7$ is $C_7-C_{14}$ alkanoyl, N-($C_6-C_{14}$ alkyl) carbamoyl, naphthyl-($C_1-C_6$ alkyl), pyridyl-($C_1-C_6$ alkyl) and methoxyethoxymethoxymethyl.

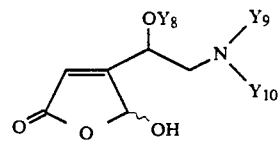

Formula 10

2-Triethylsilyl-4-(1-hydroxy-2-amino-ethyl)furan (Compound 7; in Formula 1 $R_1=R_2=R_3=CH_3CH_2—$, $X=OH$ and $R_4=CH_2NH_2$) or the corresponding trimethylsilyl compound are utilized to make compounds of Formula 11 where $Y_8$ is H, $R_3$, $CO—R_3$, $CO—O—R_3$, $CO—NH—R_3$, $CO—N—(R_3)_2$, $PO(OR_3)_2$ or $PO(OR_3)R_3$, and $R_3$ independently is H, phenyl, substituted phenyl, alkyl of 1 to 20 carbons or is alkyl of 1 to 20 carbons substituted with a hydroxyl, alkoxy, substituted amino, thioalkoxy or with a $COR_3^*$ group where $R_3^*$ is H, lower alkyl, OH, $OR_3^{}$, $NH_2$, $NHR_3^{}$ or $N(R_3^{})_2$ group where $R_3^{}$ independently is H or lower alkyl, with the proviso that when $Y_8$ is $CO—O—R_3$ or is $CO—NH—R_3$ then $R_3$ is not hydrogen; $Y_9$ is H, $R_4$, $CO—R_4$, $CO—O—R_4$, $CO—N$-piperazinyl, $CO—N$-substituted N-piperazinyl, $CO—N$-morpholinyl, $CO—N$-substitutetd N-morpholinyl, $CO—NH—R_4$, or $CO—N(R_4)_2$, $PO(OR_4)_2$, $PO(OR_4)R_4$, $SO_2OR_4$, or $SO_2R_4$, where $R_4$ independently is H, phenyl or substituted phenyl, or alkyl of 1 to 20 carbons, or is alkyl of 1 to 20 carbons substituted with a hydroxyl, alkoxy, substituted amino, thioalkoxy or with a COR$_4$* group where R$_4$* is H, lower alkyl, OH, OR$_4$, NH$_2$, NHR$_4$ or N(R$_4$)$_2$ group where R$_4$ is lower alkyl with the proviso that when Y$_9$ is CO—O—R$_4$ then R$_4$ is not hydrogen, and Y$_{10}$ is H or alkyl of 1 to 20 carbons.

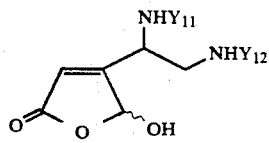

Formula 12

2-Triethylsilyl-4-(1,2-diamino-ethyl)furan (Compound 8; in Formula 1 R$_1$=R$_2$=R$_3$=CH$_3$CH$_2$—, X=NH$_2$ and R$_4$=CH$_2$NH$_2$) or the corresponding trimethylsilyl compound are utilized to make compounds of Formula 12 where Y$_{11}$ and Y$_{12}$ are both independently defined as COR, CONHR, CO$_2$R or SO$_2$R and R is C$_1$-C$_{20}$-alkyl, aryl, aryl-(C$_1$-C$_{20}$-alkyl)-.

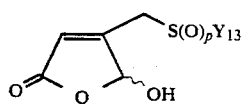

Formula 13

2-Triethylsilyl-4-iodomethylfuran (Compound 9; in Formula 1 R$_1$=R$_2$=R$_3$=CH$_3$CH$_2$—, X=I and R$_4$=H) or the corresponding trimethylsilyl compound are utilized to make compounds of Formula 13 where p is an integer between zero and 2, and Y$_{13}$ is alkyl having 6 to 25 carbon atoms, arylalkyl, aryl, (such as phenyl) substituted aryl, (such as halogen or alkyl substituted phenyl) arylalkyl (such as phenyl (C$_1$-C$_6$ alkyl), substituted arylalkyl, alkenyl containing one or more olephinic bonds and at least 6 carbon atoms, CO—R$_3$, CO—OR$_3$, CONHR$_3$, where R$_3$ is aryl, (such a phenyl or naphthyl) substituted aryl (such as halogen or alkyl substituted phenyl or naphthyl), aralkyl (such as phenyl or (naphthyl C$_1$-C$_6$ alkyl))substituted arylalkyl, alkyl, alkenyl containing one or more olephinic bonds, further Y$_{13}$ is (CH$_2$)$_n$—O—R$_4$, or (CH$_2$)$_n$—O—(CH$_2$-)$_m$—O—R$_4$, where n, and m, are integers and are independently 1 to 25 and R$_4$ is phenyl, substituted phenyl or alkyl of one to 20 carbons, still further Y$_{13}$ is PO(OH)$_2$, PO(OH)OR$_5$, PO(OH)R$_5$, PO(OR$_5$)$_2$, where R$_5$ is independently phenyl, substituted phenyl, alkyl of 1 to 20 carbons or R$_5$ is (CH$_2$)$_n$—N(R$_5$*)$_3$ where R$_5$* is alkyl of 1 to 20 carbons, or Y$_{13}$ is NH—R$_6$ where R$_6$ is phenyl, substituted phenyl or alkyl of at least 6 carbon atoms with the provisos that when p is zero, then Y$_{13}$ is not NH—R$_6$, and when p is 1 or 2 then Y$_{13}$ is not PO(OH)$_2$, PO(OH)OR$_5$, PO(OH)R$_5$ or PO(OR$_5$)$_2$.

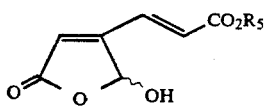

Formula 14

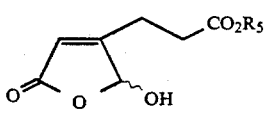

Formula 15

Still speaking generally and by way of general example, the intermediate compounds embraced by Formula 2 can be subjected to hydrogenation, trans-esterification and other reactions involving the ethylenic double bond or ester functionality (which reactions are otherwise known in the art), and can be subjected to oxydation by singlet oxygen to provide, for example, compounds of Formula 14 and of Formula 15. The conditions for oxydation with singlet oxygen are similar or identical to those described in connection with "singlet oxygen oxydation" of the compounds of Formula 1. In Formula 14 and in Formula 15 the symbol R$_5$ is defined as alkyl of 1 to 20 carbons. The compounds of Formula 2 (such as Compound 10) are also used to make Compound 5, which is a starting material for the preparation of compounds of Formula 9.

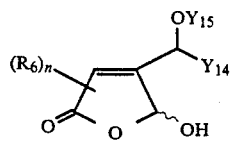

Formula 16

Still further, by way of general example, the intermediate compounds embraced by Formula 3A include an aldehyde function in the 4-position of the furan nucleus. The aldehyde function can be subjected to a Grignard (or like) reaction with a Grignard reagent derived for example from a long chain alkyl halide, and the resulting secondary alcohol (in the side chain of the 4-position of the furan nucleus) may be alkylated, acylated, phosphorylated, reacted with an alkyl, aralkyl or aryl sulfonyl halide, or with an isocyanate to yield a carbamoyloxy group. Similarly, the intermediate compounds of Formula 3B can be alkylated, acylated, phosphorylated, reacted with an alkyl, aralkyl or aryl sulfonylhalide, or with an isocganate. Oxidation by singlet oxygen of these derivatives, derived from the compounds of Formula 3A and 3B is conducted under conditions identical or substantially similar to the conditions described before. The oxidation reaction with singlet oxygen thus provides the examplary compounds of Formula 16 where R$_6$ is phenyl, alkyl of 1 to 6 carbons and n is 1 or 2, and where the R$_6$ group is attached either to the 3 or to the 5 position of the 2(5H)-furanone; or when n is 2 then R$_6$ is attached to both the 3 and 5 positions. Y$_{14}$ is H or an alkyl group, (preferably long chain alkyl), aryl (such as phenyl or naphthyl), substituted aryl (such as halogen or alkyl substituted phenyl or naphthyl) arylalkyl (such as phenyl (C$_1$-C$_6$ alkyl) or naphthyl(C$_1$-C$_6$alkyl)). Y$_{15}$ is defined the same as Y$_1$ in connection with Formula 5.

The synthetic intermediate compounds embraced by Formula 4A are 2-trialkylsilyl-3-furaldehydes. The intermediate compounds embraced by Formula 4B are 2-trialkylsilyl-3-furylmethanols. By way of general example and not by way of limitation, the aldehyde function of the compounds of Formula 4A is reacted in accordance with the invention, with a Grignard (or like) reagent derived for example from a long chain alkyl halide, and the resulting secondary alcohol (in the side chain of the 3-position of the furan nucleus) may be alkylated, acylated, phosphorylated, reacted with an alkyl aralkyl or aryl sulfonyl halide, or with an isocyanate to yield a carbamoyloxy group. The alkylation, acylation, phosphorylation and the other reactions just noted can also be carried out on the primary hydroxyl group of the compounds of Formula 4B. Oxidation by singlet oxygen of these derivatives, derived from the compounds of Formula 4A and 4B is conducted under conditions identical or substantially similar to the conditions described before, and yields 3-substituted 5-hydroxy-2(5H)-furanone derivatives. The latter are reduced, for example with sodium borohydride to yield the 3-substituted 2(5H)-furanone compounds of Formula 17.

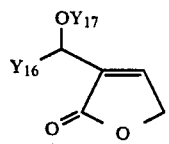

Formula 17

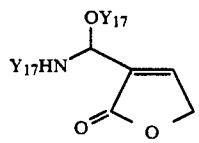

Formula 18

In Formula 17 $Y_{16}$ is H, an alkyl group, (preferably long chain alkyl), aryl (such as phenyl or naphthyl), substituted aryl (such as halogen or alkyl substituted phenyl or naphthyl) arylalkyl (such as phenyl ($C_1$-$C_6$ alkyl) or naphthyl($C_1$-$C_6$alkyl)).

$Y_{17}$ is H, alkyl of 1 to 20 carbons, arylalkyl, (such as phenyl ($C_1$-$C_6$ alkyl) or naphthyl($C_1$-$C_6$alkyl)) aryl, (such as phenyl or naphthyl), substituted aryl (such as halogen or alkyl substituted phenyl or naphthyl), substituted arylalkyl, alkenyl containing one or more olephinic bonds, $PO(OH)_2$, $PO(OH)OR_2$, $PO(OH)R_2$ $PO(OR_2)_2$, where $R_2$ is independently alkyl of 1 to 20 carbons, phenyl, or substituted phenyl, further $Y_{17}$ is $CO—R_3$, $CO—OR_3$, $CONHR_3$, $SO_2R_3$, $SO_2NHR_3$, $(CH_2)_n—O—R_3$, or $(CH_2)_n—O—(CH_2)_m—O—R_3$, where n and m, are integers and are independently 1 to 20 and $R_3$ is H, alkyl, alkenyl containing one or more olephinic bonds, aryl, substituted aryl, arylalkyl or substituted arylalkyl, with the proviso that when $Y_{17}$ is $CO—R_3$, $CO—OR_3$, and $CONHR_3$ then $R_3$ is not hydrogen.

Alternatively, the synthetic intermediate compounds embraced by Formula 4A (2-trialkylsilyl-3-furaldehydes) can also be used for the preparation of compounds shown in Formula 18, which are the "amino" analogs of the compounds of Formula 17. The compounds of Formula 18 can be prepared from the compounds of Formula 4A by replacing the secondary alcohol formed after a Grignard reaction of the compounds of Formula 4, with an amino group. This can be accomplished, for example, by reacting the secondary alcohol (obtained from the Grignard or like reaction) with diphenylphosphoryl azide in the presence of diethyl azidodicarboxylate (DEAD), followed by reduction of the azide function to amino function. The symbols $Y_{16}$ and $Y_{17}$ in Formula 18 signify the same groups as in Formula 17. Generally speaking, the anti-inflammatory compounds made from the synthetic intermediates of Formula 4A are selective inhibitors of calcium$^{2+}$ channel mobilization.

Additional preferred compounds of the invention are 2- methyl-4-phenyl-3-furaldehyde (Compound 16) the corresponding alcohol, 2-methyl-4-phenyl-3-furylmethanol (compound 17) 3-phenyl-4-furaldehyde (Compound 18) and 3-phenyl-4-furylmethanol (Compound 19). The specific examples described below show how compounds 16 through 19 are used as intermediates for the synthesis of furanone compounds having anti-inflammatory utility.

The synthetic chemist will appreciate the compounds of the invention, as well as the biologically active anti-inflammatory compounds which are made from the compounds of the invention, can be made in accordance with the general procedures outlined above, and that the specific conditions described below are illustrative of these procedures and can be generalized to make any and all compounds of the invention, as well as the biologically active compounds derived therefrom.

SPECIFIC EXAMPLES

EXAMPLE 1

1-Trimethylsilyl-4-furaldehyde n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. 48°-50°/0.25 torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) −2.0, 116.2, 128.9, 155.3, 164.1 and 184.5.

HRMS exact mass calculated for $C_8H_{12}O_2Si(M+)$ 168.0607, found 168.0588. See also U.S. Pat. No. 4,935,530, the specification of which is incorporated herein by reference.

4-Hydroxymethyl-2-trimethylsilylfuran

2-Trimethylsilyl-4-furaldehyde (1.57 g, 9.35 mmol) was added to a suspension of sodium borohydride (424 mg, 11.2 mmol) in methanol (10 ml) at 0° C. After 45 minutes, most of the methanol was evaporated and the residue taken up in ethyl ether. The ethyl ether extracts were combined, washed (water), dried (magnesium sulfate) and evaporated to dryness to give an oil, which was purified by flash chromatography on silica using 30% ethyl ether/hexane to give the title alcohol as a pale yellow oil.

$^1$H NMR (CDCl$_3$): 7.57 (s, 1H); 6.64 (s, 1H); 4.50 (s, 2H); 2.75 (broad s, 1H); 0.25 (s, 9H).

$^{13}$C NMR (CDCl$_3$): 161.5, 144.0, 125.0, 119.7, 56.2, −1.8.

HRMS exact mass calculated for $C_8H_{14}O_2Si$: 170.0763, obtained (EI+): 170.0766.

2-Triethylsilyl-4-furaldehyde n-Butyl lithium (a 2.5M solution in hexane; 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethylsilyl-3-furaldehyde as a pale yellow oil, boiling point 85°–90°/0.4 torr.

IR (neat) 1680cm$^{-1}$ $^1$H NMR (CDCl$_3$) 0.79 (q, 6H, J=7.3 Hz), 0.90 (t, 9H, J=7.3 Hz), 7.0 (s, 1H), 8.26 (s, 1H) and 9.95 (s, 1H).

$^{13}$C NMR (CDCL$_3$) 2.9, 7.1, 117.2, 128.8, 155.6, 162.3 and 184.6.

HRMS m/e exact mass calculated for C$_{11}$H$_{18}$O$_2$Si(M$^+$) 210.1076, found 210.1071. See also U.S. Pat. No. 4,935,530, the specification of which is incorporated herein by reference.

4-Hydroxymethyl-2-triethylsilylfuran (Compound 1)

Sodium borohydride (353 mg, 0.93 mmol) was added portionwise to a solution of 2-triethylsilyl-4-furaldehyde (1.64 g, 7.79 mmol) in methanol (10 ml) at 0°. After 1 hour, most of the methanol was evaporated and the residue dissolved in a minimum amount of dilute hydrochloric acid. Extraction (ethyl acetate), drying (magnesium sulfate) and evaporation gave an oil, which was purified by flash chromatography on silica using 20% ethyl ether/hexane. Fractions with R$_f$ of about 0.07 (10% ethyl ether/hexane) gave after evaporation the title alcohol as a colorless oil.

$^1$HNMR (CDCl$_3$) 0.76 (q, 6H, J=7.4 Hz), 0.97 (t, 9H, J=7.5 Hz), 1.45 (t, 1H, J=5.3 Hz), 4.56 (d, 2H, J=5.3 Hz), 6.67 (s, 1H) and 7.62 (s, 1H).

HRMS exact mass calculated for C$_{11}$H$_{20}$SiO$_2$(M$^+$) 212.1233 found 212.1231.

2-(tert-Butyldimethylsilyl)-4-furaldehyde n-Butyl lithium (a 2.5M solution) in hexane; 8.3 ml, 20.8 mmol) was added to a solution of morpholine (1.81 ml, 20 mmol) in tetrahydrofuran (100 ml) at −78° C. under argon. After 20 minutes 3-furaldehyde (1.8 ml, 20.8 mmol) was added. After another 15 minutes, sec-butyl lithium (a 1.3M solution in cyclohexane; 16.8 ml, 21.9 mmol) was added dropwise and stirring continued at −78° C. for 1 hour before a solution of t-butyldimethylsilyl chloride (9.4 g, 62.4 mmol) in tetrahydrofuran (10 ml) was added. Stirring was continued overnight (16 hours) while the cooling bath was allowed to attain room temperature. The solution was poured into ice cold 10% (v/v) hydrochloric acid (40 ml) and after stirring at 0° for 10 minutes, the layers were separated. The aqueous phase was extracted with diethyl ether. All the organic phases were combined, dried (magnesium sulfate) and evaporated to dryness to give a brown oil, which was distilled under high vacuum to give the title aldehyde, boiling point 80°–5°/0.5 torr., m.p. 37-8.

$^1$H NMR (CDCl$_3$) 0.23 (s, 6H), 0.90 (s, 9H), 6.99 (s, 1H), 8.25 (s, 1H) and 9.94 (s, 1H).

$^{13}$C NMR (CDCl$_3$) 16.6, 26.1, 117.3, 128.8, 155.5, 162.7 and 184.5.

HRMS exact mass calculated for C$_{11}$H$_{18}$O$_2$Si (M$^+$) 210.1076, found 210.1075.

4-(Methoxyethoxymethoxymethyl)-2-trimethylsilylfuran

2-Methoxyethoxymethyl chloride (0.11 ml, 0.96 mmol) was added to a solution of 4-hydroxymethyl-2-trimethylsilylfuran, also known as (2-trimethylsilyl-4-furyl)methanol, (162.8 mg, 0.96 mmol) and dimethylaniline (0.13 ml, 0.1 mmol) in dichloromethane (5 ml) at 0°. After stirring at room temperature overnight (ca. 16 hours), the reaction mixture was washed successively with water, dilute hydrochloric acid and water. Evaporation of the dried (magnesium sulfate) dichloromethane layer gave an oil, which was purified by preparative silica TLC (developed with 30% ethyl ether/hexane) to give the title ether as a colorless oil.

$^1$H NMR (CDCl$_3$) 0.27 (s, 9H), 3.44 (s, 3H), 3.62 (m, 2H), 3.76 (m, 2H), 4.51 (s, 2H), 4.79 (s, 2H), 6.67 (s, 1H), and 7.65 (s, 1H). MS m/e (% abundance 258(M$^+$, 23), 182(19), 169(57), 154(72), 153(80), 89(50), 73)100) and 59(33).

4-Methoxyethoxymethoxymethyl)-5-hydroxy-2(5H)-furanone (Compound 20)

A mixture of 4-(methoxyethoxymethoxymethyl)-2-trimethylsilylfuran (106 mg, 0.41 mmol) and Rose Bengal (co. 3.0 mg) in tetrahydrofuran (7 ml) was exposed to singlet oxygen at −78° for 2 hours. The residue, after solvent removal, was purified by chromatography on preparative silica thin layer plates (developed with 40% ethyl acetate/hexane) to give the title furanone as a colorless oil.

$^1$HNMR (CDCl$_3$) 3.43 (s, 3H), 3.61, 3.75 (2 br s, 4H), 4.51 (s, 2H), 4.84 (s, 2H) and 5.30 (br, 1H), 6.11 (s, 1H) and 6.14 (s, 1H).

$^{13}$C NMR (CDCl$_3$) 58.9, 62.7, 67.1, 71.6, 95.9, 97.8, 118.7, 165.3 and 170.6.

4-(dodecylphosphonyloxymethyl)-2-triethylsilylfuran

Dodecylphosphinic dichloride (944 mg, 3.29 mmol) was added to a solution of 4-hydroxymethyl-2-triethylsilylfuran (Compound 1, also known as (2-triethylsilyl-4-furyl)methanol 696.8 mg, 3.29 mmol) and 4-dimethylaminopyridine (403 mg, 3.29 mmol) in tetrahydrofuran (5 ml) at 0°. After stirring at room temperature overnight (15 hours), a solution of potassium hydroxide (235 mg, 3.62 mmol) in water (ca. 3 ml) was added. After 30 minutes, the solution was diluted with water and extracted thoroughly with ethyl acetate. Evaporation of the dried (magnesium sulfate) extracts gave an oil, which was purified by flash chromatography on silica using 40% ethyl ether/hexane to give the title ester as a pale yellow oil. $^1$HNMR (CDCl$_3$) 0.75 (q, 6H, J=8.1 Hz), 0.90 (t, 3H, J=6.9 Hz), 0.99 (t, 9H, J=7.8 Hz), 1.27 (br s, 18H), 1.55 (m, 2H), 1.90 (m, 2H), 4.90 (m, 2H), 6.70 (s, 1H) and 7.68 (s, 1H).

MS m/e (% abundance) 444(M$^+$, 12), 388(100), 335(22), 195(21) and 115(21).

4-(Dodecylohosphonyloxymethyl)-5-hydroxy-2(5H)-furanone (Compound 21)

A mixture of 3-(dodecylphosphonyloxymethyl)-5-triethylsilylfuran (325 mg, 0.73 mmol), Rose Bengal (ca. 5 mg) and water (ca. 0.05 ml) in tetrahydrofuran (10 ml) was exposed to singlet oxygen at 0° C. for 1.5 hours.

The residue, after solvent removal, was purified by chromatography on preparative silica thin layer plates (developed with 5% methanol/dichloromethane) to give the title furanone.

$^1$HNMR (CDCl$_3$) 0.91 (t, 3H, J=6.2 Hz), 1.29 (br s, 16H), 1.40 (m, 2H), 1.65 (br m, 1H), 1.95 (m, 1H), 4.95 (br, 2H), 6.15 (br s, 1H), 6.18 (br s, 1H) and 7.0 (br, 1H).

$^{13}$CNMR (CDCl$_3$) 13.9, 21.9, 22.5, 23.9, 25.7, 28.7, 28.9, 29.2, 29.3, 29.5, 30.2, 30.5, 31.7, 60.8, 97.5, 118.6, 163.3, 163.4 and 170.4.

FABMS (negative ion) 361[(M-H)+, 9] and 249(72).

4-(N-Dodecylcarbamoyloxymethyl)-2-triethylsilylfuran

Potassium bis(trimethylsilyl)amide (a 0.5M solution in toluene; 0.7 ml, 0.36 mmol) was added to a solution of 4-hydroxymethyl-2-triethylsilylfuran (Compound 1, 76.1 mg, 0.36 mmol) in tetrahydrofuran (2 ml) at 0° under argon. After 30 minutes, a solution of dodecylisocynate (151 mg, 0.72 mmol) in tetrahydrofuran (0.5 ml) was added. Stirring was continued overnight (14 hours) while the cooling bath attained room temperature. The reaction mixture was quenched with water and extracted thoroughly with ether. Evaporation of the dried (magnesium sulfate) extracts gave an oil, which was purified by preparative silica TLC (developed with 10% ethyl ether/hexane) to give the title carbonate as a pale yellow oil.

$^1$HNMR (CDCl$_3$) 0.77 (q, 6H, J=8.0 Hz), 0.91 (t, 3H, J=6.9 Hz), 1.00 (t, 9H, J=7.3 Hz), 1.29 (br s, 18H), 1.50 (m, 2H), 3.20 (m, 2H), 4.72 (br, 1H), 5.00 (br s, 2H), 6.69 (s, 1H) and 7.69 (s, 1H).

HRMS exact mass calculated for C$_{24}$H$_{45}$SiNO$_3$(M+) 423.3168, found 423.3164.

4-(N-Dodecylcarbamoyloxymethyl)-5-hydroxy-2(5H)-furanone (Compound 22)

A mixture of 3-(N-dodecylcarbamoyloxymethyl)-5-triethylsilylfuran (80 mg, 0.19 mmol), water (ca, 0.1 ml) and Rose Bengal (ca. 3 mg) in tetrahydrofuran (5 ml) was exposed to singlet oxygen at 0° for 1.5 hours. The residue, after solvent removal, was purified by chromatography on preparative silica thin layer plates (developed with ethyl acetate) to give the title furanone as a colorless oil.

$^1$HNMR (CDCl$_3$) 0.92 (t, 3H, J=6.8 Hz), 1.29 (br s, 20H), 1.55 (br m, 2H), 3.20 (dd, 2H, J=6.3 Hz), 4.95 (br, 1H), 5.20 (br, 1H), 6.07 (br s, 1H) and 6.16 (br s, 1H).

$^{13}$CNMR (CDCl$_3$) 13.8, 22.5, 26.5, 26.8, 29.6, 28.6, 28.7, 28.8, 29.0, 29.1, 29.4, 29.6, 30.0, 31.7, 41.2, 59.4, 97.9, 118.6, 115.9, 164.4 and 170.7.

4-Dodecanoxy-2-triethylsilylfuran

A solution of 4-hydroxymethyl-2-triethylsilylfuran (Compound 1, 160 mg, 0.75 mmol) in tetrahydrofuran (0.5 ml) was added to a suspension of potassium hydride (33 mg, 0.83 mmol) in tetrahydrofuran (1 ml) at room temperature. When all the potassium hydride disappeared, 1-iodododecane (0.37 ml, 1.5 mmol) was added. Stirring was continued for 4 days at room temperature. The reaction mixture was quenched with water. Extraction (ethyl ether) and evaporation of the dried (magnesium sulfate) extracts gave an oil, which was purified by flash chromatography on silica using 5% ethyl ether/hexane. Fractions with R$_f$ of about 0.65 on evaporation gave the titled ether as a pale yellow oil.

$^1$HNMR (CDCl$_3$) 0.76 (q, 6H, J=7.6 Hz), 0.91 (t, 3H, J=6.9 Hz), 1.00 (t, 9H, J=7.3 Hz) 1.29 (br s, 18H), 1.65 (m, 2H), 3.47 (t, 2H, J=6.7 Hz), 4.39 (s, 2H), 6.68 (s, 2H) and 7.63 (s, 1H).

HRMS exact mass calculated for C$_{23}$H$_{44}$O$_2$Si(M+) 380.3111, found 380.3100.

4-(Dodecanoxy)-5-hydroxy-2(5H)-furanone (Compound 23)

A mixture of 4-dodecanoxy-2-triethylsilylfuran (85 mg, 0.22 mmol), water (0.05 ml) and Rose Bengal (ca. 3 mg) in tetrahydrofuran (6 ml) was exposed to singlet oxygen at 0° for 1.5 hours. The residue, after solvent removal, was purified by chromatography on preparative silica plates (20×20 cm, 1000u, developed with 50% ethyl ether/hexane) to give the title furanone as a colorless solid.

$^1$HNMR (CDCl$_3$) 0.92 (t, 3H, J=6.9 Hz), 1.30 (br s, 18H), 1.64 (m, 2H), 3.57 (t, 2H, J=6.6 Hz), 4.37 (br s, 2H), 5.75 (br, 1H), 6.10 (s, 1H) and 6.16 (s, 1H).

$^{13}$C NMR (CDCl$_3$) 14.1, 22.6, 25.9, 29.3, 29.4, 29.5, 29.6, 31.9, 65.7, 71.9, 97.9, 117.9, 166.5 and 171.5.

HRMS exact mass calculated for C$_{17}$H$_{31}$O$_4$(M+H)+ 299.2222, found 299.2204.

Diethyl (2-triethylsilyl-4-furyl)methyl phosphate

A mixture of (2-triethylsilyl-4-furyl)methanol (Compound 1, 2.86 g, 13.5 mmol), triethylamine (3.76 ml, 27.0 mmol) and diethyl chlorophosphate (4.28 ml, 29.0 mmol) in tetrahydrofuran (10 ml) was stirred at room temperature for 14 hours. The mixture was filtered and the filtrate was evaporated to dryness to give a residue, which was redissolved in ethyl ether and washed with 10% hydrochloric acid, water and 5% sodium bicarbonate. Evaporation of the dried (magnesium sulfate) organic phase gave an oil, which was purified by chromatography on a silica column with 30% ethyl acetate/hexane to give the title ester.

IR(CDCl$_3$): 1260 and 1220.

$^1$HNMR (CDCl$_3$): 0.70 (q, 6H, J=7.8 Hz), 0.92 (t, 9H, J=7.8 Hz), 1.24 (t, 6H, J=7.1 Hz), 4.01 (q, 2H, J=6.8 Hz), 4.03 (q, 2H, J-6.8 Hz), 4.90 (s, 1H), 4.93 (s, 1H), 6.66 (s, 1H) and 7.64 (s, 1H).

$^{13}$CNMR (CDCl$_3$): 3.0, 7.1, 15.8, 15.9, 60.6, 60.7, 63.5, 63.6, 120.5, 120.6, 121.0, 145.5 AND 159.7

4-1-(Diethylphosphoryloxy)methyl-5-hydroxy-2(5H)-furanone (Compound 24)

A mixture of diethyl (2-triethylsilyl-4-furyl)methyl phosphate (803 mg, 2.31 mmol), water (2 drops) and Rose Bengal (5 mg) in acetone (50 ml) was exposed to singlet oxygen at 0° for 7 hours. The residue, after solvent removal, was purified by chromatography on a silica column using ethyl acetate to give the title furanone.

IR (CHCl$_3$): 3250, 1770, 1250, 1150, 1050 and 960.

$^1$HNMR (CDCl$_3$): 1.37 (t, 6H, J=6.0 Hz), 4.16 (2q, 4H, J=6.0 Hz), 4.85 (ddd, 1H, J=15.0 Hz, 9.0 Hz, 1.2 Hz); 4.96 (ddd, 1H, J=15.0 Hz, 7.2 Hz; 0.6 Hz), 6.12 (s, 1H) and 6.15 (s, 1H).

$^{13}$CNMR (CDCl$_3$): 62.1, 64.7, 97.4, 118.8, 163.3, 163.4 and 170.4.

4-Dodecoyloxymethyl-2-trimethylsilylfuran

To a stirred solution of 4-hydroxymethyl-2-trimethylsilylfuran (0.288 g., 1.70 mmol) and pyridine (0.214 g., 2.55 mmol) in 30 ml dry tetrahydrofuran at 0 degrees was added lauroyl chloride (0.408 g., 1.86 mmol). This solution was allowed to warm to room temperature, stirred 30 minutes, and partitioned between ethyl ether and 5% sodium bicarbonate solution The organic portion was washed with aqueous cupric sulfate solution, water, saturated sodium chloride solution, dried over magnesium sulfate, filtered and concentrated to a colorless oil. This material was purified by flash chromatography (silica, 5% ethyl ether/petroleum ether) to give the desired ester.

$^1$H NMR (CDCl$_3$): 7.64 (s, 1H); 6.63 (s, 1H); 4.97 (s, 2H); 2.31 (t, J=7.3 Hz, 2H); 1.55 to 1.7 (m, 2H); 1.2 to 1.4 (m, 16H); 0.89 (t, J=6.3 Hz, 3H); 0.25 (s, 9H).

$^{13}$C NMR (CDCl$_3$): 173.5, 161.4, 145.6, 120.3, 57.4, 34.2, 31.8, 29.5, 29.4, 29.3, 29.2, 29.0, 24.9, 22.6, 14.0, −1.8.

m/z Calculated for C$_{20}$H$_{36}$O$_3$Si: 352.2434, obtained (CI+): 352.2448.

4-Dodecoyloxymethyl-5-hydroxy-2(5H)-furanone

A stirred solution of 4-dodecoyloxymethyl-2-trimethylsilylfuran (0.375 g., 1.07 mmol) and Rose Bengal (trace) in 275 ml of acetone was flushed with oxygen and cooled to −78 degrees. The solution was subsequently irradiated with a 300 Watt flood lamp while under constant positive pressure of oxygen until starting material was no longer visible by TLC. The solution was warmed to room temperature and concentrated to a pale, orange solid residue. This material was purified by passing through a small plug of silica (ethyl ether as eluent) to give the desired hydroxybutenolide.

$^1$H NMR (CDCl$_3$): 6.16 (broad s, 1H); 6.05 (broad s, 1H); 5.55 (broad s, 1H); 4.97 (m, 2H); 2.41 (m, 2H); 1.6 to 1.75 (m, 2H); 1.2 to 1.4 (m, 16H); 0.88 (m, 3H).

$^{13}$C NMR (CDCl$_3$): 173.4, 170.4, 163.2, 118.7, 97.6, 58.8, 33.9, 31.9 29.5, 29.4, 29.3, 29.2, 29.1, 24.8, 22.6, 14.1.

m/z Calculated for C$_{17}$H$_{32}$NO$_5$ (M+NH$_4$)+ 330.2280, obtained (CI+): 330.2282.

EXAMPLE 2

(E),(Z)-)-O-Methyl-2-triethylsilyl-4-furaldehyde oxime

A solution of sodium acetate (1 g, 12.3 mmol) and methoxylamine hydrochloride (1.05 g, 12.3 mmol) in water (5 ml) was added to a solution of 2-triethylsilyl-4-furaldehyde (860 mg, 4.1 mmol) in ethanol (6 ml) at room temperature. After stirring for 16 hours, most of the ethanol was evaporated and the residue dissolved in water. Extraction (ethyl acetate) and evaporation of the dried (magnesium sulfate) extracts gave an oil, which was purified by flash chromatography on silica using 5% ethyl ether/hexane to give the title oxime as a colorless oil.

$^1$HNMR (CDCl$_3$) 0.79 (q, 6H, J=7.3 Hz), 0.99 (t, 9H, J=7.9 Hz), 3.95 (s, 3H), 4.06 (s, 3H), 6.84 (s, 1H), 7.00 (s, 1H), 7.28 (s, 1H), 7.82 (s, 1H), 8.05 (s, 1H) and 8.34 (s, 1H).

HRMS exact mass calculated for C$_{12}$H$_{21}$NO$_2$Si(M+) 239.1341, found 239.1332.

4-Aminomethyl-2-triethylsilylfuran (Compound 2)

Lithium aluminum hydride (a 1.0M solution in tetrahydrofuran; 0.54 ml, 0.54 mmol) was added dropwise to a solution of (E), (Z)-O-methyl-2-triethylsilyl-4-furaldehyde oxime (106.2 mg, 0.46 mmol) in tetrahydrofuran (5 ml) at room temperature. After stirring at room temperature overnight (ca. 14 hours), the reaction mixture was quenched with water. Extraction (ethyl ether) and evaporation of the dried (magnesium sulfate) extracts gave an oil, which was purified by flash chromatography on silica using 10% methanol/dichloromethane/1% ammonia. Fractions with R$_f$ of about 0.34 gave after evaporation the title amine as a pale yellow oil.

$^1$H NMR (CDCl$_3$) 0.76 (q, 6H, J=7.9 Hz), 0.98 (t, 9H, J=8.4 Hz), 1.87 (br s, 2H), 3.76 (s, 2H), 6.63 (s, 1H) and 7.56 (s, 1H).

HRMS exact mass calculated for C$_{11}$H$_{21}$SiNO(M+) 211.1392, found 211.1389.

4-(N-Dodecanoylaminomethyl)-2-triethylsilylfuran

Dodecanoyl chloride (109 mg, 0.49 mmol) was added to a solution of 4-aminomethyl-2-triethylsilylfuran (Compound 2, 70 mg, 0.33 mmol) and triethylamine (69 microliter, 0.49 mmol) in tetrahydrofuran (3 ml) at room temperature. After stirring at room temperature overnight (ca. 15 hours), most of the solvent was evaporated and the residue was purified by chromatography on preparative silica thin layer plates (developed with 50% ethyl ether/hexane) to give the title amide as a colorless oil.

$^1$HNMR (CDCl$_3$) 0.75 (q, 6H, J=7.9 Hz), 0.87 (t, 3H, J=6.8 Hz), 0.97 (q, 9H, J=7.9 Hz), 1.24 (br s, 16H), 1.60 (m, 2H), 2.17 (t, 2H, J=7.8 Hz), 4.27 (d, 2H, J=5.3 Hz), 5.65 (br s, 1H), 6.57 (s, 1H) and 7.56 (s, 1H).

HRMS exact mass calculated for C$_{23}$H$_{43}$NO$_2$Si(M+) 393.3063, found 393.3048.

4-(N-Dodecanoylaminomethyl)-5-hydroxy-2(5H)-furanone (Compound 25)

A mixture of 4-(N-dodecanoylaminomethyl)-2-triethylsilylfuran (73.2 mg, 0.18 mmol), water (0.05 ml) and Rose Bengal (ca. 3 mg) in tetrahydrofuran (5 ml) was exposed to singlet oxygen at 0° for 1.5 hours. The residue, after solvent removal, was purified by chromatography on preparative silica thin layer plates (developed with ethyl acetate) to $^1$HNMR (CDCl$_3$) 0.93 (t, 3H, J=6.9 Hz), 1.30 (br s, 16H), 1.65 (br m, 2H), 2.31 (t, 2H, J=7.8 Hz), 4.22 (d, 2H, J=5.0 Hz), 5.93 (s, 1H), 6.11 (s, 1H) and 7.04 (t, 1H, J=5.0 Hz).

$^{13}$CNMR (CD$_3$OD) 14.5, 23.7, 26.9, 30.3, 30.5, 30.6, 30.7, 33.0, 36.8, 37.7, 100.0, 118.1, 168.7, 172.6 and 176.4.

HRMS exact mass calculated for C$_{17}$H$_{30}$NO$_4$(M+H)+ 312.2174, found 312.2182.

4-(N-Dodecylureido)methyl-2-triethylsilylfuran

Dodecylisocyanate (105 mg, 0.49 mmol) was added to a solution of 4-aminomethyl-2-triethylsilylfuran (Compound 2, 70 mg, 0.33 mmol) and triethylamine (69 microliter, 0.49 mmol) in tetrahydrofuran (3 ml) at room temperature. After stirring at room temperature overnight (ca. 16 hours), the reaction mixture was quenched with water. Extraction (ethyl ether) and evaporation of the dried (magnesium sulfate) extracts gave a residue which was purified by flash chromatography on silica using 60% ethyl ether/hexane. Fractions of R$_f$ of about 0.47 on evaporation gave the title urea as an off-white solid.

$^1$HNMR (CDCl$_3$) 0.74 (q, 6H, J=8.0 Hz), 0.87 (t, 3H, J=6.9 Hz), 0.96 (q, 9H, J=7.7 Hz), 1.24 (br s, 18H), 1.40 (m, 2H), 3.15 (q, 2H, J=6.4 Hz), 4.17 (d, 2H), J=5.4 Hz), 4.67 (br t, 1H), 4.85 (br t, 1H), 6.58 (s, 1H) and 7.53 (s, 1H).

HRMS exact mass calculated for C$_{24}$H$_{46}$N$_2$O$_2$Si(M+) 422.3329 found 422.3315.

4-(N-Dodecylureido)methyl-5-hydroxy-2(5H)-furanone (Compound 26)

A mixture of 4-(N-dodecylureido)methyl-2-triethylsilylfuran (80 mg, 0.19 mmol), water (0.01 ml) and Rose Bengal (ca. 3 mg) in tetrahydrofuran (6 ml) was exposed to singlet oxygen at 0° for 1 hour. The residue, after solvent removal, was purified by chromatography on preparative silica thin layer plates (developed with ethyl acetate) to give the title furanone as a colorless solid.

$^1$HNMR (CD$_3$OD) 0.93 (t, 3H, J=7.2 Hz), 1.33 (br s, 18H), 1.50 (br t, 2H), 3.16 (t, 2H, J=6.9 Hz), 4.12 (br s, 2H), 4.91 (s, 2H), 5.91 (br s, 1H) and 6.09 (s, 1H).

$^{13}$CNMR (CD$_3$OD) 14.5, 23.7, 27.9, 30.5, 30.8, 31.0, 31.3, 33.1, 38.6, 41.1, 99.9, 117.6, 160.7, 170.7 and 172.8.

HRMS exact mass calculated for C$_{18}$H$_{33}$N$_2$O$_4$(M+H)$^+$ 341.2440, found 341.2434.

4-(N-Dodecylsulfonamido)methyl-2-triethylsilylfuran

Dodecanesulfonyl chloride (124 mg, 0.46 mmol) was added to a solution of 4-aminomethyl-2-triethylsilylfuran (Compound 2, 81.3 mg, 0.39 mmol) and triethylamine (64 microliter, 0.46 mmol) in tetrahydrofuran (2 ml) was also added. After stirring at room temperature overnight (ca. 18 hours), the reaction mixture was quenched with water. Extraction (ethyl ether) and evaporation of the dried (magnesium sulfate) extracts gave an oil, which was purified by chromatography on preparative silica thin layer plates (developed with 30% ethyl ether/hexane) to give the title sulfonamide as a pale yellow oil.

$^1$HNMR (CDCl$_3$) 0.74 (q, 6H, J=7.9 Hz), 0.88 (t, 3H, J=7.8 Hz), 0.95 (t, 9H, J=7.4 Hz), 1.26 (br s, 18H), 1.75 (m, 2H), 2.94 (m, 2H), 4.17 (d, 2H, J=5.9 Hz), 4.35 (t, 1H, J=5.9 Hz), 6.64 (s, 1H) and 7.63 (s, 1H).

4-(N-Dodecylsulfonamido)-methyl-5-hydroxy-2(5H)-furanone (Compound 27)

A mixture of 4-(N-dodecylsulfonamido)methyl-2-triethylsilylfuran (106 mg, 0.24 mmol), water (0.01 ml) and Rose Bengal (ca. 3 mg) in tetrahydrofuran (6 ml) was exposed to singlet oxygen at 0° for 1.5 hours. The residue, after solvent removal, was purified by chromatography on preparative silica thin layer plates (developed with 50% ethyl acetate/hexane) to give the title furanone as a colorless solid.

$^1$HNMR (CD$_3$OD) 0.95 (t, 3H, J=6.8 Hz), 1.34 (br s, 16H), 1.50 (m, 2H), 1.80 (m, 2H), 3.15 (m, 2H), 4.11 (br s, 2H), 4.92 (br s, 2H), 6.15 (s, 1H) and 6.17 (s, 1H).

$^{13}$CNMR (CD$_3$OD) 14.3, 23.6, 24.6, 29.2, 30.2, 30.4, 30.6, 30.7, 40.9, 53.5, 100.2, 119.3, 168.9 and 172.9.

FABMS 362[(M+H)+,18]

EXAMPLE 3

4-(1-Hydroxytridecyl)-2-trimethylsilylfuran

A mixture of 1-bromododecane (3.45 g, 14 mmol) and magnesium turnings (349 mg, 14.5 mmol) in tetrahydrofuran (10 ml) was refluxed under argon for 1 hour. After cooling to 0 degrees, a solution of 5-bromo-3-furaldehyde (2.42 g, 14 mmol) in tetrahydrofuran (3 ml) was added and conditions maintained for 20 minutes. The mixture was further cooled to −78 degrees and tert-butyl lithium (a 1.7M solution in pentane; 9.77 ml, 1.67 mmol) was added dropwise, followed by chlorotrimethylsilane (5.27 ml, 41.5 mmol) after 20 minutes. Stirring was continued overnight (12 hours) while the cooling bath attained room temperature. The mixture was quenched with saturated aqueous ammonium chloride, diluted with water (15 ml) and extracted with ethyl ether. Evaporation of the dried (magnesium sulfate) extract gave a brown oil, which was flash chromatographed on silica using 15% ethyl ether/petroleum ether. Fractions with R$_f$ of about 0.25 on evaporation afforded the title trimethylsilylfuran as a pale yellow oil.

$^1$H NMR (CDCl$_3$): 0.26 (s, 9H), 0.91 (t, 3H, J=6.7 Hz), 1.29 (broad s, 20H), 1.64 (br, 1H), 1.77 (m, 2H), 4.67 (t, 1H, J=6.8 Hz), 6.65 (s, 1H) and 7.59 (s, 1H).

MS m/e (% abundance) 339 (m$^+$ +1, 9), 338 (31), 170 (35), 169 (100), 75 (15) and 73 (50).

4-(1-Hydroxytridecyl)-5-hydroxy-2(5H)-furanone

A mixture of 4-(1-hydroxytridecyl)-2-trimethyl-silylfuran (271.2 mg, 0.8 mmol) and Rose Bengal (5 mg) in tetrahydrofuran (10 ml) was exposed to singlet oxygen for 2 hours at −78 degrees. The residue, after solvent removal, was flash chromatographed on silica using 70% ethyl ether/petroleum ether. Fractions with R$_f$ of about 0.09 (60% ethyl ether/petroleum ether) on evaporation afforded the captioned furanone as a colorless oil.

$^1$H NMR (CDCl$_3$): 0.91 (t, 3H, J=6.8 Hz), 1.29-1.34 (broad m, 20H), 1.75 (m, 2H), 4.00 (br, 2H, exchanged with D$_2$O), 4.68 (m, 1H), 5.99 (s, 1H), 6.10 (d, 1H, J=7.5 Hz, sharpened into a singlet on D$_2$O exchange), 6.15 (d, 1H, sharpened into a singlet on D$_2$O exchange) and 6.28 (s, 1H).

$^{13}$C NMR (CDCl$_3$): 14.1, 22.7, 25.1 25.1, 25.7, 29.1, 29.3, 29.5, 29.6, 29.6, 29.8, 31.9, 35.3, 35.6, 68.0, 68.2, 97.5, 97.6, 117.6, 118.1, 168.9, 170.4, 170.6 and 170.9.

MS m/e exact mass calculated for C$_{17}$H$_{31}$O$_4$ (M+H)$^+$ 299.2222, found 299.2231.

4-(1-Acetoxytridecyl)-2-trimethylsilylfuran

A mixture of 4-(1-hydroxytridecyl)-2-trimethyl-silylfuran (1.32 g, 3.89 mmol), acetic anhydride (4 ml) and pyridine (6 ml) was stirred under argon at ca. 20 degrees for 16 hours. After most of the solvent was removed under high vacuum (<40 degrees), the residue was dissolved in ethyl ether (40 ml) and washed thoroughly with aqueous copper sulfate and water. Drying (magnesium sulfate) and evaporation gave a brown oil, which was flash chromatographed on silica using 5% ethyl ether/petroleum ether. Fractions with R$_f$ of about 0.55 (10% ethyl ether/petroleum ether) on evaporation gave the desired trimethylsilylfuran as a pale yellow oil.

$^1$H NMR (CDCl$_3$): 0.29 (s, 9H), 0.93 (t, 3H, J=6.8 Hz), 1.30 (broad s, 20H), 1.90 (m, 2H), 2.09 (s, 3H), 5.81 (t, 1H, J=6.8 Hz), 6.63 (s, 1H) and 7.64 (s, 1H).

MS m/e (% abundance) 381 (M$^+$ +1, 13), 380 (42), 346 (11), 339 (28), 338 (100), 321 (29), 320 (17), 183 (23), 170 (36), 169 (29), 154 (26), 153 (11), 117 (27), 75 (23) and 73 (90).

4(1-Acetoxytridecyl)-5-hydroxy-2(5H)-furanone (Compound 28)

A mixture of 4-(1-acetoxytridecyl)-2-trimethylsilylfuran (314.2 mg, 0.83 mmol) and Rose Bengal (5 mg) in tetrahydrofuran (7 ml) was exposed to singlet oxygen for 2.5 hours at −78 degrees. The residue, after solvent removal, was flash chromatographed on silica using 45% ethyl ether/petroleum ether. Fractions with R$_f$ of about 0.21 (60% ethyl ether/petroleum ether) on evaporation afforded the 4-(1-acetoxytridecyl)-5-hydroxy-2(5H)-furanone as colorless prisms: mp 67-68 degrees.

$^1$H NMR (CDCl$_3$): 0.88 (t, 3H, J=7.5 Hz), 1.26 (broad s, 20H), 1.82 (m, 2H), 2.11 (s, 3H), 2.14 (s, 3H), 4.06 (broad d, 1H, exchanged with D$_2$O), 4.86 (broad d, 1H, exchanged with D$_2$O), 5.36 (t, 1H, J=5.6 Hz), 5.50 (t, 1H, J=5.6 Hz), 5.95 (s, 1H), 5.99 (s, 1H), 6.00 (d, 1H, J=10 Hz) and 6.19 (d, 1H, J=7.5 Hz).

$^{13}$C NMR (CDCl$_3$): 14.1, 20.8, 22.7, 25.0, 25.1, 29.2, 29.3, 29.3, 29.5, 31.9, 33.0, 33.2, 69.2, 69.8, 98.0, 118.5, 119.2, 167.1, 169.8, 170.7 and 171.2.

MS m/e: exact mass calculated for C$_{19}$H$_{36}$O$_5$N (M+HN$_4$)+ 358.2593, found 358.2597.

4-(1-Methoxytridecyl)-2-trimethylsilylfuran

A mixture of 4-(1-hydroxytridecyl)-2-trimethylsilylfuran (318.5 mg, 0.9 mmol), sodium hydride (60% dispersion in oil; 150 mg, 3.8 mmol) and iodomethane (0.29 ml, 4.7 mmol) in tetrahydrofuran (7 ml) was refluxed for 16 hours. On cooling, the mixture was diluted with ethyl ether (20 ml), quenched with methanol (2 ml) and washed with water. Evaporation of the dried (magnesium sulfate) organic phase gave a deep yellow oil, identified as 4-(1-methoxytridecyl)-2-trimethylsilylfuran.

$^1$H NMR (CDCl$_3$): 0.32 (s, 9H), 0.94 (t, 3H, J=7.1 Hz), 1.31 (broad s, 20H), 1.65 (m, 1H), 1.85 (m, 1H), 3.28 (s, 1H), 4.14 (t, 1H, J=10 Hz); 6.63 (s, 1H) and 7.58 (s, 1H). The product was used directly in the next stage without further purification.

1-Methoxytridecyl)-5-hydroxy-2(5H)-furanone

A mixture of 4-(1-methoxytridecyl)-2-trimethylsilylfuran (280 mg, 0.8 mmol) and Rose Bengal (5 mg) in tetrahydrofuran (7 ml) was exposed to singlet oxygen for 5 hours at −78 degrees. The residue, after solvent removal, was flash chromatographed on silica using 60% ethyl ether/petroleum ether. Fractions with R$_f$ of about 0.21 on evaporation afforded the 4-(1-methoxytridecyl)-5-hydroxy-2(5H)-furanone as a colorless prism: mp 53-54 degrees.

$^1$H NMR (CDCl$_3$): 0.99 (t, 3H, J=8.3 Hz), 1.28 (broad s, 20H), 1.75 (m, 2H), 3.40 (s, 3H), 3.41 (s, 3H), 4.10 (m, 1H), 4.30 (br, 1H), 6.04 (s, 1H), 6.05 (s, 1H), 6.08 (s, 1H), and 6.19 (s, 1H).

$^{13}$C NMR (CDCl$_3$): 14.2, 22.7, 25.0, 25.1, 29.4, 29.5, 29.5, 29.6, 29.7, 29.9, 32.0, 32.9, 33.8, 57.6, 57.9, 97.1, 97.8, 118.5, 119.7 and 168.6.

MS m/e: exact mass cald for C$_{18}$H$_{33}$O$_4$ (M+H)+ 313.2379, found 313.2381.

4-[1-(4-Phenylbutanoyloxy)tridecyl]2-trimethylsilylfuran tert-Butyl lithium (a 1.7M solution in pentane; 0.47 ml, 0.79 mmol) was added dropwise to a solution of 4-(1-hydroxytridecyl)-2-trimethylsilylfuran (256.4 mg, 0.76 mmol), prepared as in Example 38, in tetrahydrofuran (5 ml) at −78 degrees under argon. After 10 minutes, a solution of 4-phenylbutyryl chloride (145 mg, 0.79 mmol) was added. Stirring was continued at room temperature for 2 days and the mixture was quenched with water. Extraction and evaporation of the dried (magnesium sulphate) extracts gave an oil, which was purified by preparative thin-layer chromatography (20×20 cm, 1000 micron silica plate; developed with 10% ethyl ether/hexane). The title ester was obtained as a light yellow oil.

$^1$H NMR (CDCl$_3$): 0.28 (s, 9H), 0.91 (t, 3H, J=7.0 Hz), 1.28 (m, 20H), 1.85 (m, 2H), 1.97 (p, 2H, J=7.7 Hz), 2.35 (t, 2H, J=7.4 Hz), 2.65 (t, 2H, J=7.8 Hz), 5.82 (t, 1H, J=6.9 Hz), 6.61 (s, 1H), 7.25 (m, 2H) and 7.62 (s, 1H).

MS m/e (% abundance 485 (M+, 7) 339 (28), 321 (32), 170 (12), 154 (19), 153 (18), 147 (84), 91 (46) and 73 (100).

4-[1-(4-Phenylbutanoyloxy)tridecyl]-5-hydroxy-2(5H)-furanone

A mixture of 4-[1-(4-phenylbutanoyloxy)tridecyl]-2-trimethylsilylfuran (203 mg, 0.42 mmol) and Rose Bengal (5 mg) in tetrahydrofuran (7 ml) was exposed to singlet oxygen at −78 degrees for 100 minutes. The residue, after solvent removal, was purified by preparative TLC (20×20 cm, 500 micron silica plate; developed with 60% ethyl ether/hexane). The title furanone was isolated as a colorless oil.

$^1$H NMR (CDCl$_3$): 0.93 (t, 3H, J=6.4 Hz), 1.30 (brs, 20H), 1.95 (br, 2H), 2.03 (p, 2H, J=7.5 Hz), 2.43 (t, 2H, J=7.3 Hz), 2.71 (t, 2H, J=7.4 Hz), 5.45 (br, 1H), 5.99 (brs, 1H), 6.05 (brs, 1H), 5.25 (br, 1H), 6.20 (br, 1H) and 7.30 (m, 5H).

$^{13}$C NMR (CDCl$_3$): 14.1, 22.7, 25.0, 26.2, 29.1, 29.3, 29.5, 29.6, 31.9, 33.2, 33.4, 35.0, 69.0, 69.6, 98.0, 118.5, 119.1, 126.2, 128.4, 140.9, 167.2, 169.7 and 173.6.

MS m/e: exact mass calculated for C$_{27}$H$_{44}$NO$_5$ (M+NH$_4$))+ 462.3219, found 462.3220.

4-1-(3-Phenylpropanoyloxy(tridecyl]-2-trimethylsilylfuran tert-Butyl lithium (a 1.7M solution in pentane; 0.25 ml, 0.42 mmol) was added dropwise to a solution of 4-(1-hydroxytridecyl)-2-trimethylsilylfuran (118 mg, 0.35 mmol) in tetrahydrofuran (6 ml) at −78 degrees under argon. After 25 minutes, a solution of hydrocinnamoyl chloride (62.2 microliter, 0.42 mmol) in tetrahydrofuran (½ ml) was added. Stirring was continued at room temperature for 7 hours and quenched with water. Extraction (ethyl ether) and evaporation of the dried (magnesium sulphate) extracts gave an oil, which was purified by preparative TLC (20×20 cm, 500 micron, silica plate; developed with 60% ethyl ether/hexane). The title ester was obtained as a colorless oil.

$^1$H NMR (CDCl$_3$): 0.27 (s, 9H), 0.93 (t, 3H), 1.27 (brs, 20H), 1.85 (m, 2H), 2.65 (t, 2H, J=6.9 Hz), 2.96 (2H, t, J=6.9 Hz), 5.80 (t, 1H, J=7.5 Hz), 6.57 (s, 1H), 7.17-7.32 (m, 5H) and 7.57 (s, 1H).

MS m/e (%abundance) 456 (M+, 8) 338 (30), 321 (15), 247 (5), 193 (9), 153 (17), 91 (56) and 73 (100).

4-1-(3-Phenylpropanoyloxy)tridecyl]-5-hydroxy-2(5H)-furanone

A mixture of 4-[1-3-phenylpropanoyloxy)tridecyl]-2-trimethylsilylfuran (70 mg, 0.15 mmol) and Rose Bengal (5 mg) in tetrahydrofuran (7 ml) was exposed to singlet oxygen at −78 degrees for 80 minutes. The residue, after solvent removal, was purified by preparative TLC (20×20 cm, 500u silica plate; developed with 60% ethyl ether/hexane). The title furanone was isolated as a light yellow oil.

$^1$H NMR (mixture of diasteriomers) (CDCl$_3$): 0.87 (t, 3H, J=6.9 Hz), 1.26 (brs, 20H), 1.72 (m, 2H), 2.73 (brt, 2H), 2.97 (t, 2H, J=7.2 Hz), 4.77 (br, 1H), 5.30 (brt, 1H), 5.48 (brt, 1H), 5.65 (s, 1H), 5.85 (s, 1H), 5.90 (s, 1H), 5.95 (s, 1H) and 7.25 (m, 5H).

$^{13}$C NMR (mixture of diasteriomers) (CDCl$_3$): 14.1, 22.7, 24.8, 25.9, 28.9, 29.1, 29.3, 29.5, 30.6, 30.8, 31.7, 31.8, 31.9, 32.7, 32.9, 33.1, 35.3, 35.4, 35.6, 53.3, 69.7, 97.9, 118.5, 126.7, 128.2, 128.6, 139.8, 166.8 and 169.7.

MS m/e: exact mass calculated for C$_{26}$H$_{42}$NO$_5$ (M+NH$_4$) 448.3062, found 448.3052.

4-[1-(Phenylacetoxy)tridecyl]-2-trimethylsilylfuran tert-Butyl lithium (a 1.7M solution in pentane; 0.29 ml, 0.49 mmol) was added dropwise to a solution of 4-(1-hydroxytridecyl)-2-trimethylsilylfuran (138.2 mg, 0.41 mmol) in tetrahydrofuran (7 ml) at −78 degrees under argon. After 25 minutes, a solution of phenylacetyl chloride (65 microliter, 0.49 mmol) in tetrahydrofuran (½ ml) was added. Stirring was continued at room temperature for 16 hours and quenched with water. Extraction (ethyl ether) and evaporation of the dried (magnesium sulphate) extracts gave an oil, which was purified by preparative TLC (20×20 cm, 500 micron silica plate; developed with 10% ethyl ether/hexane). The title ester was obtained as a pale yellow oil.

$^1$H NMR (CDCl$_3$): 0.25 (s, 9H), 0.89 (t, 3H, J=7.0 Hz), 1.27 (brs, 20H), 1.85 (m, 2H), 3.75 (dd, 2H), 5.80 (m, 1H), 6.52 (2s, 2H), 7.20 (m, 5H), 7.52 (s, 1H) and 7.54 (s, 1H).

MS m/e (% abundance) 456 (M+, 8), 338 (30), 321 (15), 247 (5), 193 (9), 153 (17), 91 (56) and 73 (100).

4-1-(Phenylacetoxy)tridecyl]-5-hydroxy-2(5H)-furanone

A mixture of 4-[1-(phenylacetoxy)tridecyl]-2-trimethylsilylfuran (60 mg, 0.13 mmol) and Rose Bengal (5 mg) in tetrahydrofuran (5 ml) was exposed to singlet oxygen at −78 degrees for 2 hours. The residue, after solvent removal, was purified by preparative TLC (20×20 cm, 500u silica plate; developed with 60% ethyl ether/hexane). The title furanone was isolated as a yellow oil.

$^1$H NMR (mixture of diasteriomers) (CDCl$_3$): 0.91 (t, 3H, J=6.3 Hz), 1.28 (brs, 20H), 1.85 (m, 2H), 3.65 (brs, 2H), 5.40–6.20 (m, 4H) and 7.40 (m, 5H).

$^{13}$C NMR (mixture of diasteriomers) (CDCl$_3$): 14.1, 22.7, 24.5, 24.7, 24.9, 28.8, 29.1, 29.3, 29.5, 29.6, 31.9, 32.9 33.1, 33.2, 41.4, 43.6, 48.5, 53.4, 69.5, 70.0, 70.1, 97.3, 97.7, 97.8, 118.4, 119.2, 126.0, 126.1, 126.3, 126.9, 127.1, 127.2, 127.5, 127.6, 128.3, 128.5, 128.7, 128.8, 129.0, 129.2 129.4, 129.5, 129.8, 129.9, 130.0, 131.3, 166.7, 169.5 and 171.6.

MS m/e: exact mass calculated for C$_{25}$H$_{40}$NO$_5$ (M+NH$_4$)+ 434.2906, found 434.2914.

4-[1-(Cyclohexanoyloxy)tridecyl]-2-trimethylsilylfuran tert-Butyl lithium (a 1.7M solution in pentane; 0.33 ml, 0.55 mmol) was added dropwise to a solution of 4-(1-hydroxytridecyl)-2-trimethylsilylfuran (170 mg, 0.50 mmol) in tetrahydrofuran (5 ml) at 0 degrees under argon. After 10 minutes, cyclohexanecarboxylic acid chloride (74 microliter, 0.55 mmol) was added. The mixture was stirred at room temperature for 15 hours and quenched with water. Extraction and evaporation of the dried (magnesium sulphate) extracts gave an oil, which was purified by preparative TLC (20×20 cm, 1000u silica plate; developed with 5% ethyl ether/hexane). The title ester was obtained as a pale yellow oil.

$^1$H NMR (CDCl$_3$): 0.23 (s, 9H), 0.94 (t, 3H, J=6.9 Hz), 1.31 (br, 20H), 1.21 (m, 12H), 2.35 (tt, 1H, J=11.3 Hz, 3.7 Hz), 5.82 (t, 1H, J=7.5 Hz), 6.61 (s, 1H), and 7.62 (s, 1H).

MS m/e (% abundance 448 (M+, 12), 339 (18), 338 (67), 337 (20), 185 (12), 170 (10), 154 (13), 153 (13), 111 (33), 84 (11), 83 (100) and 73 (71).

4-[1-(Cyclohexanoyloxy)tridecyl]-5-hydroxy-2(5H)-furanone

A mixture of 4-[1-(cyclohexanoyloxy)tridecyl]-2-trimethylsilylfuran (70 mg, 0.16 mmol) and Rose Bengal (5 mg) in tetrahydrofuran (6 ml) was exposed to singlet oxygen at −78 degrees for 2 hours. The residue, after solvent removal, was purified by preparative TLC (20×20 cm, 1000u silica plate; developed with 60% ethyl ether/hexane). The title furanone was obtained as a colorless oil.

$^1$H NMR (CDCl$_3$): 0.91 (t, 3H, J=6.8 Hz), 1.29 (m, 6H), 1.70–2.00 (m, 6H), 2.40 (m, 1H), 5.45 (br, 2H), 5.98 (br, 1H) and 6.05 (br, 1H).

$^{13}$C NMR (CDCl$_3$): 14.1, 22.7, 25.1, 25.3, 25.6, 28.8, 28.9, 29.2, 29.4, 29.5, 29.7, 31.9, 33.3, 43.1, 68.7, 69.3, 98.1, 118.3, 119.0 and 167.6.

MS m/e: exact mass calculated for C$_{24}$H$_{41}$O$_5$ (M+H)+ 409.2953, found 409.2971.

4-[1-(Dodecanoyloxy)tridecyl]2-trimethylsilylfuran tert-Butyl lithium (a 1.7M solution in pentane; 0.21 ml, 0.36 mmol) was added dropwise to a solution of 4-(1-hydroxytridecyl)-2-trimethylsilylfuran (124.5 mg, 0.37 mmol) in tetrahydrofuran (5 ml) at 0 degrees under argon. After 5 minutes, the cooling bath was removed and lauroyl chloride (88 microliter) was added. The mixture was stirred at room temperature for 16 hours and quenched with water. Extraction (ethyl ether) and evaporation of the dried (magnesium sulphate) extracts gave an oil, which was purified by preparative TLC (20×20 cm, 1000u silica plate; developed with 5% ethyl ether/hexane). The title ester was obtained as a colorless oil.

$^1$H NMR (CDCl$_3$): 0.23 (s, 9H), 0.88 (t, 3H, J=6.9 Hz), 1.25 (brs, 36H), 1.57–1.92 (m, 2H), 2.29 (t, 2H, J=7.2 Hz), 5.77 (t, 1H, J=7.5 Hz), 6.57 (s, 1H) and 7.57 (s, 1H).

MS m/e (% abundance) 520 (M+, 9), 338 (45), 320 (18), 257 (10), 183 (16), 170 (10), 154 (25), 73 (100).

4-1-(Dodecanoyloxy)tridecyl]-5-hydroxy-2(5H)-furanone

A mixture of 4-[1-dodecanoyloxy)tridecyl]-2-trimethylsilylfuran (55 mg, 0.11 mmol) and Rose Bengal (5 mg) in tetrahydrofuran (7 ml) was exposed to singlet oxygen at −78 degrees for 2 hours. The residue, after solvent removal, was purified by preparative TLC (20×20 cm, 500u silica plate; developed with 60% ether/hexane). The title furanone was obtained as a colorless oil.

$^1$H NMR (CDCl$_3$): 0.92 (t, 6H, J=6.4 Hz), 1.29 (brs, 38H), 1.60–1.90 (m, 2H), 2.40 (t, 2H, J=7.4 Hz), 5.40 (br, 1H) and 6.02 (br, 2H).

$^{13}$C NMR (mixture of diasteriomers) (CDCl$_3$): 14.0, 14.1, 15.2, 22.7, 24.7, 24.9, 25.0, 25.4, 25.6, 27.9, 28.1, 28.2, 28.3, 28.5, 28.6, 28.7, 28.8, 28.9, 29.1, 29.3, 29.5, 29.6, 30.0, 30.2, 30.4, 30.5, 31.9, 33.1, 34.2, 34.3, 53.4, 65.9, 868.0, 69.3, 69.4, 69.5, 98.0, 118.3, 167.0, 170.0 and 173.5.

MS m/e: exact mass calculated for C$_{29}$H$_{53}$O$_5$ (M+H)+ 481.3893, found 481.3895.

4-[1-(Methylcarbamoyl)tridecyl]-2-trimethylsilylfuran tert-Butyl lithium (a 1.7M solution in pentane; 0.21 ml, 0.36 mmol) was added dropwise to a solution of 4-(1-hydroxytridecyl)-2-trimethylsilylfuran (110 mg, 0.33 mmol) in tetrahydrofuran (5 ml) at 0 degrees under argon. After 10 minutes, a solution of methyl isocyanate (21 microliter, 0.36 mmol) in tetrahydrofuran ($\frac{1}{2}$ ml) was added. Stirring was continued at room temperature for 2 days and the mixture was quenched with water. Extraction (ethyl ether) and evaporation of the dried (magnesium sulphate) extracts gave an oil which was purified by preparative TLC (20×20 cm, 1000u silica plate; developed with 20% ethyl ether/hexane). The title carbamate was obtained as a yellow oil.

$^1$H NMR (CDCl$_3$): 0.27 (s, 9H), 0.91 (t, 3H, J=6.9 Hz), 1.28 (brs, 20H), 1.85 (m, 2H), 2.81 (d, 3H, J=4.9 Hz), 4.60 (br, 1H), 5.70 (t, 1H, J=7.5 Hz), 6.61 (s, 1H) and 7.62 (s, 1H).

MS m/e (% abundance) 395 (M+, 3), 339 (19), 338 (71), 320 (16), 183 (17), 169 (15), 154 (25), 132 (11), 75 (25) and 73 (100).

4-[1-(Methylcarbamoyl)tridecyl]-5-hydroxy-2(5H)-furanone

A mixture of 4-[1-(methylcarbamoyl)tridecyl]-2-trimethylsilylfuran (12.5 mg, 0.03 mmol) and Rose Bengal (2 mg) in tetrahydrofuran (5 ml) was exposed to singlet oxygen at −78 degrees for 80 minutes. The residue, after solvent removal, was purified by preparative TLC (20×20 cm, 250u silica plate; developed with 70% ethyl ether/hexane). The title furanone was obtained as a pale yellow oil.

$^1$H NMR (mixture of diasteriomers) (CDCl$_3$): 0.91 (t, 3H, J=6.8 Hz), 1.29 (brs, 20H), 1.80 (m, 2H), 2.83 (d, 3H, J=4.9 Hz), 2.90 (d, 3H, J=4.9 Hz), 4.80 (br, 1H), 4.95 (bd, 1H), 5.25 (brt, 1H), 5.45 (brt, 1H), 6.01 (brs, 1H) and 6.04 (brs, 1H).

$^{13}$C NMR (mixture of diasteriomers) (CDCl$_3$): 14.1, 22.7, 25.1, 27.6, 29.2 29.4, 29.5, 29.6, 31.9, 33.2, 33.7, 69.7, 69.9, 97.9, 98.5, 118.4, 118.9, 156.7, 168.4 and 169.9.

MS m/e exact mass calculated for C$_{19}$H$_{33}$NO$_5$ (M+NH$_4$)+ 373.2702, found 373.2711.

4-[1-((R)-(+)-a-Methylbenzylcarbamoyl)tridecyl]-2-trimethylsilylfuran tert-Butyl lithium (a 1.7M solution in pentane; 0.59 ml, 1.0 mmol) was added dropwise to a solution of 4-(1-hydroxytridecyl)-2-trimethylsilylfuran (335.5 mg, 0.99 mmol) in tetrahydrofuran (6 ml) at 0 degrees under argon. After 20 minutes, a solution of (R)-(+)-alpha-methylbenzyl isocyanate (146 mg, 0.99 mmol) in THF ($\frac{1}{2}$ ml) was added. Stirring was continued for 16 hours while the cooling bath attained room temperature. The mixture was quenched with water and extracted with ethyl ether. Evaporation of the dried (magnesium sulphate) extracts gave an oil, which was purified by preparative TLC (20×20 cm, two 1000u silica plates; developed with 20% ethyl ether/hexane). The title carbamate was obtained as a light yellow oil.

$^1$H NMR (CDCl$_3$): 0.30 (2s, 9H), 0.92 (brt, 3H), 1.29 (brs, 28H), 1.80 (br, 2H), 4.85–5.00 (2 brs, 2H), 5.68 (t, 1H, J=7.5 Hz), 6.60 (s, 1H), 6.70 (s, 1H), and 7.30 (m, 5H).

MS m/e (% abundance) 503 0.1), 485 (M+NH$_4$+, 0.1), 485 (M+, 0.2), 442 (1), 322 (33), 321 (100), 320 (4), 238 (4), 183 (5), 122 (8) and 106 (4).

4-[1-((R)-(+)-alpha-Methylbenzylcarbamoyl)tridecyl]-5-hydroxy-2(5H)-furanone A mixture of 4-[1-((R)-(+)-alpha-methylbenzylcarbamoyl)tridecyl]-2-trimethylsilylfuran (71 mg, 0.15 mmol) and Rose Bengal (5 mg) in tetrahydrofuran (5 ml) was exposed to singlet oxygen at −78 degrees for 2 hours. The residue, after solvent removal, was purified by preparative TLC (20×20 cm, 500u silica plate; developed with 60% ethyl ether/hexane) The title furanone was obtained as a pale yellow oil.

$^1$H NMR (mixture of diasteriomers) (CDCl$_3$): 0.91 (t, 3H, J=7.0 Hz), 1.28 (brs, 18H), 1.38 (d, 3H, J=7.0 Hz), 1.50 (m, 2H), 1.78 (m, 2H), 4.80 (br, m, 1H), 5.26 (m, 1H), 5.38 (m, 1H), 5.98 (brs, 1H), 6.05 (brs, 1H) and 7.35 (m, 5H).

$^{13}$C NMR (mixture of diasteriomers) 14.1, 15.3, 17.9, 22.1, 22.3, 22.7, 25.0, 29.0, 29.1, 29.3, 29.5, 29.6, 31.9, 33.2, 3.34, 33.6, 51.0, 63.8, 69.8, 69.9, 97.9, 98.3, 98.4, 104.2, 118.3, 118.4, 118.8, 125.7, 125.8, 125.9, 127.7, 128.8, 142.7, 155.3, 161.8, 169.8 and 169.9.

MS m/e: exact mass calculated for C$_{25}$H$_{36}$NO$_5$ (M+—CH$_3$): 430.2593, found 430.2603.

4-(1-Trichloroacetoxy)tridecyl-2-trimethylsilylfuran tert-Butyl lithium (a 1.7M solution in pentane; 0.32 ml, 0.54 mmol) was added dropwise to a solution of 4-(1-hydroxytridecyl)-2-trimethylsilylfuran (151.3 mg, 0.45 mmol) in tetrahydrofuran (10ml) at 0 degrees under argon. After 10 with ethyl ether. Evaporation of the dried (magnesium sulphate) extracts afforded an oil, which was purified by preparative TLC (20×20 cm, 500u silica plate; developed with 10% ethyl ether/petroleum ether). The title ester was obtained as a pale yellow oil.

$^1$H NMR (CDCl$_3$): 0.28 (s, 9H), 0.91 (t, 3H, J=6.0 Hz), 1.28 (brs, 20H), 2.0 (m, 2H), 5.88 (t, 1H, J=7.5 Hz), 6.64 (s, 1H) and 7.70 (s, 1H).

MS m/e (% abundance) 460/462/464 ((M+NH$_4$)+, 16, 16, 5), 426 (13), 316 (21), 300 (69), 299 (21) and 298 (100).

4-(1-Trichloroacetoxy)tridecyl-5-hydroxy-2(5H)-furanone

A mixture of 4-(1-trichloroacetoxy)tridecyl-2trimethylsilylfuran (120 mg, 0.25 mmol) and Rose Bengal (5 mg) in tetrahydrofuran (5 mg) was exposed to singlet oxygen at −78 degrees for $\frac{1}{2}$ hour. The residue, after solvent removal, was purified by preparative TLC (20×20 cm, 500u silica plate; developed with 60% ethyl ether/hexane). The title furanone was obtained as a light yellow oil.

$^1$H NMR (CDCl$_3$): 0.92 (t, 3H, J=7.0 Hz), 1.29 (brs, 20H), 2.02 (br, 2H), 5.75 (br, 1H), 6.18 (brs+s, 2H).

$^{13}$C NMR (CDCl$_3$): 14.1, 22.7, 24.6, 28.8, 29.0, 29.3, 29.4, 29.5, 29.6, 29.9, 31.7, 31.9, 32.7, 74.6, 89.5, 97.6, 119.1, 161.1, 164.5 and 169.8.

MS m/e: exact mass calculated for C$_{19}$H$_{33}$C$_{13}$NO$_5$ (M+NH$_4$)+ 460.1424, found 460.1403.

4-(1-Hydroxytridecyl)-2-triethylsilylfuran

Dodecylmagnesium bromide (a 1M solution in tetrahydrofuran: 14.3 ml, 14.3 mmol) was added dropwise to a solution of 2-triethylsilyl-4-furaldehyde (2.0 g, 9.52 mmol) in THF (20 ml) at 0 degrees C. under argon. After stirring at room temperature for 2 hours, the mixture was quenched with dilute HCl and extracted with ethyl ether. Evaporation of the dried (magnesium sulfate) extracts gave an oil, which was purified by flash chromatography on silica using 30% ethyl ether/hexane to give the titled alcohol.

$^1$H NMR (CDCl$_3$) 0.76 (q, 6H, J=8.0 Hz), 0.88 (t, 3H, J=6.3 Hz). 0.98 (t, 9H, J=8.0 Hz), 1.25 (m, 20H) 1,62 (d, 1H, J=4.3 Hz). 1.75 (m, 2H), 4.63 (dd, 1H, J=6.6 Hz, 1.9 Hz), 6.63 (s, 1H) and 7.57 (s, 1H).

EXAMPLE 4

3-(1-Chlorotridecyl)-5-trimethylsilylfuran

Triethylamine (0.55 ml, 3.95 mmol), followed by oxalyl chloride (0.34 ml, 3.95 mmol) was added dropwise to a solution of 3-(1-hydroxytridecyl)-5-trimethylsilylfuran (890 mg. 2.63 mmol) in anhydrous dichloromethane (10 ml) at 0 degrees. After 40 minutes, the reaction was quenched with ice water. Extraction (dichloromethane) and evaporation of the dried (magnesium sulfate) extracts gave an oil, which was purified by flash chromatography on silica using 5% ethyl ether/hexane. Fractions with R$_f$ of about 0.37 on evaporation gave the title chloride as a pale yellow oil, solidified to a colorless solid on storage at −20 degrees.

$^1$H NMR (CDCl$_3$): 0.26 (s, 9H), 0.89 (t, 3H, J=6.3 Hz), 1.26 (brs, 20H), 1.85-2.05 (2m, 2H), 5.87 (t, 1H, J=7.5 Hz), 6.63 (d, 1H, J=2.3 Hz) and 7.66 (d, 1H, J=2.4 Hz)

MS m/e (% abundance): 321 (M$^+$−Cl, 57), 180 (14), 154 (43), 153 (16), 75 (13) and 73 (100).

3-(1-Azidotridecyl)-5-trimethylsilylfuran

A mixture of 3(1-chlorotridecyl)-5-trimethylsilylfuran (468 mg, 1.31 mmol) and sodium azide (852 mg, 13.1 mmol) in dry dimethylformamide (2 ml) was stirred at 60 degrees for 6 days. Most of the solvent was evaporated under high vacuum and the residue dissolved in water. Extraction (ethyl ether) and evaporation of the dried (magnesium sulfate) extracts gave an oil, which was flash chromatographed on silica using 5% ethyl ether/hexane. Fractions with R$_f$ of about 0.73 on evaporation gave the title azide as a very pale yellow oil.

IR neat): 2100 (br, s), 1080

$^1$H NMR (CDCl$_3$): 0.26 (s, 9H), 0.88 (t, 3H, J=6.3 Hz), 1.25 (brs, 20H), 1.75 (m, 2H), 4.33 (t, 1H, J=7.3 Hz), 6.58 (s, 1H) and 7.59 (s, 1H).

MS m/e: Exact mass calculated for C$_{20}$H$_{37}$N$_3$O$_5$ 363.2705, found 363.2698.

3-(1-Aminotridecyl)-5-trimethylsilylfuran

Lithium aluminum hydride (a 1M solution in tetrahydrofuran; 1.1 ml, 1.1 mmol) was added dropwise to a solution of 3-(1-azidotridecyl)-5-trimethylsilylfuran (334 mg, 0.92 mmol) in tetrahydrofuran at room temperature. After one hour at room temperature, the excess hydride was destroyed by adding acetone slowly to the mixture with cooling. Sodium sulfate (ca. 0.5 g) was added and the mixture was extracted thoroughly with ethyl acetate. Evaporation of the dried (magnesium sulfate) extracts gave an oil, which was purified by flash chromatography on silica using 5% methanol/dichloromethane containing 0.2% triethylamine. Fractions with R$_f$ of about 0.18 on evaporation gave the title amine as a pale yellow oil.

IR (neat): 3400-3200 (br), 1080

$^1$H NMR (CDCl$_3$): 0.29 (s, 9H), 0.92 (t, 2H, J=7.0 Hz), 1.29 (brs, 20H), 1.65 (m, 2H), 1.85 (br, 2H), 3.89 (t, 1H, J=6.8 Hz), 6.64 (s, 1H) and 7.55 (s, 1H).

MS m/e: Exact mass calculated for C$_{20}$H$_{38}$SiN (M+H)$^{+3}$ 336.2722, found 336.2717.

3-[1-(Acetamido)tridecyl]-5-trimethylsilylfuran

Acetic anhydride (0.1 ml) was added to a solution of 3-(1-aminotridecyl)-5-trimethylsilylfuran (89.8 mg, 0.27 mmol) and triethylamine (0.1 ml) in dichloromethane (1 ml) at room temperature. Stirring was continued overnight (14 hours) while the cooling bath attained room temperature. The residue, after solvent removal, was purified by preparative TLC 20×20 cm, 1000u; developed with 60% ethyl ether/hexane). The title amide was obtained as a pale yellow oil.

$^1$H NMR (CDCl$_3$): 0.26 (s, 9H), 0.89 (t, 3H, J=7.0 Hz), 1.27 (brs, 20H), 1.75 (m, 2H), 2.00 (s, 3H), 4.97 (dt, 1H, J=8.8 Hz, 7.0 Hz), 5.56 (d, 1H, J=8.8 Hz), 6.55 (s, 1H) and 7.53 (s, 1H).

MS m/e: Exact mass calculated for C$_{22}$H$_{41}$NO$_2$Si 379.2906, found 379.2908.

3-1-(Acetamido)tridecyl)]-5-hydroxy-2(5H)-furanone (Compound 29)

A mixture of 3-[1-(acetamido)tridecyl]-5-trimethylsilylfuran (81 mg, 0.21 mmol) and Rose Bengal (5 mg) in tetrahydrofuran (5 ml) was exposed to singlet oxygen at −78 degrees for 2 hours. The residue, after solvent removal, was purified by preparative TLC (20×20 cm, 1000u silica plate; developed with ethyl acetate). The title furanone was obtained as colorless solid, mp 102-103 degrees.

$^1$H NMR (CDCl$_3$): 0.92 (t, 3H, J=7.1 Hz), 1.29 (brs, 20H), 1.75 (m, 2H), 2.07 (brs, 3H), 4.55 (m, 1H), 4.85 (m, 1H), 5.95 (brs, 1H), 6.05 (br, 1H), 6.15 (br, 1H), 6.30 (d, 1H) and 7.0 (br, 1H).

$^{13}$C NMR (CDCl$_3$): 14.1, 22.7, 22.8, 25.8, 29.1, 29.3, 29.5, 29.6, 31.9, 33.5, 47.8, 99.2, 117.9, 170.2, 170.3 and 171.3.

MS m/e: Exact mass calculated for C$_{19}$H$_{34}$NO$_4$(M+H)$^+$ 340.2487, found 340.2476.

1-(Trifluoroacetamido)tridecyl]-5-trimethylsilylfuran

Trifluoroacetic anhydride (0.05 ml) was added to a solution of 3-(1-aminotridecyl)-5-trimethylsilylfuran (80.7 mg, 0.24 mmol) and triethylamine (0.1 ml) in dichloromethane (1 ml) at room temperature. Stirring was continued overnight (14 hours) while the cooling bath attained room temperature. The residue, after solvent removal, was purified by preparative TLC (20×20 cm, 1000u silica plate; developed with 10% ethyl ether/hexane). The title amide was obtained as a pale yellow oil.

$^1$H NMR (CDCl$_3$): 0.27 (s, 9H), 0.89 (t, 3H, J=7.0 Hz), 1.26 (brs, 20H), 1.85 (m, 2H), 4.98 (dt, 1H, J=8.3 Hz, 7.5 Hz), 6.25 (d, 1H, J=8.3 Hz), 6.54 (s, 1H) and 7.58 (s, 1H).

MS m/e: Exact mass calculated for C$_{22}$H$_{38}$NO$_2$SiF$_3$(M+) 433.2624, found 433.2624.

4-[1-Trifluoroacetamido)tridecyl]-5-hydroxy-2(5H)-furanone (Compound 30)

A mixture of 3-[1-trifluoroacetamido)tridecyl]-5-trimethylsilylfuran (60 mg, 0.14 mmol) and Rose Bengal (5 mg) in tetrahydrofuran (5 ml) was exposed to singlet oxygen at −78 degrees for 2 hours. The residue, after solvent removal, was purified by preparative TLC (20×20 cm, 1000u; 60% ethyl ether/hexane). The title furanone was obtained as a colorless solid, mp 138-139 degrees.

$^1$H NMR (CD$_3$OD): 0.89 (t, 3H, J=7 Hz), 1.29 (brs, 20H), 1.75-1.95 (m, 2H), 4.80-4.90 (br, 3H), 6.0 (br, 1H) and 6.15 (brs, 1H).

$^{13}$C NMR (CDCl$_3$): 14.4, 23.8, 26.9, 30.0, 30.4, 30.5, 30.6, 30.8, 33.1, 100.2, 100.4, 100.6, 115.6, 119.3, 119.4, 119.5, 119.7, 119.8, 119.9, 158.6, 159.1, 169.6 and 172.3.

MS m/e: Exact mass calculated for C$_{19}$H$_{31}$NF$_3$O$_4$ (M+H) 394.2205, found 394.2195.

3-1-Methylsulfonamido)tridecyl]-5-trimethylsilylfuran

Methanesulfonyl chloride (37 ul, 0.48 mmol) was added to a solution of 3-(1-aminotridecyl)-5-trimethylsilylfuran (134.6 mg, 0.4 mmol) and triethylamine (67 ul, 0.48 mmol) in dichloromethane (2 ml) at 0 degrees. Stirring continued overnight (14 hours) while the cooling bath attained room temperature. The reaction mixture was quenched with water. Extraction (ethyl ether) and evaporation of the dried (magnesium sulfate) extracts gave an oil, which was purified by flash chromatography on silica using 10% ethyl ether/hexane. Fractions with R$_f$ of about 0.07 on evaporation gave the title sulfonamide as a pale yellow oil.

$^1$H NMR (CDCl$_3$): 0.27 (s, 9H), 0.89 (t, 3H, J=6.4 Hz), 1.26 (brs, 20H), 1.75 (m, 2H), 2.77 (s, 3H), 4.45 (dt+d, 2H), 6.56 (1H) and 7.59 (s, 1H).

MS m/e: Exact mass calculated for C$_{21}$H$_{41}$NSiSO$_3$ (M+) 415.2581, found 415.2576.

4-1-(Methylsulfonamido)tridecyl]-5-hydroxy-(5H)-furanone

A mixture of 3-[1-(methylsulfonamido)tridecyl]-5-trimethylsilylfuran (64 mg, 0.189 mmol) and Rose Bengal (5 mg) in tetrahydrofuran (6 ml) was exposed to singlet oxygen at −78 degrees for 2 hours. The residue, after solvent removal, was purified by preparative TLC (20×20 cm, 1000u silica plate; developed with 70% ethyl ether/hexane. The title furanone was obtained as an off-white solid, mp 95-96 degrees.

$^1$H NMR (CDCL$_3$) 0.89 (t, 3H, J=7.0 Hz), 1.26 (brs, 20H), 1.75 (m, 2H), 3.02 (s, 3H), 4.35 (m, 1H), 5.45 (brd, 1H), 5.55 (brs, 1H), 6.10 (brs, 1H) and 6.22 (br, 1H).

$^{13}$C NMR (CDCl$_3$): 13.9, 22.5, 25.5, 28.9, 29.1, 29.2, 29.4, 29.9, 31.7, 41.5, 97.9, 98.0, 119.5, and 170.7.

MS m/e: Exact mass calculated for C$_{18}$H$_{34}$SNO$_5$(M+) 376.2157, found 376.2165.

3-[1-(Methylcarbamoyl)tridecyl]-5-trimethylsilylfuran

Methyl chloroformate (30 ul, 0.39 mmol) was added to a solution of 3-(1-aminotridecyl)-5-trimethylsilylfuran (109.2 mg, 0.32 mmol) and triethylamine (54 ul, 0.39 mmol) in dichloromethane (2 ml) at 0 degrees. Stirring was continued overnight (14 hours) while the cooling bath attained room temperature. The residue, after solvent removal, was purified by preparative TLC (20×20 cm, 1000u silica plate; developed with 10% ethyl ether/hexane). The title carbamate was obtained as a pale yellow oil.

$^1$H NMR (CDCl$_3$): 0.27 (s, 9H), 0.90 (t, 3H, J=7.0 Hz), 1.27 (brs, 20H), 1.75 (m, 2H), 3.70 (s, 3H), 4.70 (bt+bd, 2H) 6.54 (5.1H) and 7.53 (s, 1H).

MS m/e: Exact mass calculated for C$_{22}$H$_{41}$SiNO$_3$ 395.2855, found 395.2842.

4-[1-(Methylcarbamoyl)tridecyl]-5-hydroxy-2(5H)-furanone

A mixture of 3-[1-(methylcarbamoyl)tridecyl]-5-trimethylsilylfuran (42 mg, 0.11 mmol) and Rose Bengal (5 mg) in tetrahydrofuran (6 ml) was exposed to singlet oxygen at −78 degrees for 2 hours. The residue, after solvent removal, was purified by preparative TLC (20×20 cm, 1000u; developed with 70% ethyl ether/hexane). The title furanone was obtained as a colorless oil, which solidified on storage, mp 77-78 degrees.

$^1$H NMR (CDCl$_3$): 0.89 (t, 3H, J=7.0 Hz), 1.26 (brs, 20H), 1.75 (brm, 2H), 3.69 (brs, 3H), 4.50 (br, 1H), 5.35 (br, 1H), 5.99 (brs, 1H), 6.05 (br, 1H) and 6.15 (br, 1H).

$^{13}$C NMR (CDCl$_3$): 14.1, 22.7, 25.7, 28.9, 29.1, 29.3, 29.5, 29.6, 30.0, 31.9, 33.7, 48.4, 49.1, 52.8, 52.9, 98.1, 98.6, 106.1, 118.2, 118.8, 157.0, 167.8, 170.1 and 170.4.

MS m/e: Exact mass calculated for C$_{19}$H$_{34}$NO$_5$(M+H)+ 356.2436, found 356.2431.

3-1(-aminotridecyl)-5-trimethylsilylfuran is reacted with methyl methylphosphonochloridate to give 3-[1-(3-PN(CCH$_3$)(CH$_3$)O-tridecyl]-5-trimethylsilylfuran. Oxidizing with singlet oxygen gives 4-[1-(3-PN(CCH$_3$)(CH$_3$)O-tridecyl]-5-hydroxy-2(5H)-furanone.

3-(N-methylureido)tridecyl]-5-Trimethylsilylfuran

A solution of methylisocyanate (23 ul, 0.38 mmol) in dichloromethane (0.5 ml) was added to a solution of 3-(1-aminotridecyl)-5-trimethylsilylfuran (85.5 mg, 0.25 mmol) and triethylamine (53 microliter, 0.3 mmol) in dichloromethane (2 ml) at room temperature. Stirring was continued for two days and the reaction mixture was quenched with water. Extraction (dichloromethane) and evaporation of the dried (magnesium sulfate) extracts gave an oil, which was purified by preparative TLC (20×20 CM, 1000ul; developed with 40% ethyl acetate/hexane) to give the titled urea as a colorless oil.

$^1$H NMR (CDCl$_3$): 0.24 (s, 9H), 0.88 (t, 3H, J=7.0 Hz), 1.26 (s, 20H), 1.70 (m, 2H), 2.72 (d, 3H, J=4.8 Hz), 4.65 (m, 2H), 4.80 (m, 1H), 6.53 (s, 1H) and 7.49 (s, 1H).

4-[-1-(N-methylureido)tridecyl]-5-hydroxy-2(5H)-furanone (Compound 32)

A mixture of 3-[1-(N-methylureido)tridecyl]-5-[trimethylsilyfuran (53 mg. 0.14 mmol) and Rose Bengal (Ca., 2 mg) in tetrahydrofuran (5 ml) was exposed to singlet oxygen at 0 degrees for 1.5 hours. The residue, after solvent removal, was purified by preparative TLC (20×20 cm, 1000u; developed with 60% ethyl acetate/hexane) to give the titled furanone as a colorless oil.

$^1$H NMR (CDCl$_3$): 0.89 (t, 3H, J=6.8 Hz), 1.27 (brs, 20H), 1.75 (br, 2H), 2.74 (d, 3H, J=4.7 Hz), 4.45 (br, 1H), 5.28 (br, 1H), 5.65 (brs, 2H), 5.98 (brs, 1H) and 6.10 (brs, 1H).

4-[(-Glutarylamido)tridecyl]-2-triethylsilylfuran

A mixture of 4-(1-aminotridecyl)-2-triethylsilylfuran (250 mg, 0.66 mmol) and glutaric anhydride (150 mg, 1.32 mmol) in dichloromethane was stirred at room temperature for 2 days. The mixture was quenched with dilute hydrochloric acid and was extracted thoroughly with ethyl acetate. Evaporation of the dried (magnesium sulfate) extracts gave a residue which was purified by a silica column using 5% methanol/dichloromethane to give the titled amide as a colorless solid.

$^1$H NMR (CDCl$_3$): 0.75 (q, 6H, J=8.0 Hz), 0.088 (t, 3H, J=6.5 Hz), 0.99 (t, 9H, J=8.0 Hz), 1.24 (m, 20H), 1.70 (p, 2H, J=7.3 Hz), 1.97 (m, 2H), 2.28 (t, 2H, J=23 Hz), 2.41 (t, 2H, J=7.3 Hz), 4.97 (q, 1H, J=8.2 Hz), 5.65 (d, 1H, J=8.2 Hz), 6.50 (s, 1H) and 7.50 (s, 1H).

$^{13}$C NMR (CDCL$_3$): 3.15, 7.30, 14.1, 20.8, 22.7, 26.0, 29.3, 29.5, 29.6, 31.9, 33.0, 35.3, 35.4, 45.3, 119.7, 126.3, 143.4, 159.5, 171.5 and 177.8.

HRMS exact mass calculated for $C_{28}H_{51}NO_4Si$ (M+) 493.3587, found 493.3577.

4-[(1-Glutarylamido)tridecyl]-5-hydroxy-2(5H)-furanone

A mixture of 4-[(1-glutarylamido)tridecyl]-2-triethylsilylfuran (222.5 mg, 0.45 mmol), water (a few drops) and Rose Bengal (5 mg) was exposed to singlet oxygen at 0 degrees for 1.5 hours. The residue, after solvent removal, was purified by a silica column using 10% methanol/chloroform to give the titled furanone as a colorless solid.

$^1$H NMR (CD$_3$OD): 0.79 (t, 3H, J=6.5 Hz), 1.18 (m, 20H), 1.50 (m, 2H), 1.80 (t, 2H, J=7.0 Hz), 2.23 (t, 4H, J=7.0 Hz), 4.60 (m, 1H), 4.73 (m, 1H), 5.82 (brs, 1H), 5.88 (brs, 1H), 5.99 (brs, 1H), 8.20 (m, 1H) and 8.30 (m, 1H).

$^{13}$C NMR (CD$_3$OD): 14.4, 22.2, 23.7, 26.9, 30.1, 30.5, 30.7, 30.8, 33.0, 34.0, 35.8, 99.8, 100.3, 118.1, 118.7, 172.1, 172.6, 172.7, 172.8, 175.1 and 176.7.

HRMS exact mass calculated for $C_{22}H_{38}NO_6$ (M+H)+ 412.2696, found 412.2696.

4-(1-Azidotridecyl)-2-triethylsilylfuran

A solution of diphenylphosphonyl azide (143 mg, 0.52 mmol in THF (2 ml) was added over a period of 15 minutes to a solution of 4-(1-hydroxytridecyl)-2-triethylsilylfuran (200 mg, 0.52 mmol), triphenylphosphine (140 mg, 0.52 mmol) and diethyl azidocarboxylate (90 mg, 0.52 mmol) in THF (10 ml) at room temperature. After stirring for 2 days, the mixture was evaporated in the presence of a minimum amount of silica gel. The residue was purified by flash chromatography on silica using 5% ethyl ether/hexane to give the titled azide.

$^1$H NMR (CDCl$_3$) 0.77 (q, 6H, J=0.8 Hz), 0.88 (t, 3H, J=6.4 Hz), 0.98 (t, 9H, J=8.0 Hz), 1.25 (m, 20H), 1.75 (m, 2H), 4.33 (t, 1H, J=7.5 Hz), 6.60 (s, 1H) and 7.61 (s, 1H).

4-(1-Aminotridecyl)-2-triethylsilylfuran

A solution of lithium aluminum hydride (a 1.0M solution in THF; 4.22 ml, 4.22 mmol) was added slowly to a solution of 4-(1-azidotridecyl)-2-triethylsilylfuran (1.55 g, 3.84 mmol) at 0 degrees C. under argon. After stirring at room temperature for 2 hours, the mixture was cooled to 0 degrees C. and quenched with 2M sodium hydroxide. Anhydrous sodium sulfate was added to coagulate the aluminum salt and the mixture was extracted thoroughly with ethyl acetate. Evaporation of the dried (magnesium sulfate) extracts gave an oil, which was purified by flash chromatography on silica using 5% methanol/dichloromethane to give the titled amine.

$^1$H NMR (CDCl$_3$) 0.76 (q, 6H, J=8.0 Hz), 0.88 (t, 3H, J=6.5 Hz), 0.98 (t, 9H, J=8.0 Hz), 1.25 (m, 20H), 1.80 (m, 2H), 3.85 (t, 1H, J=6.8 Hz), 6.60 (s, 1H) and 7.50 (s, 1H).

EXAMPLE 5

Methyl 3-(2-trimethylsilyl-4-furyl)propen-2-oate

A mixture of methyl(triphenylphosphoranylidene)acetate (994 mg, 2.97 mmol) and 2-trimethylsilyl-4-furaldehyde (384 mg, 2.29 mmol) in tetrahydrofuran (10 ml) was stirred at room temperature for 48 hours. The reaction mixture was evaporated with a minimum amount of silica and the residue was flash chromatographed on silica using 5% ethyl ether/petroleum ether. Fraction with R$_f$ of about 0.16 on evaporation afforded the title ester as a pale yellow oil.

$^1$H NMR (CDCl$_3$): 0.39 (s, 9H), 3.79 (s, 3H), 6.15 (d, 1H, J=15.9 Hz), 6.79 (s, 1H), 7.60 (d, 1H, J=15.9 Hz) and 7.83 (s, 1H).

$^{13}$C NMR (CDCl$_3$): −2.0, 51.3, 116.7, 122.5, 134.9, 148.6, 162.8 and 167.4.

MS m/e Exact mass calculated for $C_{11}H_{16}O_3Si$ (M+): 224.0868, found 224.0875.

Methyl 3-(2-trimethylsilyl-4-furyl)propionate

A solution of methyl-1-(2-trimethylsilyl-4-furyl)-propen-2-oate (107.7 mg, 0.48 mmol) in ethyl ether (5 ml) was hydrogenated over platinum (IV) oxide (ca. 10 mg) at room temperature for 14 hours. The mixture was filtered through celite and the filtrate on evaporation gave the desired ester, which was used directly in the next step.

$^1$H NMR (CDCl$_3$): 0.24 (s, 9H), 2.57 (t, 2H, J=6.7 Hz), 2.76 (t, 2H, J=6.7 Hz), 3.69 (s, 3H), 6.49 (s, 1H) and 7.43 (s, 1H).

$^{13}$C NMR (CDCl$_3$): −1.8, 20.0, 34.6, 51.4, 120.7, 123.3, 143.1, 160.6 and 173.2.

MS m/e: Exact mass calculated for $C_{11}H_{18}O_3Si$ (M+): 226.1025, found 226.1034.

3-(2-Trimethylsilyl-4-furyl)propan-1-ol

A solution of methyl 3-(2-trimethylsilyl-4-furyl)-propionate (from above) in tetrahydrofuran (3 ml) was added dropwise to a suspension of lithium aluminum hydride (27 mg) in tetrahydrofuran (4 ml) at room temperature. After 3 hours, the mixture was quenched with ethyl acetate and extracted with ether. Evaporation of the dried (magnesium sulphate) extracts gave the title alcohol, which was used in the next step without purification.

$^1$H NMR (CDCl$_3$): 0.25 (s, 9H), 1.65 (br, 1H), 1.84 (p, 2H, J=73 Hz), 2.52 (t, 2H, J=7.8 Hz), 3.69 (t, 2H, J=6.3 Hz), 6.51 (s, 1H) and 7.42 (s, 1H).

MS m/e (% abundance): 1.98 (M+, 11), 154 (70), 139 (26), 101 (26), 73 (79).

3-(2-Trimethylsilyl-4-furyl)propan-1-al

To a stirring mixture of pyridinium chlorochromate (3.89 g, 18.03 mmol) suspended in methylene chloride (100 ml) at 0 degrees was added 3-(2-trimethylsilyl-4-furyl)propan-1-ol (1.19 g, 6.01 mmol), prepared as in Example 2, in dry methylene chloride (15 ml). This mixture was allowed to warm to room temperature, stirred for 90 minutes, filtered and concentrated to give the desired aldehyde.

IR (CHCl$_3$): 3020, 1720, 1220 cm$^{-1}$.

$^1$H NMR (CDCl$_3$): 9.82 (s, 1H); 7.42 (s, 1H); 6.48 (s, 1H); 2.65 to 2.85 (m, 4H); 0.24 (s, 9H).

$^{13}$C NMR (CDCl$_3$): 201.8, 161.1, 143.2, 123.2, 120.7, 44.1, 17.3, −1.7.

MS m/e: calculated for $C_{10}H_{16}O_2Si$(M+): 196.0919, found 196.0943.

Dimethyl-2-oxotridecylphosphonate

To a stirred solution of methyl laurate (1.5 g, 7.0 mmol) in tetrahydrofuran (120 ml) at −78 degrees was added the lithium salt of dimethylmethylphosphonate (0.901 g, 7.26 mmol; generated with n-butyl lithium (5.29 ml of a 1.39M solution in hexane). The stirring mixture was warmed to room temperature over four hours and partitioned between ethyl ether and 5% aqueous ammonium chloride solution. The organic portion was washed with 5% sodium bicarbonate, water, saturated sodium chloride solution, dried over magnesium sulfate, filtered and concentrated to give a colorless oil. Purification by flash chromatography (silica, 80% to 90% ethyl acetate/hexane) gave the desired phosphonate ester.

IR (CHCl$_3$): 2920, 2850, 1710, 1250 cm$^{-1}$.

$^1$H NMR (CDCl$_3$): 3.81 (s, 3H); 3.77 (s, 3H); 3.09 (d, J=22.7 Hz, 2H); 2.61 (t, J=7.3 Hz, 2H); 1.51 to 1.62 (m, 2H); 1.20–1.35 (m, 16H); 0.88 (t, J=6.7 Hz, 3H).

$^{13}$C NMR (CDCl$_3$): 201.9, 52.9, 52.8, 44.1, 42.0, 40.2, 31.8, 29.5, 29.2, 28.9, 28.8, 23.3, 22.5, 14.0.

MS m/e: Calculated for C$_{15}$H$_{31}$O$_4$P(M+): 306.1960 found 306 1963.

4-(6-Oxo-3-hexadecenyl)-2-trimethylsilylfuran

To sodium hydride (0.016 g, 0.677 mmol) under argon was added dimethyl-2-oxotridecylphosphonate (0.207 g, 0.677 mmol) in tetrahydrofuran (5 ml). The mixture was stirred for 20 minutes at room temperature, followed by the addition of 3-(2-trimethylsilyl-4-furyl)-propan-1-al (0.111 g, 0.564 mmol) in tetrahydrofuran (5 ml). After stirring for five hours the reaction was quenched with 10% aqueous hydrochloric acid and extracted with ethyl ether. The organic portion was washed with 5% sodium bicarbonate, water, saturated sodium chloride solution, dried over magnesium sulfate, filtered and concentrated to give an oil. Purification by flash chromatography (silica, 3% to 5% ethyl acetate/hexane) gave the desired enone.

IR (CHCl$_3$): 2940, 1660, 1250 cm$^{-1}$.

$^1$H NMR (CDCl$_3$): 7.41 (s, 1H); 6.77 to 6.90 (m, 1H); 6.49 (s, 1H); 6.13 (d, J=16.0 Hz, 1H); 2.42 to 2.65 (m, 6H); 1.59 (t, J=7.1 Hz, 2H); 1.21 to 1.35 (m, 16H); 0.89 (t, J=6.7 Hz, 2H); 0.25 (s, 9H).

$^{13}$C NMR (CDCl$_3$): 200.9, 160.8, 145.9, 143.1, 130.6, 123.6, 120.7, 40.2, 32.8, 31.9, 29.6, 29.4, 29.3, 24.3, 23.3, 22.6, 14.0, −1.7.

Ms m/e: Calculated for C$_{23}$H$_{40}$O$_2$Si(M+): 376.2797, found 376.2808.

4-(5-Oxo-3-hexadecenyl)-5-hydroxy-2(5H)-furanone

A stirred solution of 4-(5-oxo-3-hexadecenyl)-2-trimethylsilylfuran (47 mg, 0.125 mmol) and Rose Bengal in acetone (2 ml) was flushed with oxygen and cooled to −78 degrees. The solution was subsequently irradiated with a 150 watt flood lamp while under constant, positive pressure of oxygen until starting material was no longer visible by TLC. The solution was warmed to room temperature, concentrated and passed through silica (40% ethyl acetate/hexane) to give a pale red solid. This material was further purified by recrystallization (hexane/ethyl ether) to give the desired hydroxybutenolide.

IR (CHCl$_3$): 3340 (broad), 2920, 1750, 1630 cm$^{-1}$.

$^1$H NMR (CDCl$_3$): 6.83 (dt, J=16 Hz, J=5.8 Hz, 1H); 6.19 1H); 2.45 to 2.75 (m, 6H); 1.59 (t, J=7.0 Hz, 2H); 1.15 to 1.40 (m, 16H); 0.88 (t, J=6.7 Hz, 3H).

$^{13}$C NMR (CDCl$_3$): 201.5, 171.5, 168.2, 144.4, 131.0, 117.9, 99.2, 40.5, 31.8, multiple peaks from 29.0 to 29.5, 25.9, 24.1, 22.6, 14.0.

MS m/e: calculated for C$_{20}$H$_{36}$O$_4$N(M+NH$_4$)+: 354.2644, found 354.2658.

4-(5-Oxohexadecyl)-2-trimethylsilylfuran

To 4-(5-oxo-3-hexadecenyl)-2-trimethylsilylfuran (98 mg, 0.261 mmol), prepared as in Example 3, in ethyl acetate (2 ml) was added platinum oxide (10 mg, 0.044 mmol). This mixture was subjected to one atmosphere of hydrogen at room temperature with stirring for 2½ hours. The reaction mixture was filtered and concentrated to give a yellow oil. Purification by flash chromatography (silica, 3% ethyl ether/hexane) gave the desired ketone.

IR (CHCl$_3$): 2920, 1700 cm$^{-1}$.

$^1$H NMR (CDCl$_3$): 7.39 (s, 1H); 6.48 (s, 1H); 2.27 to 2.50 (m, 6H); 1.50 to 1.70 (m, 6H); 1.10 to 1.40 (m, 16H); 0.88 (t, J=6.6 Hz, 3H); 0.24 (s, 9H).

$^{13}$C NMR (CDCl$_3$): 211.3, 160.4, 142.9, 124.7, 121.0, 42.8, 42.7, 31.9, 29.7, 29.6, 29.4, 29.2, 24.2, 23.8, 23.5, 22.7, 14.1, −1.7.

MS m/e: calculated for C$_{23}$H$_{42}$O$_2$Si(M+): 378.2954, found 378.2968.

4-(5-Oxohexadecyl)-5-hydroxy-2(5H)-furanone

A stirred solution of 4-(5-oxohexadecyl)-2-trimethylsilylfuran (71 mg, 0.187 mmol) and Rose Bengal in acetone (20 ml) was flushed with oxygen and cooled to −78 degrees. The solution was subsequently irradiated with a 150 watt flood lamp while under constant positive pressure of oxygen until no starting material remained. The solution was warmed to room temperature, concentrated and filtered through silica to give a pale red solid. Purification by flash chromatography (silica, 40% ethyl acetate/hexane) gave the desired hydroxybutenolide.

IR (CHCl$_3$): 3360 (broad), 2920, 1740, 1705 cm$^{-1}$.

$^1$H NMR (CDCl$_3$): 6.04 (d, J=5.5 Hz, 1H); 5.80 to 5.90 (m, 2H); 2.32 to 2.57 (m, 6H); 1.50 to 1.73 (m, 6H), 1.20 to 1.40 (m, 16H); 0.88 (t, J=6.7 Hz, 3H).

$^{13}$C NMR (CDCl$_3$): 212.1, 171.9, 169.7, 117.4, 99.3, 43.0, 42.0, 31.9, 29.6, 29.4, 29.3, 29.2.

MS m/e: calculated for C$_{20}$H$_{34}$O$_4$(M+): 338.2457, found 338.2449.

Triethyl 1-decylphosphonoacetate

To a suspension of sodium hydride (0.321 g, 13.38 mmol) in tetrahydrofuran 30 ml) at room temperature was added triethylphosphonoacetate (2.0 g, 8.92 mmol). After stirring for 15 minutes to this mixture was added 1-bromodecane (2.17 g, 9.81 mmol) and sodium iodide (0.30 g, 2.00 mmol). After refluxing for 18 hours the reaction was quenched with 10% aqueous hydrochloric acid and extracted into ethyl ether. The organic portion was washed with 5% sodium bicarbonate, water, saturated sodium chloride solution, dried over magnesium sulfate, filtered and concentrated to give a yellow oil. Purification by flash chromatography (silica, 30% to 50% ethyl acetate/hexane) gave the desired phosphonate ester.

IR (CHCl$_3$): 3010, 2920, 1720, 1230 cm$^{-1}$.

$^1$H NMR (CDCl$_3$): 4.08 to 4.26 (m, 6H); 2.86 to 2.92 (ddd, J=10.9 Hz, 22.5 Hz, 3.8 Hz, 1H); 1.75 to 1.90 (m, 1H); 1.90 to 2.05 (m, 1H); 1.20 to 1.40 (m, 25H); 0.88 (t, J=6.6 Hz, 3H).

$^{13}$C NMR (CDCl$_3$): 168.6, 62.1, 62.0, 61.9, 60.6, 46.2, 44.7, 31.4 multiple peaks from 26.4 to 29.0, 22.1, 15.9, 15.8, 13.6, 13.5.

MS m/e: Calculated for C$_{18}$H$_{38}$O$_5$P (MH)+: 365.2457, found 365.2465.

(E) Ethyl 2-decyl-5-(2-trimethylsilyl-4-furyl)-penten-2-oate and (Z) Ethyl 2-decyl-5-(2-trimethylsilyl-4-furyl)penten-2-oate To sodium hydride (0.111 g, 2.78 mmol) under argon was added triethyl 1-decylphosphonoacetate (0.813 g, 2.32 mmol) in tetrahydrofuran (10 ml). The mixture was stirred for 10 minutes at room temperature, followed by the addition of 3-(2-trimethylsilyl-4-furyl)propan-1-al (0.455 g, 2.32 mmol). After 10 minutes the reaction was quenched with 10% aqueous hydrochloric acid and extracted with ethyl ether. The organic portion was washed with 5% sodium bicarbonate, water, saturated sodium chloride solution, dried over magnesium sulfate, filtered and concentrated to give a yellow oil. Purification by preparative TLC (silica, 3% ethyl acetate/hexane) afforded the desired E and Z isomers.

(Z) Ethyl 2-decyl-5-(2-trimethylsilyl-4-furyl)penten-2-oate

IR (CHCl$_3$): 2930, 2860, 1695, 1250 cm$^{-1}$.

$^1$H NMR (CDCl$_3$): 7.24 (s, 1H); 6.75 (t, J=7.3 Hz, 1H); 6.50 (s, 1H); 4.19 (q, J=7.1 Hz, 2H); 2.50 to 2.62 (m, 2H); 2.38 to 2.48 (m, 2H); 2.27 (t, J=7.3, 2H); 1.20 to 1.50 (m, 19H); 0.88 (t, J=6.7 Hz, 3H); 0.25 (s, 9H).

$^{13}$C NMR (CDCl$_3$): 168.1, 160.7, 143.1, 141.1, 133.3, 124.1, 60.4, 31.9, multiple peaks from 29.6 to 29.2, 26.8, 24.0, 22.7, 18.0, 14.3, 14.1, −1.7.

MS m/e: Calculated for C$_{24}$H$_{42}$O$_3$Si(M$^+$): 406.2903, found 406.2892.

(E) Ethyl 2-decyl-5-(2-trimethylsilyl-4-furyl)-penten-2-oate

IR (CHCl$_3$): 2920, 2850, 1695, 1245 cm$^{-1}$.

$^1$H NMR (CDCl$_3$): 7.41 (s, 1H); 6.50 (s, 1H); 5.85 (t, J=7.1 Hz, 1H); 4.18 (q, J=7.1 Hz, 2H); 2.61 to 2.73 (m, 2H); 2.49 to 2.60 (m, 2H); 2.23 (t, J=7.3 Hz, 2H); 1.15 to 1.50 (m, 19H); 0.89 (t, J=5.8 Hz, 3H); 0.26 (s, 9H).

$^{13}$C NMR (CDCl$_3$): 168.2, 160.3, 143.1, 140.0, 133.0, 124.3, 121.1, 60.0, 34.5, 31.9, multiple peaks from 28.7 to 29.9, 24.5, 22.7, 14.3, 14.1, −1.6.

MS m/e: calculated for C$_{24}$H$_{42}$O$_3$Si(M$^+$): 406.2903, found 406.2898.

4-(4-Carboethoxytetradecyl)-2-trimethylsilylfuran

To a stirred solution of (Z) ethyl 2-decyl-5-(2-trimethylsilyl-4-furyl)penten-2-oate (99 mg, 0.244 mmol) in ethyl acetate (5 ml) was added platinum oxide (28 mg, 0.122 mmol). This mixture was subjected to one atmosphere of hydrogen for 18 hours, then filtered and concentrated to give an oil. Purification by flash chromatography (silica, 0% to 3% ethyl ether/hexane) gave the desired ester.

IR (CHCl$_3$): 2920, 2850, 1700 cm$^{-1}$.

$^1$H NMR (CDCl$_3$): 7.39 (s, 1H); 6.47 (s, 1H); 4.14 (q, J=7.0 Hz, 2H); 2.27 to 2.44 (m, 3H); 1.37 to 1.70 (m, 6H); 1.15 to 1.36 (m, 19H); 0.88 (t, J=6.5 Hz, 3H); 0.24 (s, 9H).

$^{13}$C NMR (CDCl$_3$): 176.4, 160.4, 143.0, 124.7, 121.0, 60.0, 45.6, 32.5, 32.3, 32.1, 31.9, 29.8, 29.6, 29.5, 29.3, 27.9, 27.4, 24.5, 22.7, 14.3, 14.1, −1.6.

MS m/e: Calculated for C$_{24}$H$_{44}$O$_3$Si(M$^+$): 408.3060, found 408.3065.

4-(4-Carboethoxytetradecyl)-5-hydroxy-2(5H)-furanone

A stirred solution of 4-(4-carboethoxytetradecyl)-2-trimethylsilylfuran (50 mg, 0.123 mmol) and Rose Bengal in acetone (25 ml) was flushed with oxygen and cooled to −78 degrees. The solution was subsequently irradiated with a 150 watt flood lamp while under constant, positive pressure of oxygen until no starting material was visible by TLC. The solution was warmed to room temperature and concentrated to give a red oil. Purification by preparative TLC (silica, 30% ethyl acetate/hexane) gave the desired hydroxybutenolide.

IR (CHCl$_3$): 3340 (broad, 2920, 2825, 1720 cm$^{-1}$.

$^1$H NMR (mixture of diastereomers), (CDCl$_3$): 6.01 (s, 1H); 5.84 (s, 1H); 5.29 (broad s, 1H); 4.15 (q, J=7.1 Hz, 2H); 2.25 to 2.51 (m, 3H); 1.15 to 1.75 (m, 25H); 0.88 (t, J=6.7 Hz, 3H).

$^{13}$C NMR (mixture of diastereomers), (CDCl$_3$): 176.6, 171.6, 169.3, 117.6, 99.1, 60.5, 45.5, 32.6, 31.9, 31.7, multiple peaks between 29.3 and 29.6 multiple peaks between 27.3 and 27.6, 24.5, 22.7, 14.3, 14.1.

MS m/e: Calculated for C$_{21}$H$_{36}$O$_5$(M$^+$): 368.2563, found 368.2558.

(E)(Z)-Methyl 3-(2-triethylsilyl-4-furyl)propen-2-oate) (Compound 10)

A mixture of methyl(triphenylphosphoranylidene)acetate (4.77 g, 14.3 mmol) and 5-triethylsilyl-3-furaldehyde (2.0 g, 9.5 mmol) in tetrahydrofuran (30 ml) was refluxed under argon for 2 days. The reaction mixture was evaporated with a minimum amount of silica and the residue was chromatographed on a silica column using 2.5% ethyl ether/hexane to give a mixture of (E),(Z)-methyl 3-(2-triethylsilyl-4-furyl)propen-2-oate (E)-isomer, R$_f$ 0.19 (5% ethyl ether/hexane) and (Z)-isomer, R$_f$ 0.38 (5% ethyl ether/hexane).

$^1$H NMR (CDCl$_3$) (E)-isomer: 0.78 (q, 6H, J=8.0 Hz), 0.99 (t, 9H, J=8.0 Hz), 3.78 (s, 3H), 6.15 (d, 1H, J=15.7 Hz), 6.79 (s, 1H), 7.61 (d, 1H, J=15.7 Hz) and 7.84 (s, 1H). (Z)-isomer: 0.79 (q, 6H, J=8.0 Hz), 0.99 (t, 9H, J=8.0 Hz), 3.75 (s, 3H), 5.77 (d, 1H, J=12.6 Hz), 6.74 (d, 1H, J=12.6 Hz), 7.13 (s, 1H) and 8.35 (s, 1H).

LRMS (m/e, % abundance) 266 (M$^+$, 31), 238 (19), 237 (100), 209 (24), 117 (37), 89 (44) and 87 (11).

Methyl 3-(2-triethylsilyl-4-furyl)propionate

A solution of (E)(Z) methyl 3-(2-triethylsilyl-4-furyl)-propen-2-oate (1.83 g, 6.88 mmol) in ethyl acetate (10 ml was hydrogenated over platinum (IV) oxide (ca 15 mg) at room temperature for 16 hours. The mixture was filtered through celite and the filtrate on evaporation gave an oil, which was purified by a silica column using 5% ethyl ether/hexane to give the titled ester.

$^1$H NMR (CDCl$_3$): 0.72 (q, 6H, J=8.0 Hz), 0.79 (t, 9H, J=8.0 Hz), 2.57 (t, 2H, J=7.7 Hz), 2.76 (t,2H, J=7.7 Hz), 3.68 (s, 3H), 6.50 (s, 1H) and 7.44 (s, 1H).

3-(2-Triethylsilyl-4-furyl)propan-1-ol

Lithium aluminium hydride (a 1M solution in tetrahydrofuran; 5.17 ml, 5.17 mmol) was added dropwise to a solution of methyl 3-(2-triethylsilyl-4-furyl)propionate (1.38 g, 5.17 mmol) in tetrahydrofuran (5 ml) at 0 degrees under argon. After 20 minutes, the mixture was quenched with water and extracted with ethyl acetate. Evaporation of the dried (magnesium sulfate) extracts gave the desired alcohol, which was used directly in the next step.

¹H NMR (CDCl₃): 0.76 (q, 6H, J=8.0 Hz), 0.98 (t, 9H, J=8.0 Hz), 1.84 (m, 2H), 2.52 (t, 2H, J=7.4 Hz), 3.69 (t, 2H, 6.5 Hz), 6.52 (s, 1H) and 7.43 (s, 1H).

3-(2-Triethylsilyl-4-furyl)-1-propanal (Compound 5)

A mixture of dimethyl sulfoxide (0.9 ml) and dichloromethane (9 ml) was added to a solution of oxalyl chloride (0.64 ml, 7.39 mmol) at −78 degrees under argon. After 5 minutes, a solution of 3-(2-triethylsilyl-4-furyl)propan-1-ol (1.27 g, 5.28 mmol) in dichloromethane (9.0 ml) was added dropwise and after 20 minutes, triethylamine (2.9 ml, 21.1 mmol) was added. Stirring was continued at −78 degrees C. for 40 minutes and at room temperature for 3 hours. The mixture was quenched with water and was extracted thoroughly with ethyl ether. Evaporation of the dried (magnesium sulfate) extracts gave an oil, which was purified by a silica column to give the titled aldehyde.

¹H NMR (CDCl₃): 0.75 (q, 6H, J=7.3 Hz), 0.97 (t, 9H, J=7.3 Hz), 2.73 (m, 4H), 6.49 (s, 1H), 7.43 (s, 1H) and 9.80 (s, 1H).

¹³C NMR (CDCl₃): 2.9, 6.9, 17.1, 43.9, 121.9, 123.2, 143.5, 159.3 and 202.1.

4-(4,4-Dibromo-3-butenyl)-2-triethylsilylfuran 3-(2-Triethylsilyl-4-furyl)-1-propanal (Compound 5, 500 mg, 2.09 mmol) was added to a mixture of carbon tetrabromide 868 mg, 2.62 mmol) and triphenylphosphine (1.27 g, 5.25 mmol) in dichloromethane at 0 degrees under argon. After 4 hours, the mixture was diluted with pentane and filtered. Evaporation of the filtrate gave a residue, which was purified by a silica column using hexane to give the titled dibromide.

¹H NMR (CDCl₃): 0.76 (q, 6H, J=8.0 Hz), 0.98 (t, 9H, J=8.0 Hz), 2.36 (dt, 2H, J=7.5 Hz), 2.55 (t, 2H, J=7.6 Hz), 6.41 (t, 1H, J=7.0 Hz), 6.50 (s, 1H) and 7.43 (s, 1H).

¹³C NMR (CDCl₃): 3.2, 7.3, 14.1, 19.9, 22.7, 24.2, 25.2, 29.4, 29.5, 29.6, 31.6, 31.9, 38.1, 62.7, 81.9, 84.8, 121.9, 123.3, 143.3 and 158.5.

HRMS exact mass calculated for C₂₆H₄₆O₂Si (M+) 418.3267, found 418.3258.

4-(5-Hydroxy-3-hexadecynyl)-2-triethylsilylfuran n-Butyl lithium (a 2.5M solution in tetrahydrofuran; 0.42 ml, 1.04 mmol) was added dropwise to a solution of 4-(4,4-dibromo-3-butenyl)-2-triethylsilylfuran (200 mg, 0.51 mmol) in tetrahydrofuran (8 ml) at −78 degrees under argon. After 2 hours, a solution of 1-dodecanal (102 mg, 0.56 mmol) in tetrahydrofuran (1 ml) was added. Stirring was continued for 14 hours, while the cooling bath attained room temperature. The mixture was quenched with water and was extracted with ethyl ether. Evaporation of the dried (magnesium sulfate) extracts gave a residue, which was purified by a silica column with 15% ethyl ether/hexane to give the titled alcohol.

¹H NMR (CDCl₃): 0.76 (q, 6H, J=8.0 Hz), 0.88 (t, 3H, J=5.3 Hz), 0.95 (t, 9H, J=8.0 Hz), 1.26 (m, 18H), 1.60 (m, 2H), 2.45 (t, 2H, J=7.4 Hz), 2.64 (t, 2H, J=7.4 Hz), 4.34 (dd, 1H, J=6.4 Hz, 5.5 Hz), 6.55 (s, 1H) and 7.48 (s, 1H).

4-(5-Oxo-3-hexadecynyl)-2-triethylsilylfuran

Jones reagent (a 2.6M solution in sulfuric acid; 0.13 ml, 0.36 mmol) was added dropwise to a solution of 4-(5-hydroxy-3-hexadecynyl)-2-triethylsilylfuran (136.4 mg, 0.33 mmol) in acetone (5 ml) at 0 degrees. After 20 minutes, the excess Jones reagent was destroyed with ethanol (ca 1 ml) and the mixture was diluted with water. The organic phase was separated, dried (magnesium sulfate) and evaporated down to give an oil, which was purified by preparative silica plates to give the titled ketone.

¹H NMR (CDCl₃): 0.76 (q, 6H, J=8.0 Hz), 0.88 (t, 3H, J=7.0 Hz), 0.98 (t, 9H, J-8.0 Hz), 1.25 (m, 16H), 1.60 (m, 2H), 2.50 (t, 2H, J=7.5 Hz), 2.60 (t, 2H, J=6.8 Hz), 2.71 (t, 2H, J=6.8 Hz), 6.54 (s, 1H) and 7.50 (s, 1H).

¹³C NMR (CDCl₃): 3.2, 7.3, 14.1, 20.2, 22.7, 23.3, 24.0, 28.9, 29.3, 29.4, 29.6, 31.9, 45.5, 81.2, 93.1, 121.6, 122.6, 143.4, 159.0 and 188.4.

HRMS exact mass calculated for C₂₆H₄₄O₂Si(M+) 416.3105, found 416.3092.

4-(5-Oxo-3-hexadecynyl)-5-hydroxy-2(5H)-furanone

A mixture of 4-(5-oxo-3-hexadecynyl)-2-triethylsilylfuran (74.4 mg, 0.18 mmol), water (a few drops) and Rose Bengal (5 mg) in tetrahydrofuran (7 ml) was exposed to singlet oxygen at 0 degrees for 1 hour. The residue, after solvent removal, was purified by preparative silica plates (developed with 60% ethyl ether/hexane) to give the titled furanone.

¹H NMR (CDCl₃): 0.88 (t, 3H, J=6.9 Hz), 1.26 (m, 16H), 1.65 (m, 2H), 2.53 (t, 2H, J=7.4 Hz), 2.75 (m, 4H), 4.35 (brs, 1H), 6.00 (s, 1H) and 6.08 (d, 1H, J=7.4 Hz).

¹³C NMR (CDCl₃): 13.8, 16.4, 22.4, 23.7, 25.7, 28.7, 29.1, 29.2, 29.4, 31.7, 45.3, 81.6, 91.3, 99.1, 118.7, 166.8, 171.5 and 189.3.

HRMS exact mass calculated for C₂₀H₃₁O₄ (M+H)+ 335.2222, found 335.2226.

3-(2-Trimethylsilyl-4-furyl)propan-1-al is treated with (triphenylphosphoranylidene) acetaldehyde in tetrahydrofuran to give 5-(2-trimethylsilyl-4-furyl)-pent-2-en-1-al which is hydrogenated in the presence of a palladium catalyst to give 5-(2-trimethylsilyl-4-yl)-pentan-1-al. Treating this intermediate with C₉H₁₉COCH₂PO)OCH₃)₂ and sodium hydride in trimethylsilylfuran and oxidizing gives 4-(7-oxo-5-hexadecenyl)-5-hydroxy-2(5H)-furanone.

Hydrogenating 3-(7-oxo-5-hexadecenyl)-5-trimethylsilylfuran using platinum oxide as catalyst and oxidizing gives 4-(7-oxohexadecyl)-5-hydroxy-2(5H)-furanone.

3-(2-Trimethylsilyl-4-furyl)propan-1-al is reacted with dioctylmalonate in tetrahydrofuran in the presence of acetic acid and piperidine to give 3-[4,4-di(carbooctanoxy)-3-butenyl]-5-trimethylsilylfuran which is treated with cold aqueous potassium hydroxide to give 3-(4-carboxy-4-carbooctanoxy-3-butenyl)-5-trimethylsilylfuran.

A mixture of the above prepared furan compound and Rose Bengal in tetrahydrofuran is exposed to singlet oxygen at −78 degrees for 2 hours to give 4-(4-carboxy-4-carbooctanoxy-3-butenyl)-5-hydroxy-2(5H)-furanone.

3-(4-Carboxy-4-carbooctanoxy-3-butenyl)-5-trimethylsilylfuran is reacted with ethanol in the presence of 1,3-dicyclohexylcarbodiimide and 4-dimethylaminopyridine to give 3-(4-carboethoxy-4-carbooctanoxy-3-butenyl)-5-trimethylsilylfuran. Oxidizing this intermediate gives 4-(4-carboethoxy-4-carbooctanoxy-3-butenyl)-5-hydroxy-2(5H)-furanone.

EXAMPLE 6

2-Trimethylsilyl-4-vinylfuran n-Butyl lithium (a 1.6M solution in hexane; 2.23 ml, 3.57 mmol) was added dropwise to a suspension of methyltriphenylphosphonium bromide (262 mg, 0.73 mmol) in tetrahydrofuran 8 ml) at 0 degrees under argon. After 20 minutes, a solution of 5-trimethylsilyl-3-furaldehyde (102 mg, 0.61 mmol) in tetrahydrofuran (½ ml) was added. Stirring was continued for 18 hours while the cooling bath attained room temperature. The mixture was quenched with methanol/water (1:1, 20 ml) and extracted with pentane. Evaporation of the dried (magnesium sulphate) extracts gave an oil, which was flash chromatographed on silica using pentane. The title vinylfuran was obtained as a colorless oil.

$^1$H NMR (CDCl$_3$): 0.31 (s, 9H), 5.15 (d, 1H, J=10.2 Hz), 5.50 (d, 1H, J=17.6 Hz), 6.64 (dd, 1H, J=17.6 Hz, 10.2 Hz), 6.82 (s, 1H) and 7.65 (s, 1H).

MS m/e (% abundance): 184 (M+NH$_H$+), 22), 158 (14), 108 (26), 90 (23), 74 (68) and 60 (100).

4-(1,2-Dihydroxyethyl)-2-trimethylsilylfuran

2-Trimethylsilyl-4-vinylfuran (272 mg, 1.64 mmol) was added to a mixture of 4-methylmorpholine N-oxide (203 mg, 1.74 mmol), osmium tetroxide (a 2.5% by weight solution in tertbutanol; 0.1 ml), water (3.5 ml) and acetone (1.5 ml) at room temperature under argon. Stirring was continued for 19 hours and most of the acetone was evaporated under vacuum. Sodium bisulphite was added to the residue and the pH of the solution was adjusted to 1 with dilute sulphuric acid. After being saturated with sodium chloride, the solution was extracted thoroughly with ethyl acetate. Evaporation of the dried (magnesium sulphate) extracts afforded an oil, which was purified by preparative TLC (silica plate; developed with 60% ethyl ether/petroleum ether). The title diol was obtained as a pale yellow oil.

$^1$H NMR (mixture of diasteriomers) CDCl$_3$): 0.29 (s, 9H), 0.35 (s, 9H), 2.2 (br, 2H), 3.70–3.85 (m, 2H), 4.85 (dd, 1H, J=3.9 Hz, 7.3 Hz), 4.95 (m, 2H), 6.50 (d, 1H), 6.65 (s, 1H), 7.60 (d, 1H), and 7.66 (s, 1H).

$^{13}$C NMR (CDCl$_3$): −1.8, −1.0, 66.9, 67.3, 67.7, 108,4, 118.3, 124.3, 134.2, 143.7, 146.5, 156.2 and 161.5.

MS m/e (% abundance): 200 (M+, 18), 169 (100), 153 (22), 139 (9) and 73 (73).

4-(1,2-Didodecanoyloxyethyl)-2-trimethylsilylfuran tert-Butyl lithium (a 1.7M solution in pentane; 0.34 ml, 0.57 mmol) was added dropwise to a solution of 4-(1,2-dihydroxyethyl)-2-trimethylsilylfuran (52 mg, 0.26 mmol) in tetrahydrofuran (1 ml) at 0 degrees under argon. After 5 minutes, lauroyl chloride (0.13 ml, 0.57 mmol) was added and stirring was continued at room temperature for 15 hours. The mixture was quenched with water and extracted with ether. Evaporation of the dried (magnesium sulphate) extracts gave an oil, which was purified by preparative TLC (silica plate; developed with 5% ethyl ether/petroleum ether). The title diester was obtained as a pale yellow oil.

$^1$H NMR (CDCl$_3$): 0.28 (s, 9H), 0.91 (t, 6H, J=6.9 Hz), 1.29 (brs, 32H), 1.60 (m, 4H), 2.35 (m, 4H), 4.35 (m, 2H), 6.12 (m, 1H), 6.69 (s, 1H) and 7.67 (s, 1H).

4-(1,2-Didodecanoyloxyethyl)-5-hydroxy-2(5H)-furanone

A mixture of 4-(1,2-didodecanoyloxyethyl)-2trimethylsilylfuran (97.1 mg, 0.17 mmol) and Rose Bengal (5 mg) in tetrahydrofuran (8 ml) was exposed to singlet oxygen for 2½ hours at −78 degrees. The residue, after solvent removal, was purified by preparative TLC (20x20 cm, 500u silica plate; developed with 60% ethyl ether/petroleum ether). The title diester was obtained as a colorless waxy solid.

$^1$H NMR (CDCl$_3$) 0.89 (t, 6H, J=6.9 Hz), 1.27 (brs, 16H), 1.65 (m, 4H), 2.34 (t, 2H, J=7.6 Hz), 2.41 (t, 2H, J=8.0 Hz), 4.35–4.55 (m, 2H), 5.75 (t, 1H), 6.09 (s, 1H) and 6.15 (s, 1H). $^{13}$C NMR (CDCl$_3$): 14.1, 22.7, 24.8, 28.1, 28.3, 28.5, 28.6, 28.7, 29.1, 29.4, 29.5, 29.6, 31.9, 34.0, 62.7, 67.6, 97.7, 121.0, 161.5, 168.9 and 172.5.

MS m/e exact mass calculated for C$_{30}$H$_{56}$NO7 (M+NH$_4$) 542.4057, found 542.4054.

4-(1,2-Dihydroxyethyl)-2-triethylsilylfuran (prepared substantially as described above using 5-triethylsilyl-3furaldehyde in place of the corresponding trimethylsilyl furaldehyde) is reacted with dodecanoyl chloride in the presence of triethylamine to give 4-(1-hydroxy-2-dodecyanoyloxyethyl)-2-triethylsilylfuran. Treating this 1-hydroxy compound with acetic anhydride and pyridine gives 4-(1-acetoxy-2-dodecanoyl-oxyethyl)-2-triethylsilylfuran.

A mixture of the above prepared furan and Rose Bengal in tetrahydrofuran is exposed to singlet oxygen to give 4-(1-acetoxy-2-dodecanoyloxyethyl)-5-hydroxy-2(5H)-furanone.

Reacting 4-(1,2-dihydroxyethyl)-2-triethyl-silylfuran with acetyl chloride and triethylamine gives 4-(1-hydroxy-2-acetoxyethyl)-2-triethylsilylfuran. Reacting this intermediate with dodecanoyl chloride and triethylamine and oxidizing the resulting 4-(1-dodecanoyloxy-2-acetoxyethyl)-2-triethylsilylfuran gives 4-(1-dodecyanoloxy-2-acetoxyethyl)-5-hydroxy-2(5H)-furanone.

Using methyl methylphosphonochloridate in place of dodecanoyl chloride in the above-described procedure for making 4-(1-acetoxy-2-dodecanoyloxyethyl)-5-hydroxy-2(5H)-furanone, the product obtained is 4-[1-acetoxy-2-OP(0)(CCH$_3$)(CH$_3$) ethyl]-5-hydroxy-2(5H)-furanone.

4-(2-Amino-1-hydroxy)ethyl-2-triethylsilylfuran (Compound 7)

A mixture of 5-triethylsilyl-3-furaldehyde (4.35g, 20.7 mmol), trimethylsilyl cyanide (3.0 ml, 22.7 mmol) and zinc bromide (ca. 10 mg) was stirred under argon at room temperature for 19 hours. After cooled to 0°, lithium aluminum hydride (a 1.0M solution in tetrahydrofuran; 31.0 ml, 31.0 mmol) was added dropwise. Stirring was continued for 3 hours while the cooling bath was warmed to room temperature. The mixture was recooled to 0° and was quenched with dilute sodium hydroxide. After the aluminum salt was coagulated by the addition of sodium sulfate, the mixture was filtered. Evaporation of the filtrate gave a residue which was purified by a silica column using 20% methanol/chloroform/0.2% triethylamine to give the title amino alcohol as a pale yellow solid.

$^1$HNMR(CDCl$_3$): 0.73 (q, 6H, J=8.2 Hz), 0.97 (t, 9H, J=8.2 Hz), 2.05 (br, 3H), 2.87 (dd, 1H, J=7.6 Hz, 12.7 Hz), 3.00 (dd, $^1$H J=12.7 Hz, 4.0Hz), 4.62 (dd, 1H, J=4.0 Hz, 7.4Hz), 6.61 (s, 1H) and 7.61 (s, 1H).

4-(2-Undecanylamido-1-hydroxy)ethyl-2-triethylsilylfuran and 4-(2-undecanylamido-1-dodecanoyloxy)ethyl-2-triethylsilylfuran Dodecanoyl chloride (0.41 ml, 1.76 mmol) was added dropwise to a solution of 4-(2-amino-1-hydroxy)ethyl-2-triethylsilylfuran (Compound 7) (404.7 mg, 1.68 mmol) and triethylamine (0.25 ml, 1.76 mmol) in tetrahydrofuran (4 ml) at 0°. Stirring was continued for 14 hours while the cooling bath attained room temperature. The mixture was evaporated to give a residue which was purified by a silica column using 20% ethyl acetate/hexane. Fractions with $R_f$ of about 0.19 (20% ethyl acetate/hexane) on evaporation gave 4-(2-undecanylamido-1-dodecanoyloxy)ethyl-2-triethylsilylfuran. Further elution of the column with 40% ethyl acetate/hexane gave 4-(2-undecanylamido-1-hydroxy)ethyl-2-triethylsilylfuran ($R_f$ 0.19; 40% ethylacetate/hexane).

4-(2-Undecanylamido-1-dodecanoyloxy)ethyl-2-triethylsilylfuran: $^1$HNMR(CDCl$_3$): 0.75 (q, 6H, J=7.9 Hz), 0.88 (t, 6H, J=6.9 Hz), 0.97 (q, 9H, J=7.4 Hz), 1.25 (br s 32H), 1.60 (m, 4H), 2.15 (t, 2H J=8.0 Hz), 2.33 (t, 2H J=7.6 Hz), 3.68 (m, 2H), 5.65 (br t, 1H), 5.90 (br t, 1H), 6.58 (s, 1H) and 7.63 (s, 1H). MS (m/e % abundance) 606[(M+H)$^+$, 1], 450(2), 424(4), 423(10), 408(10), 407(32), 406(100), 405(5), 224(8), 200(2), 183(2) and 104(2).

4-(2-Undecanylamido-1-hydroxy)ethyl-2-triethylsilylfuran: $^1$HNMR (CDCl$_3$): 0.75 (q, 6H, J=7.9 Hz), 0.89 (t, 3H, J=7.1 Hz), 0.98 (q, 9H, J=7.1 Hz), 1.27 (br s, 16H), 1.65 (m, 2H), 2.21 (t, 2H, J=7.3 Hz), 3.08 (d, 1H, J=3.8 Hz), 3.38 (2dd, 1H, J=15.0 Hz, 7.5 Hz and 6.0 Hz), 3.70 (2dd, 1H, J=15.0 Hz, 7.5 Hz and 3.0 Hz), 4.85 (m, 1H), 5.95 (br t, 1H), 6.62 (s, 1H). HRMS exact mass calculated for C$_{24}$H$_{45}$SiNO$_3$(M+) 423.3169, found 423.3166.

4-(2-Undecanylamido-1-hydroxy)ethyl-5-hydroxy-2(5H)-furanone (Compound 40)

A mixture of 4-(2-undecanylamido-1-hydroxy)ethyl-2-triethylsilylfuran (300 mg, 0.71 mmol), water (a few drops) and Rose Bengal (5 mg) in acetone (7 ml) was exposed to singlet oxygen at 0° for 1 hour. The residue, after solvent removal, was purified on preparative silica plates (developed with 5% methanol/dichloromethane) to give the title furanone.

$^1$HNMR(CD$_3$OD): 0.90 (br t, 3H), 1.29 (br s, 16H), 1.55 (m, 2H), 2.19 (t, 2H, J=7.3 Hz), 3.50 (br m, 2H), 4.60 (br, 1H), 6.06 (s, 1H) and 6.15 (br s, 1H).

$^{13}$CNMR(CD$_3$OD): 14.5, 23.7, 23.9, 27.0, 27.1, 29.8, 29.9, 30.0, 30.2, 30.4, 30.6, 30.7, 31.1, 31.3, 33.0, 33.2, 36.9, 44.4, 44.5, 44.6, 68.2, 100.3, 100.4, 119.6, 171.2, 172.6 and 176.9. HRMS exact mass calculated for C$_{18}$H$_{31}$NO$_5$ (M+) 342.2280 found 342.2293.

4-(1-Acetoxy-2-undecanylamido)ethyl-2-triethylsilylfuran

A mixture of 4-(2-undecanylamido-1-hydroxy)ethyl-2-triethylsilylfuran (244.3 mg, 0.58 mmol), acetic anhydride (0.5 ml) and pyridine (0.5 ml) was stirred at room temperature for 16 hours. After most of the solvent was removed, the residue was purified by preparative silica TLC using 60% ethyl ether/hexane to give the title ester as a colorless solid.

$^1$HNMR(CDCl$_3$): 0.77 (q, 6H, J=7.5 Hz), 0.91 (t, 3H, J=6.8 Hz), 1.00 (t, 9H, J=7.3 Hz), 1.29 (br s, 16H), 1.60 (m, 2H), 2.13 (s, 3H), 2.19 (t, 2H, J=7.9 Hz), 3.70 (m, 2H), 5.70 (br t, 1H), 6.95 (m, 1H), 6.63 (s, 1H) and 7.67 (s, 1H). HRMS exact mass calculated for C$_{26}$H$_{47}$NO$_4$Si(M+) 465.3274, found 465.3283.

4-(1-Acetoxy-2-undecanylamido)ethyl-5-hydroxy-2(5H)-furanone (Compound 41)

A mixture of 4-(1-acetoxy-2-undecanylamido)ethyl-2-triethylsilylfuran (160 mg, 0.34 mmol), water (a few drops) and Rose Bengal (3 mg) in acetone (7 ml) was exposed to singlet oxygen at 0° for 2 hours. The residue, after solvent removal, was purified by preparative silica plates (developed with 40% ethyl acetate/hexane) to give the title furanone.

$^1$HNMR(CDCl$_3$): 0.89 (t, 3H, J=6.8 Hz), 1.27 (br s, 16H), 1.65 (m, 2H), 2.18 (s, 3H), 2.20 (m, 2H), 3.35 (br m, 1H), 4.25 (br m, 1H), 5.60 (brs, 1H), 5.95 (br s, 1H), 6.10 (m, 1H), 6.20 (m, 1H) and 7.20 (br m, 1H).

$^{13}$CNMR(CDCl$_3$): 14.0, 20.7, 22.6, 25.6, 25.7, 28.8, 28.9, 29.1, 29.2, 29.4, 29.5, 29.8, 31.8 36.2, 40.9, 41.0, 41.1, 50.5, 69.3, 69.4, 69.5, 98.7, 120.2, 120.3, 120.4, 169.5, 169.7, 175.9, 176.0 and 176.1

HRMS exact mass calculated from C$_{20}$H$_{34}$NO$_6$(M+) 384.2386, found 384.2381.

4-(2-Undecanylamido-1-dodecanoyloxy)ethyl-5-hydroxy-2(5H)-furanone (Compound 42)

A mixture of 4-(2-undecanylamido-1-dodecanoyl)ethyl-2-triethylsilylfuran (145 mg, 0.24 mmol), Rose Bengal (ca. 5 mg) and a few drops of water in tetrahydrofuran (7 ml) was exposed to singlet oxygen at 0° for 1 hour. The residue, after solvent removal, was purified by preparative silica TLC plates using 40% ethyl acetate/hexane to give the title furanone as a pale yellow oil.

$^1$HNMR(CDCl$_3$): 0.93 (t, 6H, J=7.0 Hz), 1.31 (br s, 32H), 1.60 (m, 4H), 2.25 (m, 2H), 2.40 (t, 2H, J=7.6 Hz), 3.35 (2 br t, 1H), 4.30 (m, 1H), 5.64 (br s, 1H), 5.96 (s, 1H), 6.05–6.20 (m, 3H) and 7.65 (br m 1H). MS (m/e, % abundance): 523(M+, 15), 522 (13), 521 (24), 339 (12), 326 (12), 324 (16), 310 (25), 309 (21), 308 (100), 307 (19), 306 (28), 264 (18), 218 (23), 201 (71), 200 (64), 183 (60), 181 (43), 126 (81), 125 (67), 98 (43) and 83 (39).

4-(1-Hydroxy-2-dodecanesulfonylamido)ethyl]-2-triethylsilylfuran

A mixture of 4-(2-amino-1-hydroxy)ethyl-2-triethylsilylfuran (Compound 7, 694.2 mg, 2.88 mmol), dodecanesulfonyl chloride (930 mg, 3.45 mmol) and triethylamine (0.48 ml, 3.45 mmol) in tetrahydrofuran (10 ml) was stirred at room temperature for 2 days. The mixture was quenched with water and was extracted with ethyl ether. Evaporation of the dried (magnesium sulfate) extracts gave an oil, which was purified by a silica column using 55% ethyl ether/hexane to give the title compound.

$^1$HNMR(CDCl$_3$): 0.76 (q, 6H, J=8.0 Hz), 0.88 (t, 3H, J=6.9 Hz), 0.98 (t, 9H, J=8.0 Hz), 1.26 (m, 16H), 1.38 (m, 2H), 1.81 (m, 2H), 2.21 (m, 1H), 3.0 (m, 2H), 3.35 (m, 2H), 4.62 (m, 1H), 4.85 (m 1H), 6.61 (s, 1H) and 7.65 (s, 1H).

$^{13}$CNMR(CDCl$_3$): 3.0, 7.1, 13.9, 22.5, 23.4, 28.2, 29.0, 29.1, 29.2, 29.4, 29.5, 31.8 49.3, 52.6, 66.4, 119.0, 125.3, 143.7 and 159.4. HRMS exact calculated for C$_{24}$H$_{47}$NO$_4$SSi:(M+) 473.2995 found 473.3004.

4-[(1-Hydroxy-2-dodecanesulfonylamido)ethyl]-5-hydroxy-2(5H)-furanone

A mixture of 4-[(1-hydroxy-2-dodecanesulfonylamido)ethyl]-2-triethylsilylfuran (200 mg, 0.42 mmol), water (a few drops) and Rose Bengal (5 mg) in acetone (10 ml) was exposed to singlet oxygen at 0° for 2 hours. The residue, after solvent removal, was purified by preparative silica plates (developed with 20% methanol/dichloromethane) to give the titled furanone.

¹HNMR(CDCl₃): 0.88 (t, 3H, J=6.9 Hz), 1.26 (m, 18H), 1.75 (m, 2H), 3.05 (m, 2H), 3.30 (m, 1H), 3.42 (m, 1H), 4.69 (br, 1H), 6.20 (br, 1H) and 6.29 (br, 1H).

¹³CNMR(CDCl₃): 13.9, 22.5 23.3, 28.2, 29.1, 29.2, 29.3, 29.5, 31.7, 46.3, 46.4, 52.6, 67.3, 67.4, 98.3, 98.4, 119.9, 167.0, 168.0, 172.2 and 172.3.

HRMS exact mass calculated for $C_{18}H_{35}N_2O_5S[(M+NH_4)-H_2O]$ 391.2267, found 391.2249.

4-[1-Acetoxy-2-(dodecansulfonylamido)ethyl]-2-triethylsilylfuran

A mixture of 4-[1-hydroxy-2-(dodecansulfonylamido)ethyl]-2-triethylsilylfuran (228 mg, 0.48 mmol), acetic anhydride (55 ul, 0.58 mmol) and pyridine (47 ul, 0.58 mmol) in dichloromethane (5 ml) was stirred at room temperature for 14 hours. After most of the solvent was removed, the residue was redissolved in ether and washed with aqueous copper sulfate and water. Evaporation of the dried (magnesium sulfate) organic phase gave an oil, which was purified by a silica column using 45% ethyl ether/hexane to give the titled ester.

¹HNMR(CDCl₃): 0.76 (q, 6H, J=7.4 Hz), 0.88 (t, 3H, J=5.9 Hz), 0.97 (t, 9H, J=7.4 Hz), 1.25 (m, 18H), 1.76 (m, 2H), 2.10 (s, 3H), 2.97 (m, 2H), 3.50 (t, 2H, J=5.9 Hz), 4.30 (m, 1H), 5.87 (t, 1H, J=5.9 Hz), 6.59 (s, 1H) and 7.66 (s, 1H).

4-[1-Acetoxy-2-(dodecanesulfonylamido)ethyl]-5-hydroxy-2(5H)-furanone (Compound 43)

A mixture of 4-[1-acetoxy-2-dodecanesulfonylamido)ethyl]-2-triethylsilylfuran (196 mg, 0.38 mmol), water (2 drops) and Rose Bengal (5 mg) in acetone (15 ml) was exposed to singlet oxygen at 0° for 2 hours. The residue, after solvent removal, was purified by preparative silica plates (developed with 10% methanol/chloroform) to give the title furanone.

¹HNMR(CDCl₃): 0.88 (t, 3H, J=6.4 Hz), 1.25 (m, 18H), 1.75 (m, 2H), 2.17 (s, 3H), 3.0 (m, 2H), 3.57 (br s, 2H), 5.60 (m, 1H), 6.16 (s, 1H) and 6.18 (s, 1H).

¹³CNMR(CDCl₃): 14.1, 18.2, 20.7, 22.6, 23.5, 28.2, 29.0, 29.1, 29.3, 29.5, 29.6, 29.8, 44.4, 53.4, 58.4, 69.1, 98.1 121.2, 162.7, 169.9 and 170.1.

LRMS (m/e, % abundance) 391 (M+, 28), 390(15), 389(37), 376(23), 375(100), 374(12), 358(38), 356(18), 328(23), 327(12), 312(14), 268(14), 267(84), 252(49), 208(28), 207(11), 201(15) and 185(15).

4-(1-Hydroxy-2-(10-carboxydecaneamido)]ethyl-2-triethylsilylfuran

A mixture of 4-(2-amino-1-hydroxy)ethyl-2-triethylsilylfuran (Compound 7, 208.0 mg, 0.86 mmol), dodecanedioic acid (199.0 mg, 0.86 mmol), dicyclohexylcarbodiimide (178 mg, 0.86 mmol) and 4-dimethylaminopyridine (105 mg, 0.86 mmol) in dichloromethane (5 ml) was stirred at room temperature for 16 hours. The mixture was quenched with dilute hydrochloric acid and was extracted with ethyl acetate. Evaporation of the dried (magnesium sulfate) extracts gave a residue, which was purified by a silica column using 5% methanol/chloroform to give the title furan.

¹HNMR(CDCL₃): 0.76 (q, 6H, J=8.0 Hz), 0.97 (t, 9H, J=8.0 Hz), 1.29 (br s, 12H), 2.21 (t, 2H, J=7.9 Hz), 2.35 (t, 2H, J=7.2 Hz), 3.35 (m, 1H), 3.60 (m, 1H), 4.83 (dd, 1H, J=7.8 Hz, 3.0 Hz), 6.10 (t, 1H, J=2.9 Hz), 6.61 (s, 1H) and 7.62 (s, 1H).

¹³CNMR(CDCl₃): 3.1, 7.2, 24.6, 24.7, 24.8, 25.6, 28.8, 28.9, 29.0, 29.1, 33.6, 34.0, 36.5, 46.2, 66.5, 119.1, 126.0, 143.5, 159.6, 174.8 and 178.4.

HRMS exact mass calculated for $C_{24}H_{43}SiNO_5(M^+)$ 453.2911, found 453.2913.

4-[(1-Hydroxy-2-(10-carboxydecaneamido)]ethyl-5-hydroxy-2(5H)-furanone

A mixture of 4-[(1-hydroxy-2-(10-carboxydecaneamido)]ethyl-2-triethylsilylfuran (15 mg, 0.19 mmol), water (a few drops) and Rose Bengal (5 mg) in acetone (7 ml) was exposed to singlet oxygen at 0° for 2 hours. The residue, after solvent removal, was purified by a silica column using 10% methanol/chloroform to give the title furanone.

¹H NMR (CDCl₃): 1.29 (m, 12H), 1.60 (m, 4H), 2.18 (t, 2H, J=7.0 Hz), 2.27 (t, 2H, J=7.4 Hz), 3.40 (m 1H), 3.55 (m, 2H), 6.03 (br, 1H), and 6.19 (br, 1H).

¹³CNMR(CDCl₃): 6.0, 27.0, 30.1, 30.2, 30.3, 30.4, 30.5, 34.9, 36.9, 44.4, 49.7, 68.4, 99.7, 119.4, 172.0, 172.6, 176.9 and 177.7.

LRMS (m/e, % abundance) 371 (M+, 32), 355(17), 358(38), 249(14), 248(100), 230(41) and 229(11).

4-[(1-Acetoxy-2-(10-carboxydecaneamido)]ethyl-2-triethylsilylfuran

A mixture of 4-[(1-hydroxy-2-(10-carboxydecaneamido)]ethyl-2-triethylsilylfuran (53.4 mg, 0.12 mmol), triethylamine (60 ul, 0.45 mmol) and acetic anhydride (42 ul, 0.45 mmol) in dichloromethane (5 ml) was stirred at room temperature for 14 hours. The mixture was quenched with dilute hydrochloric acid and was extracted with ethyl acetate. Evaporation of the dried (magnesium sulfate) extracts gave an oil, which was purified by a silica column using 5% methanol/chloroform to give the title furanone.

¹HNMR(CDCl₃): 0.76 (q, 6H, J=8.0 Hz), 0.97 (t, 9H, J=8.0 Hz), 1.27 (m, 16H), 1.63 (m, 4H), 2.09 (s, 3H), 2.16 (t, 2H, J=8.0 Hz), 2.34 (t, 2H, J=7.4 Hz), 3.67 (m, 2H), 5.76 (br t, 1H), 5.90 (dd, 1H, J=7.2 Hz, 5.0 Hz), 6.59 (s, 1H) and 7.64 (s, 1H).

¹³CNMR(CDCl₃): 2.9, 7.0, 20.9, 24,5, 24,7, 25.3, 25.4, 28.6, 28 7, 28.9, 33.4, 33.8, 36.5, 43.1, 67.7, 119.5, 122.1, 144.9, 160.3, 171.0, 173.8 and 178.9.

HRMS exact mass calculated for $C_{26}H_{45}NO_6Si(M^+)$ 495.3016, found 495.2997.

4-[(1-Acetoxy-2-(10-carboxydecaneamido)]ethyl-5-hydroxy-2(5H)-furanone (Compound 44)

A mixture of 4-[(1-acetoxy-2-(10-carboxydecaneamido)]ethyl-2-triethylsilylfuran (53.6 mg, 0.12 mmol), water (a few drops) and Rose Bengal (3 mg) in acetone (7 ml) was exposed to singlet oxygen at 0° for 2 hours. The residue, after solvent removal, was purified by preparative silica plates (developed with 10% methanol/chloroform) to give the title furanone.

¹HNMR(CDCl₃): 1.26 (m, 12H), 2.55 (m, 4H), 2.15 (m, 5H), 2.35 (t, 2H, J=7.3 Hz), 3.35 (m, 1H), 3.45 (br, 1H), 3.90 (br, 1H), 4.20 (m, 1H), 5.59 (br, 1H), 5.65 (br, 1H), 5.97 (br, 1H), 6.00 (br, 1H) 6.10 (br, 1H), 6.15 (br, 1H), 6.30 (br, 1H) and 6.40 (br, 1H).

$^{13}$CNMR(CDCl$_3$) 20.8, 24.6, 25.5, 28.8, 29.0, 29.1, 29.3, 33.8, 36.3, 41.4, 69.8, 98.6, 120.4, 163.1, 169.1, 169.2, 176.0 and 178.8.

LRMS (m/e % abundance) 395[(M+-H$_2$O), 0.4], 369(7), 355(10), 354(14), 353(40), 336(12), 249(14), 248(100) and 230(29).

N-(Methanesulfonyl)piperazine

A mixture of methanesulfonyl chloride (1.85 ml, 24 mmol) and piperazine (2.06 g, 24 mmol) in dichloromethane (60 ml) was stirred at room temperature for 14 hours. The mixture was basified with aqueous sodium hydroxide and filtered. The filtrate was washed with water, dried (magnesium sulfate) and evaporated down to give the title sulfonamide.

$^1$HNMR(CDCl$_3$): 1.75 (br s, 1H), 2.78 (s, 3H), 2.97 (t, 4H, J=5.1 Hz) and 3.19 (t, 4H, J=7.5 Hz).

LRMS (m/e, % abundance) 165[(M+H)$^+$, 7), 164(M+, 5), 85(100) and 56(68).

4-[1-Hydroxy-2-(N'-methanesulfonyloioerazine)amido-1ethyl-2-triethylsilylfuran and 4-1-hydroxy-2-(N',N'-diethyl)amido]ethyl-2-triethylsilylfuran Phosgene (a 20% solution in toluene; 0.46 ml, 0.90 mmol) was added dropwise to a mixture of N-(methanesulfonyl)piperazine (147.4 mg, 0.90 mmol) and triethylamine (0.13 ml, 0.90 mmol) in dichloromethane (3 ml) at room temperature. After 1 hour, 4-(2-amino-1-hydroxy)ethyl-2-triethylsilylfuran (Compound 7, 217 mg, 0.90 mmol) was added. Stirring was continued at room temperature for 14 hours. The mixture was quenched with water and was extracted with ethyl acetate. Evaporation of the dried (magnesium sulfate) extracts gave a residue, which was purified by a silica column using 80% ethyl acetate/hexane to give 4-[1-hydroxy-2-(N',N'-diethyl)amido]-methanesulfonyl-piperazine)amido]-ethyl-2-triethylsilylfuran (R$_f$ 0.27, 80% ethylacetate/hexane). Subsequent elution with ethyl acetate gave 4-[1-hydroxy-2-(N'-methanesulfonyl-piperazone)amido]-ethyl-2-triethylsilylfuran (R$_f$ 0.21; ethyl acetate/hexane).

4-[1-Hydroxy-2-(N'-methanesulfonyl-piperazine)amido]ethyl-2-triethylsilylfuran,
$^1$HNMR(CDCl$_3$): 0.79 (q, 6H, J=8.0 Hz), 1.00 (t, 9H, J=8.1 Hz), 1.70 (br, 1H), 2.83 (s, 3H), 3.26 (t, 4H, J=4.8 Hz), 3.40 (m, 1H), 3.55 (t, 4H, J=4.8 Hz), 3.60 (m, 1H), 4.84 (dd, 1H, J=7.9 Hz, 3.2 Hz), 5.03 (br, 1H), 6.64 (s, 1H) and 7.65 (s, 1H). HRMS exact mass calculated for C$_{18}$H$_{33}$N$_2$O$_5$SSi(M+) 431.1910, found 431.1895.

4-[1-Hydroxy-2-(N',N'-diethyl)amido]ethyl-2-triethylsilylfuran $^1$HNMR(CDCl$_3$): 0.73 (q, 6H, J=7.5 Hz), 1.00 (t, 9H, J=7.4 Hz), 1.16 (t, 6H, J=7.1 Hz), 3.30 (q, 4H, J=7.1 Hz), 3.40 (m, 1H), 3.65 (m, 1H), 4.33 (d, 1H, J=4.1 Hz), 4.80 (br t+m, 2H), 6.65 (s, 1H) and 7.64 (s, 1H). HRMS exact mass calculated for C$_{17}$H$_{32}$N$_2$O$_3$Si(M+) 340.2182, found 340.2171.

4-[1-Dodecanoyloxy-2-(N'-methanesulfonyl-piperazine)amido]ethyl-2-triethylsilyfuran A mixture of 4-[1-hydroxy-2-(N'-methanesulfonyl-piperazine)amido]-ethyl-2-triethylsilylfuran 100 mg, 0.23 mmol), dodecanoyl chloride (95 ul, 0.41 mmol) and triethylamine (40 ul, 0.28 mmol) in dichloromethane (7 ml) was stirred at room temperature for 14 hours. The mixture was quenched with water and was extracted with ethyl acetate. Evaporation of the dried (magnesium sulfate) extracts gave an oil, which was purified by preparative silica plates (developed with 45% ethylacetate/hexane) to give the title furan.

$^1$HNMR(CDCl$_3$): 0.76 (q, 6H, J=8.0 Hz), 0.88 (t, 3H, J=6.0 Hz), 0.97 (t, 9H, J=8.0 Hz), 1.25 (m, 14H), 2.34 (t, 2H, J=7.6 Hz), 2.79 (s, 3H), 3.21 (t, 4H, J=4.9 Hz), 3.46 (m, 4H), 3.65 (m, 2H), 4.92 (br t, 1H), 5.94 (dd, 1H, J=8.0 Hz, 4.0 Hz), 6.59 (s, 1H) and 7.64 (s, 1H).

$^{13}$CNMR(CDCl$_3$): 3.1, 7.2, 14.0, 22.6, 24.9, 29.0, 29.2, 29.4, 29.5, 31.8, 34.5, 43.6, 45.4, 45.5, 68.1, 119.3, 122.1, 144.4, 156.8, 159.9 and 173.9.

HRMS exact mass calculated for C$_{30}$H$_{55}$N$_3$O$_6$SSi(M+) 413.3581, found 413.3562.

-[1-Dodecanoyloxy-2-(N'-methanesulfonyl-piperazine)amido1ethyl-5-hy (Compound 45)

A mixture of 4-[1-dodecanoyloxy-2(N'-methanesulfonylpiperazine)amido]ethyl-2-triethylsilylfuran (61 mg, 0.11 mmol), water (a few drops) and Rose Bengal (3 mg) in acetone (7 ml) was exposed to singlet oxygen at 0° for 2 hours. The residue, after solvent removal, was purified by a silica column using 7.5% methanol/chloroform to give the title furanone.

$^1$HNMR(CDCl$_3$): 0.88 (t, 3H, J=6.9 Hz), 1.26 (m, 16H), 1.61 (m, 2H), 2.40 (t, 2H, J=6.9 Hz), 2.80 (s, 3H), 3.19 (t, 4H, J=5.0 Hz), 3.50 (m, 5H), 4.18(m, 1H), 5.05 (m, 1H), 5.56 (br d, 1H, J=1.3 Hz), 5.90 (br, 1H), 6.12 (br, 1H) and 7.65 (m, 1H).

$^{13}$CNMR(CDCl$_3$): 14.5, 23.0, 25.1, 29.5, 29.6, 29.7 29.8, 30.0, 32.2, 34.4, 35.1, 43.1, 44.1, 45.7, 70.1, 99.3, 120.6, 158.0, 169.8, 169.9 and 172.6. HRMS exact mass calculated for C$_{24}$H$_{40}$N$_3$O$_7$S (M+-OH) 514.2587, found 514.2591.

4-[1-Dodecanoyloxy-2-N',N'-diethyl)amido]ethyl-2-triethylsilylfuran

A mixture of 4-[1-hydroxy-2-(N',N'-diethyl)amido]ethyl-2-triethylsilylfuran (80 mg, 0.24 mmol), dodecanoyl chloride 65 ul, 0.28 mmol) and triethylamine (40 ul, 0.28 mmol) in dichloromethane (7 ml) was stirred at room temperature for 14 hours. The mixture was quenched with water and was extracted thoroughly with ethyl acetate. Evaporation of the dried (magnesium sulfate) extracts gave an oil, which was purified by preparative silica plates (developed with 60% ethyl ether/hexane) to give the title furan.

$^1$HNMR(CDCl$_3$): 0.75 (q, 6H, J=8.0 Hz), 0.88 (t, 3H, J=7.0 Hz), 0.96 (t, 9H, J=8.0 Hz), 1.10 (t, 6H, J=7.2 Hz), 1.25 (m, 14H), 1.58 (m, 4H), 2.33 (t, 2H, J=7.7 Hz), 3.22 (q, 4H, J=7.2 Hz), 3.64 (m, 2H), 4.61 (br t, 1H), 5.93 (dd, 1H, J=7.4 Hz, 4.8 Hz), 6.61 (s, 1H) and 7.64 (s, 1H).

$^{13}$CNMR(CDCl$_3$): 2.8, 6.9, 13.5, 13.8, 22.4, 24.8, 28.9, 29.0, 29.1, 29.2, 29.4, 31.7, 34.3, 41.1, 44.8, 68.1, 119.6, 122.6, 144.8, 157.2, 159.9 and 173.9.

HRMS exact mass calculated for C$_{29}$H$_{54}$N$_2$O$_4$Si (M+) 522.3853, found 522.3859.

4-[1-Dodecanoyloxy-2-(N',N'-diethyl)carboxyamido]ethyl-5-hydroxy-2(5H)-furanone (Compound 46)

A mixture of 4-[1-dodecanoyloxy-2-(N',N'-diethyl)amido]ethyl-2-triethylsilylfuran (39.5 mg, 0.07 mmol), water (a few drops) and Rose Bengal (5 mg) in acetone (6 ml) was exposed to singlet oxygen at 0° for 2 hours. The residue, after solvent removal, was purified by a silica column using 10% methanol/chloroform to give the title furanone.

¹HNMR(CDCl₃): 0.79 (t, 3H, J=6.2 Hz), 1.18 (m, 16H), 1.56 (t, 2H, J=7.3 Hz), 1.74 (p, 2H, J=7.5 Hz), 2.13 (t, 2H, J=7.5 Hz), 2.19 (t, 2H, J=7.5 Hz), 2.55 (t, 1H), 3.50 (br m, 2H), 5.64 (br, 1H), 5.99 (br, 1H) and 6.11 (br, 1H).

¹³CNMR(CDCl₃) 14.4, 22.3, 23.7, 25.8, 30.2, 30.4, 30.5, 30.6, 30.8, 33.1, 34.1, 34.8, 35.9, 41.9, 70.0, 100.0, 120.4, 166.3, 171.9, 174.0 and 176.0.

EXAMPLE 8

2-Triethylsilyl-4-vinylfuran n-Butyl lithium (a 2.5M solution in hexane; 4.4 ml, 11.0 mmol) was added dropwise to a suspension of methyltriphenylphosphonium bromide (3.93 g, 11 mmol) in THF (40 ml) at 0 degrees C. under argon. After 2 hours stirring at 0 degrees C., a solution of 2-triethylsilyl-4-furaldehyde (1.54 g, 7.33 mmol) in THF (2 ml) was added. Stirring was continued at room temperature for 14 hours and the mixture was quenched with methanol/water 40 ml (1:1). Extraction (pentane) and evaporation of the dried (magnesium sulfate) extracts gave a residue, which was purified by flash chromatography on silica using pentane to give the titled furan. $R_f$(pentane) 0.75.

¹H NMR (CDCl₃) 0.81 (q, 6H, J=8.1 Hz), 0.99 (t, 9H, J=7.4 Hz), 5.14 (d, 1H, J=12.1 Hz), 5.48 (d, 1H, J=17.6 Hz), 6.64 (dd, 1H, J=10.8 Hz, 17.5 Hz), 6.81 (s, 1H) and 7.64 (s, 1H). HRMS exact mass calculated for $C_{12}H_{20}SiO(M^+)$ 208.1283, found 208.1280.

4-(1,2-Dihydroxyethyl)-2-triethylsilylfuran (Compound 6)

2-Triethylsilyl-4-vinylfuran (1.20g, 6.25 mmol) was added to a mixture of 4-methylmorpholine N-oxide (788.0 mg, 6.70 mmol) osmium tetroxide (a 2.5% by weight solution in tertbutanol; 0.50 ml), water (1.5 ml) and acetone (1.5 ml) at room temperature. After stirring for 14 hours, the mixture was acidified to pH=1 with dilute sulfuric acid. Extraction (ethyl acetate) and evaporation of the dried (magnesium sulfate) extracts gave an oil, which was purified by flash chromatography on silica using 40% ethyl acetate/hexane to give the titled diol. $R_f$(40% ethyl acetate/hexane) 0.11.

¹H NMR (CDCl₃) 0.80 (q, 6H, J=7.5 Hz), 0.98 (t, 9H, J=7.5 Hz), 1.65 (br, 2H), 3.75 (m, 2H), 4.82 (dd, 1H, J=7.4 Hz, 3.9 Hz), 6.66 (s, 1H) and 7.68 (s, 1H).

HRMS exact mass calculated for $C_{12}H_{22}O_3Si(M^+)$ 242.1338, found 242.1344.

4-(1,2-Diazidoethyl)-2-triethylsilylfuran

A solution of diphenylphosphoryl azide (0.87 ml, 4.04 mmol) in THF (1 ml) was added over a period of 15 minutes to a solution of 4-(1,2-dihydroxyethyl)-2-triethylsilylfuran (490 mg, 2.02 mmol), triphenylphosphine (1.06 g, 4.04 mmol) and diethylazidodicarboxylate (703 mg, 4.04 mmol) in THF (10 ml). Stirring was continued at room temperature for 2 days. The mixture was evaporated in the presence of a minimum amount of silica gel and the residue was purified by flash chromatography on silica using 10% ethyl ether/hexane to give the titled azide. $R_f$(10% ethyl ether/hexane) 0.48.

¹H NMR (CDCl₃) 0.78 (q, 6H, J=8.0 Hz), 0.98 (t, 9H, J=8.0 Hz), 3.49 (d, 2H, J=6.0 Hz), 4.62 (t, 1H, J=6.0 Hz), 6.62 (s, 1H) and 7.70 (s, 1H).

4-(1,2-Diaminoethyl)-2-triethylsilylfuran (Compound 8)

A solution of lithium aluminum hydride (a 1.0M solution in THF; 1.16 ml, 1.16 mmol) was added dropwise to a solution of 4-(1,2-diazidoethyl)-2-triethylsilylfuran (153.6 mg, 0.53 mmol) in THF (5 ml) at 0 degrees C. under argon. After stirring at room temperature for 2 hours, the mixture was recooled to 0 degrees C. and quenched slowly with 2M sodium hydroxide. The mixture was filtered and the filtrate was extracted thoroughly with ethyl acetate. Evaporation of the dried (magnesium sulfate) extracts gave an oil, which was purified by a silica column using 10% methanol/chloroform/ammonia to give the titled diamine.

¹H NMR (CDCl₃) 0.76 (q, 6H, J=8.0 Hz), 0.98 (t, 9H, J=7.3 Hz), 1.00 (br, 4H), 2.78 (dd, 1H, J=12.6 Hz, 6.8 Hz), 2.89 (dd, 1H, J=12.6 Hz, 5.1 Hz), 3.86 (t, 1H, J=6.4 Hz), 6.60 (s, 1H) and 7.56 (s, 1H).

An alternative synthetic route for the preparation of Compound 8 starts with 2-triethylsilyl-4-furaldehyde, to which sodium cyanide and ammona/ammonium chloride are added, followed by reduction of the resulting intermediate 2-triethylsilyl-4-(amino-cyanomethyl)-furan with lithium aluminum hydride, to yield the title compound.

EXAMPLE 9

Bis-(2-triethylsilyl-4-furyl)methyl]oxalate

Oxalyl chloride (0.59 ml, 6.79 mmol) was added dropwise to a solution of 4-hydroxymethyl-2-triethylsilylfuran (Compound 1, 1.2 g, 5.66 mmol) and triethylamine (0.95 ml, 6.79 mmol) in dichloromethane (10 ml) at 0°. After 10 minutes, the reaction mixture was quenched with ice. Extraction (dichloromethane) and evaporation of the dried (magnesium sulfate) extracts gave an oil, which was purified by flash chromotograhy on silica using 5% ethyl ether/hexane. Fractions with $R_f$ of about 0.17 gave, after evaporation the title oxalate ester as a colorless oil.

¹HNMR (CDCl₃) 0.81 (q, 6H, J=7.3 Hz), 1.02 (t, 9H, J-7.3 Hz), 5.24 (s, 2H), 6.73 (s, 1H) and 7.78 (s, 1H).

MS m/e (% abundance) 195(100), 167(16), 115(35) and 87(29).

4-Iodomethyl-2-triethylsilylfuran (Compound 9)

A mixture of bis-[(2-triethylsilyl-4-furyl)methyl]oxalate (823 mg, 1.72 mmol) and sodium iodide (5.36 g, 35.8 mmol) acetone (7 ml) was stirred at room temperature for 1 day and quenched with water. Extraction (pentane) and evaporation of the dried (magnesium sulfate) extracts gave the titled iodide, which was used in the next step without further purification.

4-Dodecanthiolmethyl-2-triethylsilylfuran

Dodecanthiol (0.52 ml, 2.19 mmol) was added dropwise to a suspension of potassium hydride (88 mg, 2.19 mmol) in tetrahydrofuran (10 ml) at room temperature under argon. After 3 hours, hexamethylphosphoramide (2 ml), followed by a solution of 4-iodomethyl-2-triethylsilylfuran (Compound 9, 470 mg, 1.45 mmol) in tetrahydrofuran (2 ml) was added. Stirring was continued for 8 days at room temperature and the reaction mixture was quenched with water. Extraction (ethyl ether) and evaporation of the dried (magnesium sulfate) extracts gave a residue, which was purified by flash chromatography on silica using 5% ethyl ether/hexane. Fractions with $R_f$ of about 0.18 gave after evaporation the title thioether as a colorless oil.

¹HNMR (CDCl₃) 0.76 (q, 6H, J=7.7 Hz), 0.79 (t, 3H, J=6.7 Hz), 0.98 (t, 9H, J=7.3 Hz), 1.28 (br s, 18H), 1.55

(m, 2H) 2.47 (t, 2H, J=7.6 Hz), 3.58 (s, 2H), 6.66 (s, 1H) and 7.56 (s, 1H).

HRMS exact mass calculated for C$_{23}$H$_{44}$SSiO(M+) 396.2882, found 396.2885.

4-Dodecanethiomethyl-5-hydroxy-2(5H)-furanone (Compound 47)

A mixture of 4-dodecanthiomethyl-2-triethylsilylfuran (180 mg, 0.46 mmol), water (0.01 ml) and Rose Bengal (ca. 3 mg) in tetrahydrofuran (6 ml) was exposed to singlet oxygen at 0° for 1 hour. The residue, after solvent removal, was purified by chromatography on preparative silica thin layer plates (developed with 60% ethyl ether/hexane) to give the title furanone as a pale yellow oil.

$^1$HNMR (CDCl$_3$) 0.91 (t, 3H, J=6.9 Hz), 1.29 (br s, 18H), 1.61 (m, 2H), 2.52 (t, 2H, J=7.2 Hz), 3.50 (br, 2H), 5.85 (br, 1H), 6.00 (s, 1H) and 6.28 (s, 1H).

$^{13}$CNMR (CDCl$_3$) 14.1, 22.6, 27.6, 28.7, 28.9, 29.2, 29.3, 29.5, 29.6, 31.9, 32.1, 98.3, 118.8, 165.7 and 171.5.

HRMS exact mass calculated for C$_{17}$H$_{30}$SO$_3$(M+) 314.1915, found 314.1911.

4-(Dodecanesulfoxomethyl)-5-hydroxy-2(5H)-furanone

A mixture of 4-dodecanethiomethyl-5-hydroxy-2-(5H)-furanone (Compound 47, 36.1 mg, 0.12 mmol) and 30% hydrogen peroxide (1 ml) in methanol (1.5 ml) was stirred at room temperature for 18 hours. Most of the solvent was removed and the residue was purified by chromatography on preparative silica thin layer plates (developed with ethyl acetate) to give the title furanone.

$^1$HNMR (CDCl$_3$) 0.89 (t, 3H), 1.25 (br s, 18H), 1.75 (m, 2H), 2.85 (m, 2H), 3.75 (m, 1H), 4.00 (m, 1H) and 6.20 (m, 2H).

HRMS exact mass calculated for C$_{17}$H$_{31}$O$_4$S (M+H)+ 331.1943, found 331.1947.

4-(Dodecylsulfonylmethyl)-5-hydroxy-2(5H)-furanone

Oxidizing 4-dodecylthiomethyl-2-triethylsilylfuran with potassium peroxymonosulfate gives 4-dodecylsulfonylmethyl-2triethylsilylfuran. Treatment of this intermediate with singlet oxygen and using Rose Bengal as initiator gives the title compound.

EXAMPLE 10

(E)(Z)-Methyl 3-(2-triethylsilyl-4-furyl)propen-2-oate (Compound 10) and (E)(Z) Methyl 3-(2-trimethylsilyl-4-furyl)propen-2-oate Compound 10 and the corresponding trimethylsilyl derivative are prepared as described above in EXAMPLE 5.

3-(2-triethylsily-4-furyl)propan-1-ol and 3-(2-trimethylsily-4-furyl)propan-1-ol These compounds are prepared as described above in EXAMPLE 5.

3-(2-Trimethylsilyl-4-furyl)propyl dodecanoate

Pyridine (0.06 ml, 0.72 mmol) was added to a mixture of 3-(5-trimethylsilyl-3-furyl)propan-1-ol (from above) and lauroyl chloride (0.17 ml, 0.72 mmol) in tetrahydrofuran (4 ml) at room temperature. After 14 hours, the mixture was diluted with ether (10 ml) and washed successively with water, copper (II) sulphate and brine. Evaporation of the dried (magnesium sulphate) organic layers gave an oil, which was purified by preparative TLC (20×20 cm, 500u silica plate; developed with 10% ethyl ether/petroleum ether). The title ester was obtained as a colorless oil.

$^1$H NMR (CDCl$_3$): 0.28 (s, 9H), 0.92 (t, 3H, J=7.3 Hz), 1.29 (brs, 18H), 1.65 (m, 2H), 1.92 (p, 2H, J=7.4 Hz), 2.33 (m, 2H), 2.53 (t, 2H, J=7.9 Hz), 4.13 (m, 2H), 6.53 (s, 1H) and 7.45 (s, 1H).

MS m/e (% abundance): 381 (M+ +1, 13), 365 (4), 183 (29), 180 (100), 154 (33), 101 (52) and 73 (64).

4-(3-Dodecanoyloxypropy-5-hydroxy-2(5H)-furanone (Compound 50)

A mixture of 3-(5-trimethylsilyl-3-furyl)propyl dodecanoate (105 mg, 0.27 mmol) and Rose Bengal (5 mg) in tetrahydrofuran (6 ml) was exposed to singlet oxygen for 2.5 hours at −78 degrees. The residue, after solvent removal, was purified by preparative thin layer chromatography (TLC) (20×20 cm, 500u silica plate; developed with 60% ethyl ether/petroleum ether). The title ester was obtained as an off-white solid.

$^1$H NMR (CDCl$_3$): 0.89 (t, 3H, J=6.9 Hz), 1.27 (brs, 18H), 1.60 (m, 2H), 1.99 (p, 2H, J=7.4 Hz), 2.32 (t, 2H, J=7.7 Hz), 2.52 (brt, 2H), 4.17 (t, 2H, J=6.3 Hz), 5.91 (s, 1H), and 6.03 (s, 1H).

$^{13}$C NMR (CDCl$_3$): 14.1, 22.7, 24.3, 24.9, 25.8, 29.1, 29.3, 29.5, 29.6, 31.9, 34.3, 63.1, 99.2, 117.8, 168.6, 171.3 and 174.3.

MS m/e: Exact mass calculated for C$_{19}$H$_{36}$NO$_5$ (M+NH$_4$)+: 358.2593, found 358.2583.

Octyl 3-(2-trimethylsilyl-4-furyl)propen-2-oate (Compound 11), and Octyl 3-(5-hydroxy-2-on-4-furyl)propen-2-oate (Compound 51)

Lithium diisopropylamide (a 1.5M solution in cyclohexane; 1.34 ml, 2.0 mmol) was added dropwise to a solution of octyl acetate (322.2 mg, 193 mmol) in tetrahydrofuran (7 ml) at −78 degrees under argon. After 20 minutes, a solution of 5-trimethylsilyl-3-furaldehyde (324 mg, 1.93 mmol) in tetrahydrofuran (1 ml) was added. Stirring was continued at −78 degrees for 1 hour and trifluoromethanesulfonic anhydride (0.65 ml, 3.86 mmol) was added. After 1 hour, 1,8-diazobicyclo[5.4.0]undec-7-ene (0.58 ml, 3.86 mmol) was added and stirring was continued overnight while the cooling bath attained room temperature. The mixture was diluted with ether (30 ml) and acidified with diluted HCl. Extraction (ethyl ether), washing of the extracts (brine), drying (magnesium sulphate) and evaporation afforded an oil, which was subjected to flash chromatography (silica). Elution with 10% ethyl ether/hexane gave octyl 3-(2-trimethylsilyl-4-furyl) propen-2-oate (Compound 11) as a light yellow oil, and oxidation with singlet oxygen gave octyl 3-(5-hydroxy-2-on-4-furyl)propen-2-oate (Compound 51).

Compound 11: $^1$H NMR (CDCl$_3$): 0.29 (s, 9H), 0.91 (t, 3H, J=6.9 Hz), 1.30 (brs, 10H), 1.70 (m, 2H), 4.18 (t, 2H, J=6.8 Hz) 6.17 (d, 1H, J=15.0 Hz), 6.80 (s, 1H), 7.60 (d, 1H, J=15.6 Hz), and 7.84 (s, 1H).

MS m/e (% abundance): 323 (M+ +1, 20), 322 (m+, 47), 307 (15), 210 (36), 195 (61), 166 (70) and 73 (100).

EXAMPLE 11

5Methyl-2-trimethylsilyl-4-furaldehyde

D-Butyl lithium (a 1.6 M solution in hexane; 2.04 ml, 3.28 mmol) was added dropwise to a solution of N,N'N'-trimethylethylenediamine (0.46 ml, 3.56 mmol) in tetrahydrofuran (7 ml) at −78 degrees under argon.

After 15 minutes, a solution of 2-trimethylsilyl-4-furaldehyde (0.5 g, 2.98 mmol) in tetrahydrofuran (2 ml) was added, followed by n-butyl lithium (3.72 ml, 5.94 mmol) after 15 minutes. Iodomethane (1.12 ml, 17.9 mmol) was then added and the mixture was allowed to warm to room temperature gradually over ½ hour. The mixture was quenched with brine and extracted with ethyl ether. Evaporation of the dried (magnesium sulphate) extracts gave an oil, which was purified by flash chromatography using 10% ethyl ether/hexane. Fractions with $R_f$ of about 0.22 on evaporation afforded the title methylfuran as a light yellow oil.

$^1$H NMR (CDCl$_3$) 0.29 (s, 9H), 2.63 (s, 3H), 6.91 (s, 1H) and 9.95 (s, 1H).

LRMS m/e (% abundance) 183 (M+ +1, 35), 167 (28), 149 (20), 83 (40), 73 (100) and 43 (31).

5-Methyl-4-(1-acetoxytridecyl)-2-trimethylsilylfuran

A mixture of 1-bromododecane (261 mg, 0.11 mmol) and magnesium turnings (27 mg, 0.11 mmol) in tetrahydrofuran (7 ml) was refluxed under argon for 1 hour. After cooling to room temperature, a solution of 5-methyl-2-trimethylsilyl-4-furaldehyde (158.6 mg, 0.87 mmol) in tetrahydrofuran (1 ml) was added, followed by acetic anhydride (0.25 ml, 2.6 mmol) after 1 hour. Stirring was continued at room temperature overnight and the mixture was quenched with water. Extraction (ethyl ether) and evaporation of the dried (magnesium sulphate) extracts gave an oil, which was purified by preparative TLC (20x20 cm, 1000 micron silica plate; developed with 5% ethyl ether/hexane). The title ester was obtained as a light yellow oil.

$^1$H NMR (CDCl$_3$) 0.26 (s, 9H), 0.91 (t, 3H, J=6.9 Hz), 1.27 (s, 20H), 1.60-1.90 (m, 2H), 2.05 (s, 3H), 2.35 (s, 3H), 5.69 (t, 1H, J=7.5 Hz) and 6.55 (s, 1H).

LRMS m/e (% abundance) 394 (M+, 8), 352 (23), 334 (36), 183 (47), 167 (20), 117 (28), 73 (100) and 43 (41).

4-(1-Acetoxytridecyl)-5-hydroxy-5-methyl-2-furanone (Compound 60)

A mixture of 5-methyl-4-(1-acetoxytridecyl)-2-trimethylsilylfuran (237 mg, 0.60 mmol) and Rose Bengal (5 mg) in tetrahydrofuran (10 ml) was exposed to singlet oxygen at −78 degrees C. for 2 hours. The residue, after solvent removal, was purified by preparative TLC (20×20 cm, 1000 micron silica plate; developed with 60% ethyl ether/hexane). The title furanone was obtained as a light yellow oil. This compound is a mixture of epimers which isomerizes upon standing.

$^1$H NMR (CDCl$_3$) 0.92 (t, 3H, J=6.9 Hz), 1.30 (brs, 20H), 1.70 (brs, 3H), 1.80 (m, 2H), 2.15 (2s, 3H), 5.25 (brm, 1H), 5.45 (t, 0.7H, J=7.5 Hz), 5.96 (s,0.7H), 6.03 (s, 0.3H) and 6.11 (brm, 0.3H).

$^{13}$C NMR (CDCl$_3$) 13.7, 20.5, 22.3, 23.3, 24.1, 24.9, 28.8, 29.0, 29.1, 29.2, 29.3, 31.6, 33.2, 33.3, 69.0, 69.3, 106.5, 117.0, 118.1, 169.6, 169.7, 169.8, 170.0, 170.1, 170.7, 171.9 and 172.0.

HRMS exact mass calculated for C$_{20}$H$_{38}$NO$_5$ (M+NH$_4$)+ 372.2749, found 372.2754.

3-(O-tert-Butyldimethylsilylmethoxy)furan

3-Furylmethanol (15.5 ml, 0.18 mol), followed by 1,8-diazabicyclo[5.4.0]undec-7-ene (29.7 ml, 0.19 mol) was added to a solution of tert-butyldimethylsilyl chloride (29.9 g, 0.19 m) in dichloromethane (140 ml) at 0 degrees C. under argon. After stirring at room temperature overnight, the reaction was quenched with 5% ice cold hydrochloric acid. Extraction with dichloromethane and evaporation of the dried (magnesium sulfate) extracts gave an oil which was purified by flash chromatography on silica using hexane to give the desired silyl ether. (See Reference: Patrick G. Spinazze and Brian A. Keay, "THE 1,4 C-O SILYL MIGRATIONS OF VARIOUS FURAN AND THIOPHENE SYSTEMS", Tetrahedron Letters, Vol. 30, No. 14, pp 1765-1768, 1989).

$^1$H NMR (CDCl$_3$): 0.05 (s, 6H), 0.89 (s, 9H), 4.58 (s, 2H), 6.35 (1H) and 7.33 (m, 2H).

3-(2-tert-Butyldimethylsilyl)furylmethanol n-BuLi (a 1.5M solution in hexane; 38.9 ml, 58 mmol) was added to a solution of 3-(O-tert-butyldimethylsilylmethoxy)furan (11.2 g, 52.7 mmol) and hexamethylphosphoramide (10.1 ml, 58 mmol) in tetrahydrofuran (200 ml) at −78 degrees C. under argon. After 1 hour stirring at −20 degrees C., the reaction was quenched with an aqueous solution of saturated ammonium chloride. Extraction (ethyl acetate) and evaporation of the dried (magnesium sulfate) extracts gave an oil, which was purified by flash chromatography on silica using 20% ethylacetate/hexane to give the desired furylmethanol.

$^1$H NMR (CDCl$_3$): 0.29 (s, 6H), 0.90 (s, 9H), 1.45 (brt, 1H), 4.59 (d, 2H, J=3.4 Hz), 6.49 (d, 1H, J—1.7 Hz) and 7.60 (d, 1H, J=1.7 Hz)

2-(tert-Butyldimethylsilyl)-3-hydroxymethyl-4-furaldehyde n-BuLi (a 1.6M solution in hexane; 2.7 ml, 4.28 mmol) was added dropwise to a solution of 3-(2-tert-butyldimethylsilyl)-furylmethanol (430 mg, 2.0 mmol) in dimethoxyethane (5 ml) at −78 degrees C. under argon. After stirring at 0 degrees c. for 15 minutes, lithium chloride (860 mg, 20.4 mmol), followed by N,N-dimethylformamide (0.35 ml, 4.48 mmol) was added. Stirring continued at 0 degrees C. for 16 hours and the mixture was quenched with ammonium chloride. Extraction with ethyl acetate and evaporation of the dried (magnesium sulfate) extracts gave a solid, which was recrystallized from hexane to give the titled aldehyde.

IR (CHCl$_3$) 3470, 1680, 1660, 1570 and 1510.

$^1$H NMR (CDCl$_3$) 0.28 (s, 6H), 0.87 (s, 9H), 4.08 (t, 1H, J= 7.3 Hz), 4.58 (d, 2H, J=7.3 Hz), 8.27 (s, 1H) and 9.90 (s, 1H).

$^{13}$CNMR (CDCl$_3$) 5.9, 17.1, 26.1, 55.4, 128.3, 133.9, 158.2, 158.3 and 186.6.

LRMS m/e (% abundance0 258 [(M+NH$_4$)+,1], 240 (56), 223 (53), 184 (26), 183 (10) and 167 (41).

4-[2-(tert-Butyldimethylsilyl)-2-methyl]furylmethanol a) 3-(2-tert-Butyldimethylsilyl-4-carbonyl)furylmethyl methanesulfonate A solution of 2-(tert-butyldimethylsilyl)-3-hydroxymethyl-4-furaldehyde (4.98 g, 20.7 mmol), diisopropylethylamine (7.95 ml, 45.6 mmol) in tetrahydrofuran (70 ml) was added dropwise to a solution of methanesulfonyl chloride (6.42 ml, 82.9 mmol) in tetrahydrofuran (70 ml) at −20 degrees C. under argon. After stirring at −20 degrees C. for 90 minutes, the mixture was diluted with ethyl ether and washed successively with 10% hydrochloric acid, water and brine. Evaporation of the dried (magnesium sulfate) organic phase gave an oil, which was purified by flash chromatography on silica using 20% ethylacetate/hexane to give the titled mesylate.

¹HNMR (CDCl₃) 0.36 (s, 6H), 0.93 (s, 9H), 3.16 (s, 3H), 5.33 (s, 2H), 7.27 (s, 1H), 8.26 (s, 1H) and 10.02 (s, 1H).

b) 4-2-(tert-Butyldimethylsilyl)-3-methyl]furylmethanol

Lithium aluminum hydride (a 1.0M solution in THF; 62.2 ml, 62.2 mmol) was added dropwise to a solution of the mesylate from above in THF (10 ml) at −20 degrees C. under argon. After 20 minutes, TLC showed that the reaction has been completed. The mixture was quenched carefully with dilutehydrochloric acid. Extraction with ethyl ether and evaporation of the dried (magnesium sulfate) extracts gave an oil, which was purified by flash chromatography on silica using 20% ethyl acetate/hexane to give the titled alcohol.

IR (CHCl₃) 3450 and 1600

¹H NMR (CDCl₃) 0.27 (s, 6H), 0.91 (s, 9H), 2.12 (s, 3H), 4.53 (s, 2H) and 7.56 (s, 1H).

¹³CNMR (CDCl₃) −6.1, 9.0, 17.5, 26.2, 55.4, 125.5, 130.8, 144.6 and 155.1

LRMS m/e (% abundance) 226 (M+, 32), 209 (45), 170 (18), 169 (91), 142 (13), 141 (100), 101 (10) 97 (41), 75 (93) and 73 (22).

2-(tert-Butyldimethylsilyl)-3-methyl-4-furaldehyde

A solution of 4-[2-(tert-butyldimethylsilyl)-3-methyl]-furyl-methanol (380 mg, 1.68 mmol) in dichloromethane (5 ml) was added to a suspension of barium permanganate (6.45 g, 25.2 mmol) in dichloromethane (40 ml) at 0 degrees C. under argon. After stirring at room temperature for 15 hours, the mixture was filtered through celite. After concentration by evaporation the filtrate was purified by flash chromatography on silica using 5% ethyl ether/hexane to give the titled aldehyde.

IR (CHCl₃) 2820, 2740 and 1680

¹HNMR (CDCl₃) 0.2 (s, 6H), 0.82 (s, 9H) 2.23 (s, 3H), 8.09 (s, 1H) and 9.91 (s, 1H).

¹³CNMR (CDCl₃) −6.3, 9.8, 17.3, 25.9, 128.1, 129.9, 156.8, 157.6 and 185.7.

LRMS m/e (% abundance) 224 (11), 168 (16), 167 (100), 83 (12) and 73 (11).

4-(1-Acetoxytridecyl)-2-(tert-butyldimethylsilyl)-3-methylfuran 2-(tert-Butyldimethylsilyl)-3-methyl-4-furaldehyde (95 mg, 0.42 mmol) was added to a solution of dodecylmagnesium bromide (a 1.0M solution in THF; 0.51 ml, 0.51 mmol) in THF (1 ml) at 0 degrees C. under argon. When all the aldehyde has reacted, acetic anhydride (80 microliter, 0.85 mmol) was added. After stirring at room temperature for 16 hours, the mixture was quenched with dilute hydrochloric acid. Extraction with diethyl ether and evaporation of the dried (magnesium sulfate) extracts gave an oil, which was purified by flash chromatography on silica using 5% ethyl ether/hexane to give the titled acetate.

IR (CHCl₃) 1730 and 1710.

¹HNMR (CDCl₃) 0.26 (s, 6H), 0.88 (t, 3H, J=6.9 Hz), 1.25 (brs, 20H), 1.80 (m, 2H), 2.03 (s, 3H), 2.07 (s, 3H), 5.78 (t, 1H, J=7.0 Hz) and 7.52 (s, 1H)

¹³CNMR (CDCl₃) −6.1, 9.5, 13.8, 17.5, 21.0, 22.5, 25.4, 26.2, 29.1, 29.2, 29.3, 29.4, 31.7, 34.6, 68.4, 125.4, 130.2, 144.4, 154.7 and 170.7

LRMS m/e (% abundance) 436(M+, 4), 320 (3), 211 (14), 118 (10), 117 (100), 75 (22) and 73 (18).

4-(1-Acetoxytridecyl)-3-methyl-5-hydroxy-2(5H)-furanone (Compound 61)

A mixture of 4-(1-acetoxytridecyl)-2-(tertbutyldimethylsing 3-methylfuran (132 mg, 0.3 mmol), water (a few drops) and Rose Bengal (5 mg) in acetone (30 ml) was exposed to singlet oxygen at 0 degrees C. for 6 hours. The residue, on evaporation, was purified by flash chromatography on silica using 20% ethylacetate/hexane to give the titled furanone as a mixture of stereoisomers.

¹H NMR (CDCl₃) 0.82 (t, 3H, J=6.9 Hz), 1.20 (brs, 20H), 1.75 (m, 2H), 1.85 (s, 3H), 2.03 (s, 3H), 2.06 (s, 3H), 5.35 9m, 2H), 5.88 (brs, 1H) and 6.08 (brs, 1H).

¹³C NMR (CDCl₃) 9.2, 14.2, 20.8, 22.8, 25.6, 29.4, 29.5, 29.6, 29.7, 29.8, 32.1, 32.8, 70.1, 70.7, 97.7, 128.5, 128.9, 156.5, 156.6, 171.7, 172.1, 172.7 and 173.1.

LRMS m/e (% abundance) 355 (M+, 16), 296 (11), 295 (59), 294 (100), 277 (19), 267 (45), 126 (34), 125 (41), 112 (18), 95 (23), 81 (22) and 69 (27).

2-(tert-butyldimethylsilyl)-3-methyl-4-(1-phenylcarbamoyloxy)tridecylfuran and 2-tert-butyldimethylsilyl)-3-methyl-4-[1-N-phenyl-N-phenylcarbamoyl)carbamoyloxy]tridecylfuran Dodecylmagnesium bromide (a 1.0M solution in THF; 0.89 ml, 0.89 mmol) was added to a solution of 2-tert-butyldimethylsilyl-3-methyl-4-furaldehyde (200 mg, 0.89 mmol) in THF (5 ml) at 0 degrees C. under argon. After stirring at room temperature for 1 hour, the mixture was recooled to 0 degrees C. and phenylisocyanate (97 microliter, 0.89 mmol) was added. Stirring was continued for 5 minutes and the reaction mixture was quenched with ammonium chloride. Extraction with diethyl ether and evaporation of the dried (magnesium sulfate) extracts gave an oil. The crude product was purified by flash chromatography (SiO₂; 5% diethylether/hexane) to give the desired mono- and bis-phenylcarbonate.

2-(tert-Butyldimethylsilyl)-3-methyl-4-(1-phenylcarbamoyloxy)tridecylfuran: R_f(5% diethyl ether/hexane) 0.34; IR (CHCl₃) 3430, 1725, 1680, 1595 and 1515;

¹HNMR (CDCl₃) 0.24 (s, 6H), 0.88 (t+s, 12H), 1.23 (m, 20H), 1.90 (m, 2H), 2.09 (s, 3H), 5.77 (t, 1H, J=7.0 Hz), 6.65 (s, 1H), 7.02 (t, 1H, J=7.3 Hz), 7.25 (m, 2H), 7.35 (m, 2H) and 7.54 (s, 1H);

¹³CNMR (CDCl₃) −6.1, 9.6, 13.8, 17.5, 22.4, 25.4, 26.2, 29.1, 29.2, 29.3, 29.4, 31.7, 34.8, 69.5, 118.7, 123.5, 125.4, 129.2, 130.2, 138.2, 144.4, 153.4 and 154.9.

2-(tert-Butyldimethylsilyl)-3-methyl 4-[1-(N-phenyl-Nphenylcarbamoyl)carbamoyloxy]tridecylfuran: R_f (5% diethyl ether/hexane) 0.23;

¹H NMR (CDCl₃) 0.24 (s, 6H), 0.87 (s+t, 12H), 1.24 (m, 20H), 1.56 (m, 2H), 1.79 (s, 3H), 5.75 (t, 1H, J=6, 2Hz), 7.07 (t, 1H, J—8.0 Hz), 7.20 (m, 2H), 7.30 (m, 3H), 7.42 (m, 3H), 7.54 (m, 2H) and 10.9 (s, 1H);

¹³CNMR (CDCl₃) −6.2, −6.1, 9.3, 13.6, 17.5, 22.4, 24.9, 26.1, 28.8, 29.1, 29.2, 29.3, 29.4, 31.7, 34.4, 72.8, 120.0, 124.0, 124.1, 128.4, 128.9, 129.0, 129.5, 137.4, 138.0, 144.3, 151.8, 155.3 and 155.6.

5-Hydroxy-3-methyl-4-(1-phenylcarbamoyloxy)-tridecyl)-2-(5H)furanone

A mixture of 2-(tert-butyldimethylsilyl)-3-methyl-4-(1-phenylcarbamoyloxy)tridecylfuran (226 mg, 0.44 mmol), water a few drops) and polymer bound Rose Bengal (0.077 g) in acetone (80 ml) was exposed to singlet oxygen at 0 degrees C. for 5 hours. The residue, on evaporation, was purified by flash chromatography (SiO$_2$, 20% ethylacetate/hexane) to give the titled furanone as a mixture of stereoisomers.

IR (CHCl$_3$) 3400–3200, 1768, 1725, 1605 and 1520;

$^1$HNMR (CDCl$_3$) 0.88 (t, 3H, J=6.9 Hz), 1.26 (m, 20H), 1.80 (m, 1H), 1.91 (s, 3H), 1.95 (m, 1H), 5.48 (brt, 1H), 5.52 (m, 1H), 5.95 (br, 1H), 6.04 (brs, 1H), 6.19 (brs, 1H), 7.00–7.40 (m, 6H);

$^{13}$C NMR (CDCl$_3$) 8.7, 13.8, 22.4, 25.2, 28.9, 29.1, 29.2, 29.3, 29.4, 29.5, 31.7, 32.4, 32.5, 69.9, 70.6, 97.2, 97.4, 118.8, 119.0, 119.4, 123.9, 124.1, 128.1, 128.9, 129.2, 137.3, 137.6, 153.2, 153.4, 153.6, 156.0, 156.8, 172.5 and 172.7.

5-Methyl-2-triethylsilyl-4-furaldehyde n-Butyl lithium (a 1.6M solution in THF; 19.0 ml, 30.4 mmol) was added to a solution of morpholine (2.67 ml, 30.4 mmol) in THF (20 ml) at −78 degrees C. under argon. After 20 minutes, 3-furaldehyde (1.8 ml, 28.9 mmol) was added, followed by s-butyl-lithium (a 1.3M solution in cyclohexane; 23.4 ml, 30.4 mmol) after another 20 minutes. Stirring was continued for 2 hours and chlorotriethylsilane (5.1 ml, 30.4 mmol) was added. After 2 hours at −78 degrees C., s BuLi (23.4 ml, 30.4 mmol) wad added, followed by iodomethane (5.4 ml, 86.9 mmol) after another 2 hours. The mixture was stirred at room temperature for 15 hours and quenched with ice cold dilute hydrochloric acid. Extraction with ethyl ether and evaporation of the dried (magnesium sulfate) extracts gave an oil, which was purified by flash chromatography on silica using 10% diethyl ether/hexane to give the titled aldehyde.

IR (CHCl$_3$) 1690

$^1$HNMR (CDCl$_3$) 0.75 (q, 6H, J=8.0 Hz), 0.98 (t, 9H, J=8.0 Hz), 2.60 (s, 3H), 6.90 (s, 1H) and 9.90 (s, 1H).

$^{13}$CNMR (CDCl$_3$) 2.6, 6.7, 12.5, 118.8, 122.8, 158.5, 166.2 and 185.1; HRMS exact mass calculated for C$_{12}$H$_{20}$O$_2$Si 224.1232 found 224.1226

4-(1-Acetoxytridecyl)-5-methyl-2-triethylsilylfuran

5-Methyl-2-triethylsilyl-4-furaldehyde (145 mg, 0.65 mmol) was added to a solution of dodecylmagnesium bromide (a 1.0M solution in THF; 0.76 ml, 0.74 mmol) in THF at 0 degrees C. under argon. When all the aldehyde has consumed, acetic anhydride (0.1 6 ml, 1.71 mmol) was added. Stirring was continued at room temperature for 15 hours and the mixture was quenched with water. Extraction with diethyl ether and evaporation of the dried (magnesium sulfate) extracts gave an oil, which was purified by flash chromatography on silica using 5% diethylether/hexane to give the titled acetate.

IR (CHCl$_3$) 1730

$^1$HNMR (CDCl$_3$) 0.75 (q, 6H, J=8.0 Hz), 0.88 (t, 3H, J=7.0 Hz), 0.95 (t, 9H, J=8.0 Hz), 1.25 (brs, 20H), 1.75 (m, 1H), 1.95 (m, 1H), 2.01 (s, 3H), 2.31 (s, 3H), 5.69 (t, 1H, J=7.2 Hz) and 6.55 (s, 1H).

$^{13}$CNMR (CDCl$_3$) −2.9, 7.0, 11.9, 13.8, 21.0, 22.5, 25.3, 25.7, 29.0, 29.2, 29.3, 29.4, 31.7, 34.8, 68.8, 118.8, 120.3, 154.1, 156.1 and 170.7. LRMS m/e (% abundance) 436 (M+, 9), 377 (22), 376 (33), 347 (43), 239 (29), 145 (100), 115 (34), 103 (30) AND 87 (30); HRMS Exact Mass calculated for C$_{26}$H$_{48}$O$_3$Si (M+) 436.3373, found 436.3374.

4-(1-Acetoxytridecyl)-5-hydroxy-5-methyl-2-furanone (Compound 60)

A mixture of 4-(1-acetoxytridecyl)-2-methyl-5-triethylsilylfuran (231 mg, 0.53 mmol), water (a few drops) and Rose Bengal (6.3 mg) in acetone (100 ml) was exposed to singlet oxygen at 0 degrees C. for 3 hours. The residue, after evaporation, was purified by flash chromatography on silica using 10% ethylacetate/hexane to give the titled furanone. This compound is a mixture of epimers which isomerizes upon standing.

IR (CHCl$_3$) 3600–3200, 1770 and 1740. For other physical data of this compound see description of the same above.

5-Methyl-2-triethylsilyl-4-(1-phenylcarbamoyloxy)-tridecylfuran

A solution of 5-methyl-2-triethylsilyl-4-furaldehyde (219 mg, 0.98 mmol) in THF (5 ml) was added to a solution of dodecylmagnesium bromide (a 1.0M solution in THF; 1.08 ml; 1.08 mmol) in THF at 0 degrees C. under argon. When all the aldehyde was consumed, phenylisocyanate (0.12 ml, 1.08 mmol) was added. After stirring at room temperature for 16 hours, the mixture was quenched with dilute hydrochloric acid. Extraction with diethylether and evaporation of the dried (magnesium sulfate) extracts gave an oil, which was purified by flash chromatography on silica using 5% ethyl ether/hexane to give the titled furan.

IR (CHCl$_3$) 3440, 1730 and 1520.

$^1$HNMR (CDCl$_3$) 0.72 (q, 6H, J=6.6 Hz), 0.88 (t, 3H, J=6.6 Hz), 0.98 (t, 9H, J=6.6 (Hz), 1.25 (brs, 20H), 1.75 (m, 1H), 1.95 (m, 1H), 2.36 (s, 3H), 5.70 (t, 1H, J—7.3 Hz), 6.57 (s, 1H), 6.62 (br, 1H), 7.02 (m, 1H), 7.29 (m, 2H) and 7.37 (m, 2H).

$^{13}$CNMR (CDCl$_3$) 2.9, 7.1 11.9, 13.8, 22.5, 25.3, 29.1, 29.2, 29.3, 29.4, 31.7, 35.0, 69.9, 118.7, 118.8, 120.2, 123.3, 129.1, 138.3, 144.8, 153.5, 154.3 and 156.3.

5-Methyl-5-hydroxy-4-(1-phenylcarbamoyloxy)tridecyl-2-furanone (Compound 62)

A mixture of 5-methyl-2-triethylsilyl-4-(1-phenylcarbamoyloxy) tridecylfuran (80 mg, 0.13 mmol) water ( a few drops) and Rose Bengal (ca, 3 mg) in acetone (60 ml) was to singlet oxygen at 0 degrees C. for 4 hours. The residue, after evaporation, was purified by flash chromatography on silica using 20% ethylacetate/hexane to give the titled furanone.

IR (CHCl$_3$) 3440, 3400–3240, 1765, 1730, 1600 and 1525.

$^1$HNMR (CDCl$_3$) 0.88 (t, 3H, J - 6.9 Hz), 1.26 (brs, 20H), 1.67 (brm, 2H), 1.79 (brs, 3H), 5.18 (brm, 1H), 5.50 (brm, 1H), 5.85 (br, 1H), 6.03 (br, 1H), 7.12 (m, 2H) and 7.40 (m, 3H).

$^{13}$CNMR (CDCl$_3$) 13.8, 22.4, 22.8, 24.2, 24.3, 24.8, 25.1, 28.9, 29.1, 29.2, 29.3, 29.4, 31.7, 3.33, 34.0, 69.6, 70.2, 70.3, 98.2, 106.5, 118.1, 119.2, 124.1, 124.3, 124.5, 129.3, 136.9, 153.9, 169.9 and 170.4.

LRMS m/e (% abundance) 431 (M+, 4), 277 (7), 153 (6), 137 (12), 126 (12), 119 (25), 109 (11), 94 (13), 93 (100) and 55 (30).

5-Butyl-2-triethylsilyl-4-furaldehyde

Using the same procedure as 5-methyl-2-trimethylsilyl-4-furaldehyde but substituting 2-trimethylsilyl-4-furaldehyde and methyl iodide with 2-triethylsilyl-4-furaldehyde and 1-iodobutane respectively gives 5-butyl-2-triethylsilyl-4-furaldehyde. IR (neat) 1690 cm$^{-1}$; $^1$HNMR (CDCl$_3$) 0.73 (q, 6H, J=8.4 Hz), 0.95 (m, 12H), 1.36 (p, 2H, J=7.5 Hz), 1.69 (p, 2H, J=7.5 Hz), 2.94 (t, 2H, J=7.5 Hz), 6.89 (s, 1H) and 9.91 (s, 1H) $^{13}$CNMR (CDCl$_3$): 3.03, 7.17, 13.6, 22.2, 26.8, 30.4, 118.6, 122.5 158.4, 170.2 and 184.8. LRMS m/e (% abundance) 266 (M+, 20) 238 (20) 237 (100), 87 (10) and 75 (20); HRMS exact mass calculated for C$_{15}$H$_{26}$O$_2$Si 266.1702, found 266.1690.

5-Butyl-5-hydroxy-4-(1-phenylcarbamoyloxy)tridecyl-2-furanone a)
5-Butyl-4-(1-phenylcarbamoyloxy)tridecyl-2-triethylsilylfuran Dodecyl magnesium bromide (a 1.0M solution in THF; 0.25 ml, 0.25 mmol) was added to a solution of 5-butyl-2-triethylsilyl-4-furaldehyde (59 mg, 0.22 mmol) in THF (1 ml) at 0 degrees C. under argon. When all the aldehyde has reacted, phenylisocyanate (27 microliter, 0.25 mmol) was added and stirring was continued at −40 degrees C. for 14 hours. Without purification the crude product was used in the next step.
$^1$HNMR (CDCl$_3$)

b)
5-Butyl-5-hydroxy-4-(1-phenylcarbamoyloxy)tridecyl-2-furanone

Water (a few drops) and Rose Bengal (ca. 3 mg) were added to the above reaction mixture. The mixture was exposed to singlet oxygen for 3 hours at 0 degrees C. The residue, after evaporation, was purified by preparative TLC (SiO$_2$) developed with 40% diethyether/hexane to give the titled furanone.
IR (CHCl$_3$) 3600–3240, 3440, 1770, 1760, 1730, 1605, 1550, and 1530.
$^1$HNMR (CDCl$_3$) 0.88 (m, 6H), 1.30 (brm, 22H), 1.50 (m, 2H), 1.75 (m, 2H), 2.00 (m, 2H), 5.10 (brm, 1H), 5.70 (br, 1H), 6.04 (brs, 1H), 6.95 (brs, 1H), 7.15 (brm, 1H), 7.30 (m, 3H) and 7.50 (m, 2H)
$^{13}$C NMR (CDCl$_3$) 13.6, 13.8, 22.1, 2.22, 22.4, 24.3, 24.6, 25.1, 28.6, 28.9, 29.0, 29.1, 29.3, 29.4, 36.3, 69.7, 108.3, 118.9, 119.2, 119.4, 120.2, 124.5, 128.6, 129.0, 129.2, 129.3, 129.4, 136.8, 169.2, 169.7 and 169.9. LRMS m/e (% abundance) 491[M+NH$_4$)+, 67], 474[(M+H)+, 86], 473 (M+, 23), 456 (33), 372 (30), 354 (30), 337 (66), 319 (38), 272 (48), 213 (80), 120 (27) 119 (45), 94 (58) and 93 (100).

2-tert-Butyldimethylsilyl-3,5-dimethyl-4-furaldehyde

Treatment of 2-tert-butyldimethylsilyl-4-hydroxymethyl-3-methylfuran with n-butyl lithium and iodomethane gives 2-tert-butyldimethylsilyl-3,5-dimethyl-4-hydroxymethylfuran. Oxidizing of this furan with barium permanganate gives the titled furaldehyde.

2-Triethylsilyl-5-phenyl-4-furaldehyde

Treatment of 2-triethylsilyl-4-furaldehyde with lithio N,N,N'-trimethylethylenediamine, followed by phenyl trifluoromethanesulfonate in the presence of anhydrous zinz chloride and tetrakis (triphenylphosphine) palladium (o) and work up gives the titled aldehyde.

2-Phenyl-2-triethylsilyl-4-furaldehyde n-Butyllithium (a 1.42M solution in hexane, 2.33 ml, 3.31 mmol) was added to a solution of 1-methylpiperazine (331 mg. 3.31 mmol) in tetrahydrofuran (15 ml) at 0 degrees under argon. After 15 minutes the solution was cooled to −78 degrees and 4-phenyl-3-furaldehyde. (517 mg, 3.01 mmol) was added. This mixture was warmed to 0 degrees and stirred for 15 minutes, then recooled to −78 degrees before sec-butyllithium (a 1.3M solution in cyclohexane, 2.77 ml, 3.61 mmol) was added dropwise This solution was stirred 12 hours at −78 degrees C. before chlorotriethylsilane (1.81 g, 12.02 mmol) was added. The mixture was allowed to warm gradually to room temperature and stirred an additional 1½ hours. The reaction was quenched with ice-cold 5% (V/V) hydrochloric acid and the organics were extracted into ethyl ether. The combined fractions were washed with saturated sodium bicarbonate, H$_2$O and brine. Evaporation of the dried (magnesium sulfate) extracts gave an oil which was purified by flash chromatography on silica using 10% ethyl acetate/hexanes to give the title aldehyde.
IR (heat): 2952, 1691 cm:
$^1$H NMR (CDCl$_3$): 0.62 (q, J=7.8 Hz, 6H); 0.85 (t, J=7.8 Hz, 9H); 7.20 to 7.43 (m, 5H); 8.30 (s, 1H); 9.79 (s, 1H).
$^{13}$C NMR (CDCl$_3$) 3.0, 6.8, 127.1, 128.2, 130.2, 131.8, 136.5, 153.7, 158.3, 186.1.

3-Phenyl-2-triethylsilyl-4-furanmethanol

LiAlH$_4$ (1.0M solution in hexane, 1.48 ml, 1.48 mmol) was added dropwise to a solution of 3-phenyl-2-triethylsilyl-4-furaldehyde (422 mg, 1.48 mmol) in tetrahydrofuran (10 ml) at 0 degrees under argon. This mixture was warmed to room temperature, quenched with ice-cold 5% (V/V) hydrochloric acid and the organics were extracted into ethyl ether. The combined fractions were washed with saturated sodium bicarbonate, H$_2$O and brine. The dried extracts (magnesium sulfate) were concentrated to an oil which was purified by flash chromatography on silica using 20% ethyl acetate/hexanes to give the title compound.
IR (neat): 3300 (broad); 2953 cm$^{-1}$.
$^1$H NMR (CDCl$_3$): 0.59 (q, J=8.0 Hz, 6H); 0.85 (t, J=8.0 Hz, 9H); 1.60(brs, 1H); 4.42 (brs, 2H); 7.29 to 7.40 (m, 5H); 7.68 (s, 1H).
$^{13}$C NMR (CDCl$_3$) 3.2, 6.9, 55.2, 125.2, 127.6, 128.2, 130.0, 133.7, 137.5, 144.9, 155.7.

4-Dodecoyloxymethyl-3-phenyl-2-triethylsilylfuran

To a stirred solution of 3-phenyl-2-triethylsilyl-4-furanmethanol (345. mg, 1.20 mmol) and triethylamine (182 mg, 1.80 mmol) in tetrahydrofuran (15 ml) at 0 degrees under argon was added lauroyl chloride (786 mg, 3.60 mmol). This solution was allowed to warm gradually to room temperature. After stirring an additional 2 hours the white precipitate was filtered off. The filtrate was taken up into ethyl ether, washed with saturated ammonium chloride, saturated sodium bicarbonate, H$_2$O and brine. Evaporation of the dried (magnesium sulfate) extracts gave an oil which was purified by flash chromatography on silica using 2% ethyl ether/hexanes to give the title compound.
IR (neat): 1737 cm$^{-1}$.
$^1$H NMR (CDCl$_3$) 0.60 (q, J=8.1 Hz, 6H); 0.81 to 0.93 (m, 12H), 1.19 to 1.35 (m, 16H); 1.48 to 1.61 (m, 2H); (m, 2H); 2.23 (t, J=7.5 Hz, 2H); 4.86 (s, 2H); 7.25 to 7.40 (m, 5H); 7.72 (S, 1H).
$^{13}$C NMR (CDCl$_3$) 3.17, 6.90, 13.8, 22.5, 24.7, 28.9, 29.0, 29.1, 29.2, 29.4, 31.7, 34.1, 56.4, 120.5, 127.6, 128.1, 130.1, 133.3, 138.0, 146.4, 155.6, 173.8.

4-Dodecoyloxymethyl-5-hydroxy-3-phenyl-2(5H)-furanone

A mixture of 4-dodecoyloxymethyl-3-phenyl-2-triethylsiylfuran (256 mg, 0.54 mmol), water (a few drops) and Rose Bengal on polymer beads (1.0 g) in tetrahydrofuran was exposed to singlet oxygen at 0 degrees for 3 hours. The Rose Bengal was filtered off and the residue was concentrated to a pink oil which was purified by flash chromatography on silica using 20% ethyl acetate/hexanes to give the title compound.

IR (CHCl$_3$) 3400 (v. broad), 1743 cm$^{-1}$.

$^1$H NMR (CDCl$_3$): 0.88 (t, J=6.6 Hz, 3H); 1.05 to 1.45 (m, 16H); 1.50 to 1.63 (m, 2H); 2.25 (t, J=7.6 Hz, 2H); 5.04 (S, 1H); 5.07 (S, 1H); 5.37 to 5.50 (brs, 1H); 6.22 (S, 1H); 7.40 to 7.54 (m, 5H).

$^{13}$C NMR (CDCl$_3$): 14.1, 22.6, 24.6, 29.0, 29.2, 29.3, 29.4, 29.5, 31.8, 33.8, 57.5, 96.5, 96.6, 128.1, 128.6, 129.1, 129.6, 131.7, 152.6, 170.5, 173.6.

EXAMPLE 12

Ethyl-4-phenyl-3-furoate (Adapted from: Litta, D.; Saindane, M.; Ott, W. *Tet. Lett.* (1983) 24, 2473.)

A mixture of 4-phenyloxazole (500 mg, 3.45 mmol) and ethyl phenyl propiolate (630 mg, 3.62 mmol) were heated in a sealed tube for 16 hours at 210 degrees with stirring. The residue was filtered through silica using 5% ethyl ether/hexanes to give the titled oxazole, 664 mg of a pale oil, which was used without further purification. The starting 4-phenyloxazole was prepared according to Bredereck, H.; Gompper, R. *Chem. Ber.* (1945), 87, 700.

3-phenyl-4-furyl methanol (Compound 19)

LiAlH$_4$ (1.0M solution in hexane 1.14 ml, 1.14 mmol) was added dropwise to a solution of ethyl-4-phenyl-3-furoate, (246 mg, assumed 1.28 mmol) in tetrahydrofuran (20 ml) at 0 degrees under argon. The solution was stirred and was allowed to warm to room temperature gradually over ½ hour. The mixture was quenched with saturated ammonium chloride and the organics were extracted into ethyl ether, and washed with H$_2$O. Evaporation of the dried (magnesium sulfate) extracts gave an oil, which was purified by flash chromatography on silica using 20% ethyl acetate/hexanes. This was further purified by recrystallation (hexane/ethyl ether) to give the title compound as pale yellow crystals.

IR (CHCl$_3$) 3600 v. br., 3000 cm$^{-1}$.

$^1$H NMR (CDCl$_3$): 1.90 (brs, 1H), 4.60 (brs, 2H), 7.22 to 7.60 (m, 7H).

$^{13}$C NMR (CDCl$_3$): 55.4, 124.1, 126.4, 127.4, 127.9, 128.9, 132.2, 140.4, 142.3.

HRMS: exact mass calculated for C$_{11}$H$_{10}$O$_2$(M+) 174.0680, found 174.0696.

3-phenyl-4-furaldehyde (Compound 18)

A mixture of 3-phenyl-4-furylmethanol (Compound 19, 458 mg, 2.63 mmol), powdered 4A molecular sieves (500 mg), 4-methyl-morpholine-N-oxide (462 mg, 3.95 mmol) and tetrapropylammonium perruthenate (46 mg, 0.13 mmol) in anhydrous dichloromethane (40 ml) were stirred at room temperature for 3 hours. Residue was filtered through silica and concentrated to a brown oil which was purified by flash chromatography on silica using 10% ethyl ether/hexanes to give the titled aldehyde IR (CHCl$_3$): 3020, 1690 cm$^{-1}$.

$^1$H NMR (CDCl$_3$): 7.30 to 7.55 (m, 5H); 7.59 (d, J—1.6 Hz, 1H); 8.15 d, J=1.6 Hz, 1H); 9.94 (s, 1H).

$^{13}$C NMR (CDCl$_3$): 125.8, 126.1, 128.0, 128.6, 128.7, 130.0, 142.0, 152.6, 185.2.

HRMS exact mass calculated for C$_{11}$H$_8$O$_2$(M+) 172.0524 observed 172.0520.

3(-1-acetoxytridecyl)-4-phenylfuran

Dodecylmagnesium bromide (a 1.0M solution in THF; 2.11 ml, 2.11 mmol) was added to a solution of 4-phenyl-3-furaldehyde (303 mg, 1.76 mmol) in THF at 0 degrees under argon and gradually allowed to warm to room temperature with stirring. When all of the aldehyde was consumed acetic anhydride (719 mg, 7.04 mmol) was added and stirring was continued for 2 hours more. The reaction was quenched with saturated ammonium chloride and the organics were extracted into ethyl ether. The combined fractions were washed with saturated sodium bicarbonate, water and brine, dried over magnesium sulfate and concentrated to a yellow oil which was purified by flash chromatography on silica using 3% ethyl ether hexanes to give the title compound.

IR (CHCl$_3$): 3020, 1725 cm$^{-1}$.

$^1$H NMR (CDCl$_3$): 0.88 (t, J=6.6 Hz, 3H); 1.10 to 1.40 (m, 20H); 1.53 to 1.78 (m, 2H); 2.00 (s, 3H); 5.92 (t, J=6.8 Hz, 1H); 7.27 to 7.46 (m, 7H).

$^{13}$C NMR (CDCl$_3$): 13.8, 20.9, 22.4, 25.1, 28.9, 29.1, 29.26, 29.36, 29.41, 31.7, 34.4, 68.5, 124.6, 126.3, 127.4, 128.6, 128.8, 132.4, 140.6, 141.5, 170.5.

HRMS: exact mass calculated for C$_{25}$H$_{36}$O$_3$ (M+) 384.2667, observed 384.2672.

4-(-1-acetoxytridecyl)-5-hydroxy-3-phenyl-2(5H)-furanone

3-(-1-acetoxytridecyl)-5-hydroxy-4-phenyl-2(5H)-furanone

A mixture of 3-(-1-acetoxytridecyl)-4-phenylfuran (506 mg, 1.32 mmol), water (a few drops) and Rose Bengal on polymer beads (1.6 g) in THF was exposed to singlet oxygen at 0 degrees C. for 3 hours. The Rose Bengal was filtered off and the residue was concentrated to a pink oil which was purified by flash chromatography on silica using 5 to 20% ethyl acetate/hexanes to give the title furanones as a mixture of isomers. The isomers were separated by HPLC chromatography on reverse phase Vydac column using 15% water/acetonitrile.

3-(-1-acetoxytridecyl)-5-hydroxy-4-phenyl-2(5H)-furanone (retention time: 26.3 minutes).

IR (CDCl$_3$): 3020, 1760 cm$^{-1}$.

$^1$H NMR (CDCl$_3$): 0.88 (t, J=6.7 Hz, 3H); 1.15 to 1.45 (m, 20H); 1.83 (s, 3H); 1.77 to 1.92 (m, 1H); 1.92 to 2.07 (m, 1H); 5.59 (d, J=5.4 Hz 0.5 H); 5.62 (d, J=5.4 Hz, 0.5 H); 6.31 (s, 1H); 7.40 to 7.54 m(5H).

$^{13}$C NMR (CDCl$_3$): 13.9, 20.3, 22.5, 25.4, 28.9, 29.16, 29.23, 29.34 29.41, 29.45, 31.7, 32.6, 68.9, 97.6, 128.5, 128.7, 128.9, 130.2, 130.4, 157.9, 169.6, 171.1.

LRMS m/z calculated for C$_{25}$H$_{40}$O$_5$(M+NH$_4$)=434. Observed 434.

4-(-1-acetoxytridecyl)-5-hydroxy-3-phenyl-2(5H)-furanone (retention time 28.0 minutes).

IR (CHCl$_3$): 3010, 1765 (v. br.)cm$^{-1}$.

$^1$H NMR (CDCl$_3$): 0.88 (t, J=6.5 Hz, 3H); 1.12 to 1.40 (m, 20H); 1.81 (s, 3H); 170 to 185 (m, 1H); 1.85 to 2.00 (m, 1H); 5.62 (d, J=5.1 Hz, 0.5 H); 5.65 (d, J=5.0 Hz, 0.5 H); 6.17 (s, 1H); 7.33 to 7.50 (m, 5H).

$^{13}$C NMR (CDCl$_3$): 13.8, 20.1, 22.4, 25.3, 28.8, 29.1, 29.2, 29.3, 29.4, 31.7, 33.0, 70.3, 97.2, 128.6, 128.9, 129.4, 131.1, 156.8, 170.7, 171.3.

LRMS m/z calculated for C$_{25}$H$_{40}$O$_5$ (M+NH$_4$)-434, observed 434.

2-Methyl-4-phenyl-3-furaldehyde (Compound 16)

n-Butyllithium (a 1.6 m solution in hexane, 2.43 ml, 3.89 mmol) was added to a solution of trimethylethylenediamine (397 mg, 3.89 mmol) in tetrahydrofuran (25 ml) at 0 degrees under argon. After 20 minutes the solution was cooled to −78 degrees and 3-phenyl-4-furaldehyde (Compound 18, 608 mg, 3.35 mmol) was added. This mixture was allowed to gradually warm to −20 degrees and stirred for 1½ hours, then recooled to −78 before n-butyllithium (a 1.6M solution in hexane, 2.43 ml, 3.89 mmol) was added dropwise. The stirring mixture was again gradually warmed to −20 degrees and stirred for 2 hours before iodomethane (2.56 g 17.67 mmol) was added. After stirring for 18 hours at −20 degrees the reaction was quenched with ice-cold 10% (v/v) hydrochloric acid and the organics were extracted into ethyl ether. The combined fractions were washed with saturated sodium bicarbonate, H$_2$O and brine. Evaporation of the dried (magnesium sulfate) extracts gave an oil which was purified by flash chromatography on silica using 20% ethyl ether/hexanes to give the title aldehyde.

IR (CHCL$_3$): 3600, 1690 cm$^{-1}$.

$^1$H NMR (CDCl$_3$): 2.65 (s, 3H); 7.30 to 7.50 (m, 6H); 1.02 (s, 1H).

$^{13}$C NMR (CDCl$_3$): 13.4, 119.8, 127.2, 128.0, 128.7, 129.0, 130.6, 138.3, 162.3, 186.7.

HRMS: exact mass calculated for C$_{12}$H$_{10}$O$_2$ (M+) 186.0680, found 186.0689.

2-Methyl-4-phenyl-3-furylmethanol (Compound 17)

LiAlH$_4$ (1.0M solution in hexane, 0.12 ml, 0.12 mmol) was added dropwise to a solution of 2-methyl-4-phenyl-3-furaldehyde (Compound 58, 45 mg, 0.24 mmol) in tetrahydrofuran (3 ml) at 0 degrees under argon. After 10 minutes the reaction was quenched with saturated ammonium chloride and the organics were extracted into ethyl ether. The combined fractions were washed with H$_2$O and brine and the dried (magnesium sulfate) extracts were concentrated to a yellow oil which was carried on without further purification.

IR (CHCl$_3$): 3620, 3450 (v. broad), 3005 cm$^{-1}$.

$^1$H NMR (CDCl$_3$): 2.38 (S, 3H); 4.56 (s, 2H); 7.25 to 7.60 (m, 6H);

$^{13}$C NMR (CDCl$_3$): 11.5, 54.8, 117.9, 127.2, 127.5, 128.1, 128.9, 132.7, 137.4, 151.9.

HRMS exact mass calculated for C$_{12}$H$_{12}$O$_2$ (M+) 188 0837, found 188.0850.

3-Dodecoyloxymethyl-2-methyl-4-phenylfuran

To a stirred solution of 2-methyl-4-phenyl-3-furylmethanol (Compound 17, 48 mg, 0.26 mmol) and triethylamine (39 mg. 0.38 mmol) in tetrahydrofuran (3 ml) at 0 degrees under argon was added lauroyl chloride (73 mg. 0.33 mmol). This solution was warmed gradually to room temperature and stirred for 4½ hours. The organics were extracted into ethyl ether and washed with a 5% aqueous sodium bicarbonate solution, H$_2$O and brine. Evaporation of the dried (magnesium sulfate) extracts gave an oil which was purified by flash chromatography on silica using 3% ether/hexanes to give the title compound.

IR (CHCl$_3$): 3010, 1725 cm$^{-1}$.

$^1$H NMR (CDCl$_3$): 0.86 (t, J=6.7 Hz, 3H); 1.20 to 1.32 (m, 16H); 1.50 to 1.64 (m, 2H); 2.23 to 2.32 (m, 2H); 2.36 (s, 3H); 4.97 (s, 2H); 7.29 to 7.42 (m, 6H).

$^{13}$C NMR (CDCl$_3$): 11.7, 13.9, 22.5, 24.7, 28.9, 29.06, 29.12, 29.3, 29.4, 31.7, 34.2, 56.5, 113.7, 127.3, 127.9, 128.1, 128.8, 132.5, 137.6, 153.3, 174.1.

4-Dodecoyloxymethyl-5-hydroxy-5-methyl-3-phenyl-2-furanone

A mixture of 3-dodecoyloxymethyl-2-methyl-4-phenylfuran (40 mg, 0.11 mmol), water (a few drops) and Rose Bengal on polymer beads (240 mg) in tetrahydrofuran (40 ml) was exposed to singlet oxygen at 0 degrees for 3 hours. The Rose Bengal was filtered off and the residue was concentrated to a pink oil which was purified by flash chromatography on silica using 15% ethyl acetate/hexanes. The furanone was further purified by HPLC chromatography on a normal phase partisil 10 column using 15% ethyl acetate/hexanes to give the title compound.

IR (CHCl$_3$): 3020, 1765, 1740 cm$^{-1}$.

$^1$H NMR (CDCl$_3$): 0.85 (t, J=6.7 Hz, 3H): 1.10 to 1.21 (m, 16H); 1.35 to 1.49 (m, 2H); 1.77 (s, 3H); 2.11 (t, J=7.6 Hz, 2H); 3.70 to 3.90 (brs, 1H); 5.02 (s, 2H); 7.37 to 7.50 (m, 5H).

$^{13}$C NMR (CDCl$_3$): 13.9, 22.5, 24.0, 24.4, 28.9, 29.0, 29.1, 29.2, 29.4, 31.7, 33.6, 57.2, 104.4 128.4, 128.7, 129.4, 129.8, 131.4, 154.4, 169.0, 173.9.

HRMS: exact mass calculated for C$_{24}$H$_{35}$O$_5$(MH+) 403.2484, found 403.2497.

5-Methyl-2-triethylsilyl-4-furylmethanol

LiAlH$_4$ (1.0M solution in hexane, 0.51 ml, 0.51 mmol) was added dropwise to a solution of 5-methyl-2-triethylsilyl-4-furaldehyde (230 mg, 1.03 mmol) in tetrahydrofuran (15 ml) at 0 degrees under argon. The stirring solution was allowed to warm to room temperature gradually over ½ hour. The reaction was quenched with 10% aqueous HCl and the organics were extracted into ethyl ether. The combined fractions were washed with H$_2$O and brine. Evaporation of the dried (magnesium sulfate) extracts gave an oil which was purified by filtration through silica using 10% ethyl ether/hexanes to give the title compound.

IR (CHCl$_3$): 3610 (sharp), 3440 (broad), 2940 cm$^{-1}$.

$^1$H NMR (CDCl$_3$) 0.71 (q, J=7.7 Hz, 6H); 0.96 (t, J=7.7 Hz, 9H); 2.25 (s, 3H); 2.40 (brs, 1H); 4.38 (s, 2H); 6.59 (s, 1H).

$^{13}$C NMR (CDCl$_3$): 2.9, 11.5, 56.2, 118.9, 122.3, 153.7, 156.0.

4-Dodecoyloxymethyl-5-methyl-2-triethylsilylfuran

To a stirred solution of 5-methyl-2-triethylsilyl-4-furylmethanol (208 mg. 0.92 mmol) and triethylamine (121 mg, 1.20 mmol) in tetrahydrofuran (10 ml) at 0 degrees under argon was added lauroyl chloride 302 mg, 1.38 mmol). This solution was allowed to warm gradually to room temperature and quenched with a 10% aqueous HCl solution. The organics were extracted into hexanes and the combined fractions were washed with a saturated aqueous solution of sodium bicarbonate, H$_2$O and brine. Evaporation of the dried (magnesium sulfate) extracts gave an oil which was purified by filtration through silica using 2% ethyl ether/hexanes to give the title compound.

IR (CHCl$_3$): 1725 cm$^{-1}$.

¹H NMR (CDCl₃): 0.75 (q, J=7.7 Hz, 6H); 0.88 (t, J=6.7 Hz, 3H), 0.98 (t, J=7.7 Hz, 9H); 1.20 to 1.35 (m, 16H); 1.56 to 1.68 (m, 2H); 2.30 (t, J=7.5 Hz); 2.31 (s, 3H); 4.91 (s, 2H); 6.57 (s, 1H).

¹³C NMR (CDCl₃): 2.9, 7.0, 11.7, 13.8, 22.6, 24.8, 28.9, 29.08, 29.14, 29.3, 29.4, 31.7, 34.2, 57.9, 114.7, 122.9, 155.3, 156.3, 174.2.

4-Dodecoyloxymethyl-5-hydroxy-5-methyl-2-furanone

A mixture of 4-dodecoyloxymethyl-5-methyl-2-triethylsilylfuran (180 mg. 0.44 mmol), water (a few drops) and Rose Bengal on polymer beads (360 mg) in tetrahydrofuran (70 ml) was exposed to singlet oxygen at 0 degrees until no starting material was visible (via TLC). The Rose Bengal was filtered off and the residue was concentrated to a pink oil which was purified by flash chromatography on silica using 30% ethyl acetate/hexanes to give the titled furanone.

IR (CHCl₃): 3400 (v. broad), 1750 (strong) cm⁻¹.

¹H NMR (CDCl₃): 0.88 (t, J=6.7 Hz 3H); 1.20 to 1.37 (m, 16H); 1.59 to 1.70 (m, 2H); 1.72 (s, 3H); 2.40 (t, J=7.6 Hz, 2H); 3.20 to 4.40 (v. brs, 1H); 4.93 (s, 2H); 5.94 (s, 1H).

¹³C NMR (CDCl₃): 13.8, 22.4, 23.7, 24.5, 28.8, 28.9, 29.0, 29.2, 29.3, 31.6, 33.7, 58.4, 105.9, 117.0, 166.2, 170.3, 173.7.

EXAMPLE 13

2-Trimethylsilyl-3-furaldehyde

N,N',N'-Trimethylethylenediamine (9.72 ml, 76 mmol) was added to a solution of n-butyl lithium (a 2.5M solution in hexane; 30 5 ml, 76 mmol) in tetrahydrofuran (200 ml) at −78° under argon. After 15 minutes, 3-furaldehyde 6.3 ml, 72.8 mmol) was added, which was followed after 25 minutes by n-butyl-lithium (32 ml, 80 mmol). Even better results (more regioselectivity) are obtained when methyl lithium is used instead of butyl lithium. After another 4 hours, chlorotrimethylsilane (11 ml, 87 mmol) was added. Stirring was continued for 14 hours, while the cooling bath was allowed to warm to room temperature. The mixture was quenched with ice-cold hydrochloric acid was extracted with ethyl ether. Evaporation of the dried (magnesium sulfate) extracts gave an oil, which was distilled to give the title aldehyde, b.p. 40°-1°/0.1 torr.

¹H NMR (CDCl₃): 2.89 (s, 3H), 6.97 (d, 1H, J=1.9 Hz), 7.59 (d, 1H, J=1.9 Hz) and 10.23 (s, 1H).

¹³CNMR (CDCl₃): −1.89, 107.7, 137.1, 147.3, 171.1 and 185.7.

Substituting chlorotrimethylsilane with chlorotriethylsilane gave 2-triethylsilyl-3-furaldehyde (Compound 15).

4-(1-Acetoxynonyl)-2-trimethylsilylfuran

A solution of 2-trimethylsilyl-3-furaldehyde (1.0 g, 5.90 mmol) in tetrahydrofuran (2 ml) was added to a solution of octyl magnesium bromide (11.9 mmol; prepared from 2.30 g 1-bromo octane and 286 mg magnesium turnings) at 0. After all the aldehyde was consumed in the reaction, as monitored by thin layer chromatography (tlc) acetic anhydride was added and stirring was continued for overnight. Thereafter, the mixture was quenched with dilute hydrochloric acid and was extracted with ethyl ether. Evaporation of the dried (magnesium sulfate) extracts gave an oil, which was purified by a silica column using 5% ethyl ether/hexane to give the title furan.

¹HNMR (CDCl₃): 0.34 (s, 9H), 0.89 (t, 3H, J=7.2 Hz), 1.27 (br s, 12H), 1.75 (2m, 2H), 2.05 (s, 3H), 5.89 (t, 1H, J=7.3 Hz), 6.45 (d, 1H, J=1.6 Hz) and 7.28 (br s, 1H).

LRMS (m/e, % abundance) 324 (m+, 7), 282(43), 281(88), 267(13), 266(31), 265(15), 169(26), 153(47), 117(100), 75(38) and 73(78).

3-(1-Acetoxynonyl)-5-hydroxy-2(5H)-furanone

A mixture of 3-(1-acetoxynonyl)-2-trimethylsilylfuran (1.40 g, 4.32 mmol), water (5 drops) and Rose Bengal (3 mg) in tetrahydrofuran (20 ml) was exposed to singlet oxygen at 0° for 6 hours. The residue, after solvent removal, was purified by a silica column using 50% ethyl ether/hexane to give the title furanone.

¹HNMR (CDCl₃): 0.91 (t, 3H, J=7.0 Hz), 1.29 (br s, 12H), 1.85 (m, 2H), 2.15 (s, 3H), 4.20 (br, 1H), 5.60 (m, 1H), 6.14 (br s, 1H) and 7.00 (br s, 1H).

¹³CNMR (CDCl₃): 13.9, 20.8, 22.5, 24.8, 29.0, 29.2, 31.7, 32.6, 32.8, 68.4, 68.7, 96.9, 97.2, 136.7, 145.3, 169.7, 170.6 and 170.8.

HRMS exact mass calculated for C₁₅H₂₅O₅ (M+H)+ 285.1702, found 285.1709.

3-(1-Acetoxynonyl)-2(5H)-furanone (Compound 70)

Sodium borohydride (29.3 mg, 0.76 mmol) was added to a solution of 3-(1-acetoxynonyl)-5-hydroxy-2(5H)-furanone (220 mg, 0.78 mmol) in methanol (1 ml) and tetrahydrofuran (5 ml). Stirring was continued for 14 hours at room temperature and most of the solvent was evaporated. The residue was acidified with ice-cold dilute hydrochloric acid and was extracted with ethyl acetate. Evaporation of the dried (magnesium sulfate) extracts gave an oil, which was purified by preparative silica plates (developed with 60% ethyl ether/hexane) to give the title furanone.

¹HNMR (CDCl₃): 0.88 (t, 3H, J=6.5 Hz), 1.25 (m, 12H), 1.85 (m, 2H), 2.11 (s, 3H), 4.82 (m, 2H), 5.61 (t, 1H, J=6.3 Hz) and 7.29 (t, 1H, J=1.5 Hz).

¹³CNMR (CDCl₃): 14.0, 20.9, 22.6, 24.9, 28.9, 29.1, 29.3, 31.7, 32.6, 68.9, 70.1, 133.6, 146.1, 169.9 and 171.6.

HRMS exact mass calculated for C₁₅H₂₅O₄ (M+H)+ 269.1753, found 269.1735.

3-(1-Hydroxytridecyl)-2-trimethylsilylfuran

A solution of dodecylmagnesium bromide (a 1M solution in tetrahydrofuran; 14.3 ml; 14.3 mmol) was added to a solution of 2-trimethylsilyl-3-furaldehyde (1.20 g, 7.1 mmol) in tetrahydrofuran (30 ml) at 0°. After all the aldehyde has reacted, as shown by tlc, the mixture was quenched with dilute hydrochloric acid and was extracted with ethyl ether. Evaporation of the dried (magnesium sulfate) extracts gave an oil, which was purified by a silica column using 5% ethyl ether/hexane to give the title furan.

¹HNMR (CDCl₃): 0.34 (s, 9H), 0.91 (t, 3H, J=6.9 Hz), 1.28 (br s, 20H), 1.75 (m, 2H), 4.75 (m, 1H), 6.48 (d, 1H, J=1.7 Hz) and 7.60 (d, 1H, J=1.7 Hz).

HRMS exact mass calculated for C₂₀H₃₈SiO₂(M+) 338.2641, found 338.2643.

3-(1-Hydroxytridecyl)-5-hydroxy-2(5H)-furanone

A mixture of 3-(1-hydroxytridecyl)-2-trimethylsilylfuran (1.17 g, 3.46 mmol), water (5 drops) and Rose Bengal (5 mg) in tetrahydrofuran (20 ml) was exposed to singlet oxygen at 0° for 6 hours. The residue, after solvent removal, was purified by a silica column using 60% ethyl ether/hexane to give the title furanone.

¹HNMR (CDCl₃): 0.90 (t, 3H, J=7.0 Hz), 1.28 (br s, 20H), 1.75 (m, 2H), 2.85 (br, 1H), 4.50 (br t, 1H), 4.70 (br, 1H), 6.15 (br s, 1H) and 7.06 (br s, 1H).

¹³CNMR (CDCl₃): 14.0, 22.6, 25.3, 29.3, 29.4, 29.6, 29.7, 31.9, 35.0, 66.2, 66.5, 97.5, 97.6, 139.8, 145.2, 145.4 and 171.4.

HRMS exact mass calculated for $C_{17}H_{31}O_4$ (M+H)+ 299.2222, found 299.2224.

3-(1-Hydroxytridecyl)-2(5H)-furanone (Compound 71)

Sodium borohydride (31.3 mg, 0.83 mmol) was added to a solution of 3(1-hydroxytridecyl)-5-hydroxy-2(5H)-furanone (246.9 mg, 0.83 mmol) in methanol (1 ml) and tetrahydrofuran (5 ml). When all the furanone was consumed, most of the solvent was evaporated. The residue was acidified with dilute hydrochloric acid and was extracted with ethyl acetate. Evaporation of the dried (magnesium sulfate) extracts gave an oil, which was purified by preparative silica plates (developed with 60% ethyl ether/hexane) to give the titled furanone.

¹HNMR (CDCl₃): 0.88 (t, 3H, J=6.2 Hz), 1.25 (m, 20H), 1.70 (m, 2H), 2.55 (br s, 1H), 4.51 (t, 1H, J=6.2 Hz), 4.84 (m, 2H) and 7.30 (t, 1H, J=1.5 Hz).

¹³CNMR (CDCl₃): 13.9, 22.5, 25.1, 29.2, 29.3, 29.4, 29.5, 31.8, 35.3, 66.8, 70.4, 136.5, 145.1 and 173.2.

HRMS exact mass calculated for $C_{17}H_{31}O_3$(M+H)+ 283.2273, found 283.2254.

3-(1-Acetoxytridecyl)-2-trimethylsilylfuran

Dodecylmagnesium bromide (a 1.0M solution in tetrahydrofuran; 14.3 ml; 14.3 mmol) was added to a solution 2-trimethylsilyl-3-furaldehyde (1.20 g, 7.1 mmol) in tetrahydrofuran (20 ml). When all the aldehyde was consumed, as monitored by tlc, acetic anhydride (2.02 ml, 21.4 mmol) was added Stirring was continued at room temperature for 14 hours. The mixture was quenched with water and was extracted with ethyl ether. Evaporation of the dried (magnesium sulfate) extracts gave an oil, which was purified by a silica column using 2% ethyl ether/hexane to give the titled furan.

¹HNMR (CDCl₃): 0.34 (s, 9H), 0.89 (t, 3H, J=6.9 Hz), 1.26 (br s, 20H), 1.75 (m, 2H), 2.04 (s, 3H), 5.88 (t, 1H, J=7.1 Hz), 6.43 (br s, 1H) and 7.58 (br s, 1H).

HRMS exact mass calculated for $C_{22}H_{40}O_3Si$(M+) 380.2747, found 380.2752.

3-(1-Acetoxytridecyl)-5-hydroxy-2(5H)-furanone

A mixture of 3-(1-acetoxytridecyl)-2-trimethylsilylfuran (1.25 g, 3.29 mmol), water (5 drops) and Rose Bengal (5 mg) in tetrahydrofuran (10 ml) was exposed to singlet oxygen at 0° for 6 hours. The residue, after solvent removal, was purified by a silica column using 50% ethyl ether/hexane to give the title furanone.

¹HNMR (CDCl₃): 0.93 (t, 3H, J=6.9 Hz), 1.29 (br s, 20H), 1.85 (m, 2H), 2.17 (s, 3H), 4.20 (br, 1H), 5.60 (br t, 1H), 6.15 (br s, 1H) and 7.02 (br s, 1H).

¹³CNMR (CDCl₃): 14.0, 20.8, 22.6, 24.9, 28.8, 28.9, 29.0, 29.1, 29.3, 29.5, 29.6, 31.5, 31.8, 32.7, 32.8, 68.5, 68.7, 68.8, 96.9, 97.0, 97.2, 136.8, 145.2, 145.3, 169.7, 170.6 and 170.7.

HRMS exact mass calculated for $C_{19}H_{33}O_5$ (M+H)+ 341.2328, found 341.2339.

3-(1-Acetoxytridecyl)-2(5H)-furanone (Compound 72)

Sodium borohydride (251 mg, 0.74 mmol) was added to a solution of 3-(1-acetoxytridecyl)-5-hydroxy-2(5H)-furanone (251 mg, 0.74 mmol) in methanol (1 ml) and tetrahydrofuran (5 ml) at room temperature. When all the furanone were consumed, as monitored by tlc, the solution was evaporated to dryness. The residue was acidified with dilute hydrochloric acid and was extracted with ethyl acetate. Evaporation of the dried (magnesium sulfate) extracts gave an oil, which was purified by preparative silica plates (developed with 60% ethyl ether/hexane) to give the title furanone.

¹HNMR (CDCl₃): 0.88 (t, 3H, J—6.5 Hz), 1.25 (m, 20H), 1.85 (m, 2H), 2.10 (s, 3H), 4.80 (m, 2H), 5.60 (t, 1H, J=6.0 Hz) and 7.29 (t, 1H, J=1.6 Hz).

¹³CNMR (CDCl₃): 13.7, 20.6, 22.3, 24.7, 28.9, 29.0, 29.1, 29.2, 29.3, 31.6, 32.4, 68.8, 70.0, 133.7, 146.4, 170.2 and 171.9.

HRMS exact mass calculated for $C_{19}H_{33}O_4$ (M+H)+ 325.2379, found 325.2376.

3-(1-phenylcarbamoyloxytridecyl)-2(5H)-furanone 3-(1-Hydroxytridecyl)-2-triethylsilylfuran is reacted with phenyl isocyanate and copper (2) chloride in dimethylformamide to give 3-(1-phenylcarbamoyloxytridecyl)-2-triethylsilylfuran. Oxidizing the latter intermediate with singlet oxygen and thereafter reduction with sodium borohydride gives 3-(1-phenylcarbamoyloxytridecyl)-2(5H)-furanone. Substituting phenyl isocyanate with diethyl chlorophosphate, gives 3-(1-diethylphosphonooxytridecyl)-2(5H)-furanone. Substituting phenyl isocyanate with ethyl chloroformate, gives 3-(1-ethoxycarbonyloxytridecyl)-2(5H)-furanone. Substituting phenyl isocyanate with methoxyethyl chloromethyl ether, gives 3-[1-(2-methoxy)ethoxymethoxy]tridecyl-2(5H)-furanone.

3-(1-acetamidotridecyl)-2(5H)-furanone

Reacting 3-(1-hydroxytridecyl)-2-triethylsilylfuran with diphenylphosphoryl azide and diethyl azidocarboxylate gives 3(1-azidotridecyl)-2-triethylsilylfuran. Reducing this intermediate with lithium aluminum hydride, followed by acetylation with acetic anhydide gives 3-(1-acetamido tridecyl)-2-triethylsilylfuran. Singlet oxygen oxidation of this amide, followed by reduction with sodium borohydride gives 3-(1-acetamidotridecyl)-2(5H)-furanone.

3-(1-methanesulfonamidotridecyl)-2(5H)-furanone

Reducing 3-(1-azidotridecyl)-2-triethylsilylfyuran with lithium aluminum hydride, as in Example 8, followed by reacting the intermediate with methanesulfonyl chloride, gives 3(1-methanesulfonamidotridecyl)-2-triethylsilylfuran. Oxidizing this sulfonamide followed by reduction with sodium borohydride gives 3-(1-methanesulfonamidotridecyl)-2(5H)-furanone.

ACTIVITY DATA

In the above-described phospholipase A₂ (PLA₂) and calcium+ channel mobilization assays certain examplary compounds made from the synthetic intermediate compounds of the present invention had the following activities.

TABLE 1

| Phospholipase A₂ Assay. | |
|---|---|
| Compound name or number | IC₅₀ (micromolar) |
| manoalide* | 0.03 |
| 20 | >1 |
| 21 | 0.03 |
| 22 | 0.05 |
| 23 | 0.04 |
| 24 | 0.34 |

TABLE 1-continued

| Phospholipase A2 Assay. | |
|---|---|
| Compound name or number | IC50 (micromolar) |
| 25 | 0.26 |
| 26 | 0.13 |
| 27 | 0.04 |
| 28 | 0.04 |
| 29 | 0.07 |
| 30 | 0.06 |
| 31 | 0.05 |
| 32 | 0.48 |
| 40 | 0.28 |
| 41 | 0.04 |
| 42 | 0.03 |
| 43 | 0.03 |
| 44 | 0.09 |
| 45 | 0.05 |
| 46 | 0.02 |
| 47 | 0.06 |
| 50 | 0.5 |
| 51 | 0.09 |
| 60 | 0.06 |
| 61 | >1 |
| 62 | 0.24 |

*Data for monoalide are provided for comparison.

TABLE 2

| | Calcium Channel Inhibition Assay. | |
|---|---|---|
| Compound number | IC50 (umolar) (TRH regulated) | IC50 (umolar) (KCl regulated) |
| 70 | 4.9 | 3.4 |
| 71 | 2 | 1.1 |
| 72 | 16.9 | 0.88 |
| manoalide | 1.0 | 1.0 |

What is claimed is:
1. A compound of the formula

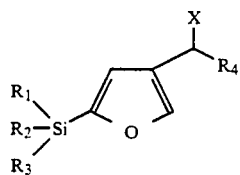

where $R_1$, $R_2$ and $R_3$ independently are D-alkyl of 1 to 6 carbons, or branched chain alkyl of 1 to 6 carbons;
X is H, OH, $NH_2$, I, Br or SH;
$R_4$ is H, alkyl of 1–20 carbons, phenyl[$C_1$–$C_{20}$alkyl], naphthyl[$C_1$–$C_{20}$alkyl], $CH_2OH$, $CH_2NH_2$, $CH_2CH_2OH$, $CH_2$—CHO, $CH_2$—COOH or $CH_2$—$COOR_5$, and
$R_5$ is alkyl of 1 to 6 carbons,
with the proviso that when X is hydrogen then $R_4$ is selected from the group consisting of $CH_2OH$, $CH_2NH_2$, $CH_2CH_2OH$, $CH_2$—CHO, or $CH_2$—$COOR_5$.

2. A compound of claim 1 wherein $R_4$ is hydrogen.
3. A compound of claim 2 where X is OH.
4. A compound of claim 2 where X is SH.
5. A compound of claim 2 where X is $NH_2$.
6. A compound of claim 2 which is 2-triethylsilyl-4-hydroxymethylfuran, 2-trimethylsilyl-4-hydroxymethylfuran, 2-triethylsilyl-4-aminomethylfuran, 2-trimethylsilyl-4-aminomethylfuran, 2-triethylsilyl-4-iodomethylfuran, or 2-trimethylsilyl-4-iodomethylfuran.
7. A compound of claim 1 where $R_4$ is D-alkyl of 9 to 20 carbons.
8. A compound of claim 7 where $R_4$ is n-dodecyl.
9. A compound of claim 8 which is 2-triethylsilyl-4-(1-hydroxy-tridecyl)-furan, 2-trimethylsilyl-4-(1-hydroxy-tridecyl)-furan, 2-triethylsilyl-4-(1-amino-tridecyl)-furan, 2-trimethylsilyl-4-(1-amino-tridecyl)-furan, 2-triethylsilyl-4-(1-mercapto-tridecyl)-furan, or 2-trimethylsilyl-4-(1-mercapto-tridecyl)-furan.
10. A compound of claim 1 where $R_4$ is $CH_2$—$CH_2OH$, $CH_2$—CHO or $CH_2$—$COOR_5$.
11. A compound of claim 10 where X is hydrogen.
12. A compound of claim 11 which is 3-(2-triethylsilyl-4-furyl)propan-1-ol, 3-(2-trimethylsilyl-4-furyl)propan-1-ol, 3-(2-triethylsilyl-4-furyl)propan-1-al, 3-(2-trimethylsilyl-4-furyl)propan-1-al, methyl 3-(2-triethylsilyl-4-furyl)propionate, or methyl 3-(2-trimethylsilyl-4-furyl)propionate.
13. A compound of claim 1 wherein $R_4$ is $CH_2OH$ or $CH_2NH_2$.
14. A compound of claim 13 wherein X is OH or $NH_2$.
15. A compound of claim 14 which is 2-triethylsilyl-4-(1,2-dihydroxy-ethyl)furan, 2-trimethylsilyl-4-(1,2-dihydroxyethyl)furan, 2-triethylsilyl-4-(1-hydroxy-2-amino-ethyl)furan, 2-trimethylsilyl-4-(1-hydroxy-2-amino-ethyl)furan, 2-triethylsilyl-4-(1,2-diamino-ethyl)furan, or 2-trimethylsilyl-4-(1,2-diamino-ethyl)furan.

* * * * *

UNITED STATES PATENT AND TRADEMARK OFFICE
CERTIFICATE OF CORRECTION

PATENT NO. : 5,171,863
DATED : December 15, 1992
INVENTOR(S) : Gary C. M. Lee, et al.

It is certified that error appears in the above-identified patent and that said Letters Patent is hereby corrected as shown below:

On the title page,

In the Abstract, page 2, first line after Formula 2, change "$R_2\ R_3$" to —$R_2$ and $R_3$—;

Column 1, line 54, change "a..," to —al.,—;

Column 3, line 14, "D-alkyl" should be —$\underline{n}$-alkyl—;

Column 12, line 42, change "Formula 10" to —Formula 11—;

Column 16, line 16, change "1-" to — 2- —;

Column 18, line 63, "(Dodecylohosphonyloxymethyl)" should be —(Dodecylphosphonyloxymethyl)—;

Column 21, line 35, after "$(M + NH_4)^+$ insert —:—;

Column 22, line 38, after "to" insert —give the title furanone as an off-white solid.—;

Column 25, line 32, at the beginning of the line, change "1-" to — 4-(1- —;

Column 26, line 31, at the beginning of the line, change "4-1-(3-" to — 4-[1-(3- —;

Column 26, line 54, at the beginning of the line, change "4-1-(3-" to — 4-[1-(3- —;

Column 27, line 28, at the beginning of the line, change "4-1-(" to —4-[1-(—;

Column 28, line 46, at the beginning of the line, change "4-1-(" to —4-[1-(—;

Column 29, line 66, delete "0.1), 485 $(M + NH_4+$," and insert in its place —$((M+NH_4)^+$,—

Column 30, line 30, after "10" insert —minutes trichloroacetic anhydride (98 microliter, 0.54 mmol) was added and stirring was continued at room temperature overnight. The mixture was quenched with water and extracted—;

UNITED STATES PATENT AND TRADEMARK OFFICE
CERTIFICATE OF CORRECTION

PATENT NO. : 5,171,863
DATED : December 15, 1992
INVENTOR(S) : Gary C. M. Lee, et al.

It is certified that error appears in the above-identified patent and that said Letters Patent is hereby corrected as shown below:

Column 30, line 58, "$C_{13}$" should be —$Cl_3$—;

Column 32, line 21, change "3-1-(" insert —3-[1-(—;

Column 32, line 42, before "1-(" insert —3-[—;

Column 33, line 9, change "3-1-" to — 3-[1- —;

Column 33, line 28, change "4-1-(" to —4-[1-(—;

Column 33, line 39, after "($CDCL_3$)" insert —:—;

Column 34, line 16, change "($CCH_3$" to —($OCH_3$—;

Column 34, line 18, change "($CCH_3$" to —($OCH_3$—;

Column 34, line 21, "3-(N" should be —3-[(N—;

Column 34, line 40, delete the "[" at the beginning of the line;

Column 36, line 8, after "m/e" insert —:—;

Column 36, line 38, "J = 73" should be —J = 7.3—;

Column 37, line 14, "306 1963" should be —306.1963—;

Column 37, line 57, after "6.19" insert —(d, J=16Hz, 1H); 6.13 (broad s, 1H); 6.06 (s, 1H); 5.87 (s,—;

Column 39, line 39, "4.I8" should be —4.18—;

Column 40, line 35, at the end of the line insert —.—;

Column 42, line 41, at the end of the line, change "4-yl)-" to — 4-furyl)- —;

Column 42, line 43, after "in" insert —tetrahydrofuran gives 3-(7-oxo-5-hexadecenyl)-5- —;

Column 43, line 20, before "(M+" insert another —(—;

Column 44, line 14, at the end of the line, the "N07" should be —$NO_7$—;

Column 44, line 15, "($M+NH_4$)" should be —$(M+NH_4)^+$—;

UNITED STATES PATENT AND TRADEMARK OFFICE
CERTIFICATE OF CORRECTION

PATENT NO. : 5,171,863

DATED : December 15, 1992

INVENTOR(S) : Gary C. M. Lee, et al.

It is certified that error appears in the above-identified patent and that said Letters Patent is hereby corrected as shown below:

Column 44, line 18, "3furaldehyde" should be — 3-furaldehyde —;

Column 44, line 22, "dodecyanoyloxyethyl" should be —dodecanoyloxyethyl—;

Column 44, line 37, "dodecyanoloxy" should be —dodecanoyloxy—;

Column 44, line 43, "2-OP(O)(CCH$_3$)" should be —2-OP(O)(OCH$_3$);

Column 44, line 67, "$^1$H" should be —1H—;

Column 46, line 42, change "4-(1-" to — 4-[(1- —;

Column 46, line 62, after "exact" insert —mass—;

Column 47, line 55, "4-(1-" should be — 4-[(1- —;

Column 48, line 25, "6.0" should be —26.0—;

Column 48, line 49, "28 7" should be —28.7—;

Column 49, lines 21 and 22, ..."oioerazine)amido-lethyl"... should be ...—piperazine)amido]ethyl—...;

Column 49, line 23, "4-1-" should be — 4-[1- —;

Column 49, line 45, at the end of the line "9H), should be —9H,—;

Column 52, line 24, "Bis-(2-"... should be —Bis-[(2- —...;

Column 54, line 10 , ..."propy-5-"... should be ...— propyl-5- —...;

Column 54, line 64, at the beginning of the line, "5Methyl-"... should be — 5-Methyl- —...;

Column 54, line 65, at the beginning of the line the "D" should be —n—;

Column 56, line 52, in the middle of the line the "-2-" should be — -3- —;

Column 57, line 5, after "b)" change "4-2-" to — 4-[2- —;

Column 58, line 51, at the very beginning of the line, change "N" to —N- —;

Column 58, line 63, change ..."2-(5H)"... to ...—2(5H)—...;

UNITED STATES PATENT AND TRADEMARK OFFICE
CERTIFICATE OF CORRECTION

PATENT NO. : 5,171,863

DATED : December 15, 1992

INVENTOR(S) : Gary C. M. Lee, et al.

It is certified that error appears in the above-identified patent and that said Letters Patent is hereby corrected as shown below:

Column 58, line 66, before "a" insert —(—;

Column 61, line 41, after "29.4" insert —31.7, 32.9, 33.5—;

Column 61, line 44, after "491[" insert —(— before the "M";

Column 61, line 64, the "2-" at the beginning of the line should be — 3- —;

Column 62, line 62, after "($CDCl_3$)" insert —:—;

Column 63, line 12, after "($CHCl_3$)" insert —:—;

Column 63, line 49, after "($CHCl_3$)" insert —:—;

Column 63, line 67, after "hyde" insert —.—;

Column 65, line 49, change "$^1H$" to —1H—;

Column 65, lines 53 & 54, "188 0837" should be —188.0837—;

Column 66, line 48, after "($CDCl_3$)" insert —:—;

Column 67, line 3, after "Hz" insert —, 2H—;

Column 67, line 33, "30 5" should be —30.5—;

Column 67, line 43, after "acid" insert —and—;

Column 67, line 60, change "0" to —$0°$—;

Column 69, line 35, after "added" insert —.—;

UNITED STATES PATENT AND TRADEMARK OFFICE
CERTIFICATE OF CORRECTION

PATENT NO. : 5,171,863

DATED : December 15, 1992

INVENTOR(S) : Gary C.M. Lee, et al

It is certified that error appears in the above-indentified patent and that said Letters Patent is hereby corrected as shown below:

Column 70, line 46, at the end of the line, change ..."fyuran" to ...--furan--;
Column 70, line 49, after "gives", "3(1-"... should be -- 3-(1- --...;
Column 71, line 45, Claim 1, change "D-alkyl" to --n-alkyl--;
Column 72, line 19, Claim 7, change "D-alkyl" to --n-alkyl--.

Signed and Sealed this

Twenty-eighth Day of December, 1993

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,171,863
DATED : December 15, 1992
INVENTOR(S) : Gary C. M. Lee, et al.

It is certified that error appears in the above-identified patent and that said Letters Patent is hereby corrected as shown below:

Column 18, line 23, "73)100)" should be —73(100)—;

Column 28, line 65, "868.0" should be —68.0—;

Column 50, line 15, "piperazine)amido lethyl-5-hy" should be
—piperazine)amido]ethyl-5-hydroxy-2(5H)-furanone—; and Column 71, line 23, "monoalide" should be —manoalide—.

Signed and Sealed this

Twenty-ninth Day of March, 1994

*Attest:*

BRUCE LEHMAN

*Attesting Officer*  *Commissioner of Patents and Trademarks*